US006403765B1

(12) United States Patent
Alnemri

(10) Patent No.: US 6,403,765 B1
(45) Date of Patent: Jun. 11, 2002

(54) TRUNCATED APAF-1 AND METHODS OF USE THEREOF

(75) Inventor: Emad S. Alnemri, Township Upper Dublin, County Montgomery, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/098,310

(22) Filed: Jun. 16, 1998

(51) Int. Cl.$^7$ ............................................. C07K 14/435
(52) U.S. Cl. ......................... 530/350; 530/300; 530/324
(58) Field of Search ................................ 530/300, 350, 530/324

(56) References Cited

FOREIGN PATENT DOCUMENTS

WO    WO 98/55615    12/1998

OTHER PUBLICATIONS

Ahmad et al., "CRADD, a Novel Human Apoptotic Adaptor Moelcule for Caspase–2, and FasL/Tumor Necrosis Factor Receptor–Interacting Protein RIP," *Cancer Research* 57:615–619, 1997.
Boldin et al., "A Novel Protein That Interacts with the Death Domain of Fas/APO1 Contains a Sequence Motif Related to the Death Domain," *J. Biol. Chem.* 270(14):7795–7798, 1995.
Chinnaiyan et al., "FADD, a Novel Death Domain–Containing Protein, Interacts with the Death Domain of Fas and Initiates Apoptosis," *Cell* 8:505,512, 1995.
Chinnaiyan et al., "Interaction of CED–4 with CED–3 and CED–9: A Molecular Framework for Cell Death," *Science* 275(5303):1122–1126, 1997.
Chinnaiyan et al., "Role of CED–4 in the Activation of CED–3," *Nature* 338(6644):718–729, 1997.
Duan and Dixit, "RAIDD is a New 'Death' Adaptor Molecular," *Nature* 385(6611):86–89. 1997.
Hegde et al., "Blk, a BH3–Containing Mouse Protein That Interacts with Bcl–2 and Bcl–xL, Is a Potent Death Agonist," *J. Biol. Chem.* 273(14):7783–7786, 1998.
Hoffman and Bucher, "The CARD Domain: A New Apoptotic Signalling Motif," *TIBS* 22:155–156, 1997.

Hu et al., "Bcl–XL Interacts with Apaf–1 and Inhibits Apaf–1–Dependent Caspase–9 Activation," *Proc. Natl. Acad. Sci. USA* 95(8):4386–4391, 1998.
James et al., "CED–4 Induces Chromatin Condensation in *Schizosaccharomyces pombe* and Is Inhibited by Direct Physical Association with CED–9," *Current Biology* 7(4):246–252, 1997.
Li et al., "Cytochrome c and dATP–Dependent Formation of Apaf–1/Caspase–9 Complex Initiates an –Apoptotic Protease Cascade," *Cell 91*: 479–489, 1997.
Liu et al., "Induction of Apoptotic Program in Cell–Free Extracts: Requirement for dATP and Cytochrome c,"*Cell* 86:147–157, 1996.
MacFarlane et al., "Identification and Molecular Cloning of Two Novel Receptors for the Cytotoxic Ligand TRAIL," *J. Biol. Chem.* 272(41):25417–25420, 1997.
Seshagiri and Miller, "*Caenorhabditis elegans* CED–4 Stimulates CED–3 Processing and CED–3–Induced Apoptosis," *Current Biology* 7(7):455–460, 1997.
Srinivasula et al., "Autoactivation of Procaspase–9 by Apaf–1–Mediated Oligomerization," *Molecular Cell* 1:949–957, 1998.
Srinivasula et al., "The Ced–3/Interleukin 1β Converting Enzyme–Like Homolog Mch6 and the Lamin–Cleaving Enzyme Mch2α Are Substrates for the Apoptotic Mediator CPP32," *J. Biol. Chem.* 271(43):27099–27106, 1996.
Yuan and Horvitz, "*The Caenorhabditis elegans* Cell Death Gene ced–4 Encodes a Novel Protein and Is Expressed During the Period of Extensive Programmed Cell Death," *Development* 116(2):309–320, 1992.
Zou et al., "Apaf–1, a Human Protein Homologous to C. Elegans CED–4, Participates in Cytochrome c–Dependent Activation of Caspase–3," *Cell* 90:405–413, 1997.

*Primary Examiner*—Anthony C. Caputa
*Assistant Examiner*—Anne L. Holleran
(74) *Attorney, Agent, or Firm*—SEED Intellectual Property Law Group PLLC

(57) ABSTRACT

Truncated Apaf-1 nucleic acids and encoded polypeptides are provided. Also provided are self-oligomerizing caspase molecules capable of self-processing. In one embodiment the present invention provides methods for identifying apoptotic inhibitors and enhancers use whole cell or reconstituted component assay systems. In a further embodiment, truncated Apaf-1 and self-oligomerizing caspase constructs are described which can be provided to a cell, thereby inducing apoptosis.

2 Claims, 26 Drawing Sheets

```
AAGAAGAGGT AGCGAGTGGA CGTGACTGCT CTATCCCGGG CAAAAGGGAT AGAACCAGAG    60
GTGGGGAGTC TGGGCAGTCG GCGACCCGCG AAGACTTGAG GTGCCGCAGC GGCATCCGGA   120
GTAGCGCCGG GCTCCCTCCG GGGTGCAGCC GCCGTCGGGG GAAGGGCGCC ACAGGCCGGG   180
AAGACCTCCT CCCTTTGTGT CCAGTAGTGG GGTCCACCGG AGGGCGGCCC GTGGGCCGGG   240
CCTCACCGCG GCGCTCCGGG ACTGTGGGGT CAGGCTGCGT TGGGTGGACG CCCACCTCGC   300
CAACCTTCGG AGGTCCCTGG GGGTCTTCGT GCGCCCCGGG GCTGCAGAGA TCCAGGGGAG   360
GCGCCTGTGA GGCCCGGACC TGCCCCGGGG CGAAGGGTAT GTGGCGAGAC AGAGCCCTGC   420
ACCCCTAATT CCCGGTGGAA AACTCCTGTT GCCGTTTCCC TCCACCGGCC TGGAGTCTCC   480
CAGTCTTGTC CCGGCAGTGC CGCCCTCCCC ACTAAGACCT AGGCGCAAAG GCTTGGCTCA   540
TGGTTGACAG CTCAGAGAGA GAAAGATCTG AGGGAAG ATG GAT GCA AAA GCT CGA   595
                                        Met Asp Ala Lys Ala Arg
                                        1                       5
```

```
AAT TGT TTG CTT CAA CAT AGA GAA GCT CTG GAA AAG GAC ATC AAG ACA    643
Asn Cys Leu Leu Gln His Arg Glu Ala Leu Glu Lys Asp Ile Lys Thr
            10                  15                  20
TCC TAC ATC ATG GAT CAC ATG ATT AGT GAT GGA TTT TTA ACA ATA TCA    691
Ser Tyr Ile Met Asp His Met Ile Ser Asp Gly Phe Leu Thr Ile Ser
                25                  30                  35
GAA GAG GAA AAA GTA AGA AAT GAG CCC ACT CAA CAG CAA AGA GCA GCT    739
Glu Glu Glu Lys Val Arg Asn Glu Pro Thr Gln Gln Gln Arg Ala Ala
        40                  45                  50
ATG CTG ATT AAA ATG ATA CTT AAA AAA GAT AAT GAT TCC TAC GTA TCA    787
Met Leu Ile Lys Met Ile Leu Lys Lys Asp Asn Asp Ser Tyr Val Ser
55                  60                  65                  70
TTC TAC AAT GCT CTA CTA CAT GAA GGA TAT AAA GAT CTT GCT GCC CTT    835
Phe Tyr Asn Ala Leu Leu His Glu Gly Tyr Lys Asp Leu Ala Ala Leu
                75                  80                  85
CTC CAT GAT GGC ATT CCT GTT GTC TCT TCT TCC AGT GTA AGG ACA GTC    883
Leu His Asp Gly Ile Pro Val Val Ser Ser Ser Ser Val Arg Thr Val
                90                  95                 100
CTG TGT GAA GGT GGA GTA CCA CAG AGG CCA GTT GTT TTT GTC ACA AGG    931
Leu Cys Glu Gly Gly Val Pro Gln Arg Pro Val Val Phe Val Thr Arg
            105                 110                 115
AAG AAG CTG GTG AAT GCA ATT CAG CAG AAG CTC TCC AAA TTG AAA GGT    979
Lys Lys Leu Val Asn Ala Ile Gln Gln Lys Leu Ser Lys Leu Lys Gly
        120                 125                 130
GAA CCA GGA TGG GTC ACC ATA CAT GGA ATG GCA GGC TGT GGG AAG TCT   1027
Glu Pro Gly Trp Val Thr Ile His Gly Met Ala Gly Cys Gly Lys Ser
135                 140                 145                 150
GTA TTA GCT GCA GAA GCT GTT AGA GAT CAT TCC CTT TTA GAA GGT TGT   1075
Val Leu Ala Ala Glu Ala Val Arg Asp His Ser Leu Leu Glu Gly Cys
                155                 160                 165
TTC CCA GGG GGA GTG CAT TGG GTT TCA GTT GGG AAA CAA GAC AAA TCT   1123
Phe Pro Gly Gly Val His Trp Val Ser Val Gly Lys Gln Asp Lys Ser
                170                 175                 180
```

*Fig. 19A*

```
GGG CTT CTG ATG AAA CTG CAG AAT CTT TGC ACA CGG TTG GAT CAG GAT   1171
Gly Leu Leu Met Lys Leu Gln Asn Leu Cys Thr Arg Leu Asp Gln Asp
            185                 190                 195
GAG AGT TTT TCC CAG AGG CTT CCA CTT AAT ATT GAA GAG GCT AAA GAC   1219
Glu Ser Phe Ser Gln Arg Leu Pro Leu Asn Ile Glu Glu Ala Lys Asp
        200                 205                 210
CGT CTC CGC ATT CTG ATG CTT CGC AAA CAC CCA AGG TCT CTC TTG ATC   1267
Arg Leu Arg Ile Leu Met Leu Arg Lys His Pro Arg Ser Leu Leu Ile
215                 220                 225                 230
TTG GAT GAT GTT TGG GAC TCT TGG GTG TTG AAA GCT TTT GAC AGT CAG   1315
Leu Asp Asp Val Trp Asp Ser Trp Val Leu Lys Ala Phe Asp Ser Gln
                235                 240                 245
TGT CAG ATT CTT CTT ACA ACC AGA GAC AAG AGT GTT ACA GAT TCA GTA   1363
Cys Gln Ile Leu Leu Thr Thr Arg Asp Lys Ser Val Thr Asp Ser Val
            250                 255                 260
ATG GGT CCT AAA TAT GTA GTC CCT GTG GAG AGT TCC TTA GGA AAG GAA   1411
Met Gly Pro Lys Tyr Val Val Pro Val Glu Ser Ser Leu Gly Lys Glu
        265                 270                 275
AAA GGA CTT GAA ATT TTA TCC CTT TTT GTT AAT ATG AAG AAG GCA GAT   1459
Lys Gly Leu Glu Ile Leu Ser Leu Phe Val Asn Met Lys Lys Ala Asp
280                 285                 290
TTG CCA GAA CAA GCT CAT AGT ATT ATA AAA GAA TGT AAA GGC TCT CCC   1507
Leu Pro Glu Gln Ala His Ser Ile Ile Lys Glu Cys Lys Gly Ser Pro
295                 300                 305                 310
CTT GTA GTA TCT TTA ATT GGT GCA CTT TTA CGT GAT TTT CCC AAT CGC   1555
Leu Val Val Ser Leu Ile Gly Ala Leu Leu Arg Asp Phe Pro Asn Arg
                315                 320                 325
TGG GAG TAC TAC CTC AAA CAG CTT CAG AAT AAG CAG TTT AAG AGA ATA   1603
Trp Glu Tyr Tyr Leu Lys Gln Leu Gln Asn Lys Gln Phe Lys Arg Ile
            330                 335                 340
AGG AAA TCT TCG TCT TAT GAT TAT GAG GCT CTA GAT GAA GCC ATG TCT   1651
Arg Lys Ser Ser Ser Tyr Asp Tyr Glu Ala Leu Asp Glu Ala Met Ser
        345                 350                 355
ATA AGT GTT GAA ATG CTC AGA GAA GAC ATC AAA GAT TAT TAC ACA GAT   1699
Ile Ser Val Glu Met Leu Arg Glu Asp Ile Lys Asp Tyr Tyr Thr Asp
360                 365                 370
CTT TCC ATC CTT CAG AAG GAC GTT AAG GTG CCT ACA AAG GTG TTA TGT   1747
Leu Ser Ile Leu Gln Lys Asp Val Lys Val Pro Thr Lys Val Leu Cys
375                 380                 385                 390
ATT CTC TGG GAC ATG GAA ACT GAA GAA GTT GAA GAC ATA CTG CAG GAG   1795
Ile Leu Trp Asp Met Glu Thr Glu Glu Val Glu Asp Ile Leu Gln Glu
                395                 400                 405
```

*Fig. 19B*

```
TTT GTA AAT AAG TCT CTT TTA TTC TGT GAT CGG AAT GGA AAG TCG TTT          1843
Phe Val Asn Lys Ser Leu Leu Phe Cys Asp Arg Asn Gly Lys Ser Phe
            410                 415                 420
CGT TAT TAT TTA CAT GAT CTT CAA GTA GAT TTT CTT ACA GAG AAG AAT          1891
Arg Tyr Tyr Leu His Asp Leu Gln Val Asp Phe Leu Thr Glu Lys Asn
            425                 430                 435
TGC AGC CAG CTT CAG GAT CTA CAT AAG AAG ATA ATC ACT CAG TTT CAG          1939
Cys Ser Gln Leu Gln Asp Leu His Lys Lys Ile Ile Thr Gln Phe Gln
            440                 445                 450
AGA TAT CAC CAG CCG CAT ACT CTT TCA CCA GAT CAG GAA GAC TGT ATG          1987
Arg Tyr His Gln Pro His Thr Leu Ser Pro Asp Gln Glu Asp Cys Met
455                 460                 465                 470
TAT TGG TAC AAC TTT CTG GCC TAT CAC ATG GCC AGT GCC AAG ATG CAC          2035
Tyr Trp Tyr Asn Phe Leu Ala Tyr His Met Ala Ser Ala Lys Met His
                475                 480                 485
AAG GAA CTT TGT GCT TTA ATG TTT TCC CTG GAT TGG ATT AAA GCA AAA          2083
Lys Glu Leu Cys Ala Leu Met Phe Ser Leu Asp Trp Ile Lys Ala Lys
            490                 495                 500
ACA GAA CTT GTA GGC CCT GCT CAT CTG ATT CAT GAA TTT GTG GAA TAC          2131
Thr Glu Leu Val Gly Pro Ala His Leu Ile His Glu Phe Val Glu Tyr
            505                 510                 515
AGA CAT ATA CTA GAT GAA AAG GAT TGT GCA GTC AGT GAG AAT TTT CAG          2179
Arg His Ile Leu Asp Glu Lys Asp Cys Ala Val Ser Glu Asn Phe Gln
            520                 525                 530
GAG TTT TTA TCT TTA AAT GGA CAC CTT CTT GGA CGA CAG CCA TTT CCT          2227
Glu Phe Leu Ser Leu Asn Gly His Leu Leu Gly Arg Gln Pro Phe Pro
535                 540                 545                 550
AAT ATT GTA CAA CTG GGT CTC TGT GAG CCG GAA ACT TCA GAA GTT TAT          2275
Asn Ile Val Gln Leu Gly Leu Cys Glu Pro Glu Thr Ser Glu Val Tyr
                555                 560                 565
CAG CAA GCT AAG CTG CAG GCC AAG CAG GAG GTC GAT AAT GGA ATG CTT          2323
Gln Gln Ala Lys Leu Gln Ala Lys Gln Glu Val Asp Asn Gly Met Leu
            570                 575                 580
TAC CTG GAA TGG ATA AAC AAA AAA AAC ATC ACG AAT CTT TCC CGC TTA          2371
Tyr Leu Glu Trp Ile Asn Lys Lys Asn Ile Thr Asn Leu Ser Arg Leu
            585                 590                 595
GTT GTC CGC CCC CAC ACA GAT GCT GTT TAC CAT GCC TGC TTT TCT GAG          2419
Val Val Arg Pro His Thr Asp Ala Val Tyr His Ala Cys Phe Ser Glu
            600                 605                 610
GAT GGT CAG AGA ATA GCT TCT TGT GGA GCT GAT AAA ACC TTA CAG GTG          2467
Asp Gly Gln Arg Ile Ala Ser Cys Gly Ala Asp Lys Thr Leu Gln Val
615                 620                 625                 630
```

*Fig. 19C*

```
TTC AAA GCT GAA ACA GGA GAG AAA CTT CTA GAA ATC AAG GCT CAT GAG   2515
Phe Lys Ala Glu Thr Gly Glu Lys Leu Leu Glu Ile Lys Ala His Glu
                635                 640                 645
GAT GAA GTG CTT TGT TGT GCA TTC TCT ACA GAT GAC AGA TTT ATA GCA   2563
Asp Glu Val Leu Cys Cys Ala Phe Ser Thr Asp Asp Arg Phe Ile Ala
                650                 655                 660
ACC TGC TCA GTG GAT AAA AAA GTG AAG ATT TGG AAT TCT ATG ACT GGG   2611
Thr Cys Ser Val Asp Lys Lys Val Lys Ile Trp Asn Ser Met Thr Gly
                665                 670                 675
GAA CTA GTA CAC ACC TAT GAT GAG CAC TCA GAG CAA GTC AAT TGC TGC   2659
Glu Leu Val His Thr Tyr Asp Glu His Ser Glu Gln Val Asn Cys Cys
                680                 685                 690
CAT TTC ACC AAC AGT AGT CAT CAT CTT CTC TTA GCC ACT GGG TCA AGT   2707
His Phe Thr Asn Ser Ser His His Leu Leu Leu Ala Thr Gly Ser Ser
695                 700                 705                 710
GAC TGC TTC CTC AAA CTT TGG GAT TTG AAT CAA AAA GAA TGT CGA AAT   2755
Asp Cys Phe Leu Lys Leu Trp Asp Leu Asn Gln Lys Glu Cys Arg Asn
                715                 720                 725
ACC ATG TTT GGT CAT ACA AAT TCA GTC AAT CAC TGC AGA TTT TCA CCA   2803
Thr Met Phe Gly His Thr Asn Ser Val Asn His Cys Arg Phe Ser Pro
                730                 735                 740
GAT GAT AAG CTT TTG GCT AGT TGT TCA GCT GAT GGA ACC TTA AAG CTT   2851
Asp Asp Lys Leu Leu Ala Ser Cys Ser Ala Asp Gly Thr Leu Lys Leu
                745                 750                 755
TGG GAT GCG ACA TCA GCA AAT GAG AGG AAA AGC ATT AAT GTG AAA CAG   2899
Trp Asp Ala Thr Ser Ala Asn Glu Arg Lys Ser Ile Asn Val Lys Gln
                760                 765                 770
TTC TTC CTA AAT TTG GAG GAC CCT CAA GAG GAT ATG GAA GTG ATA GTG   2947
Phe Phe Leu Asn Leu Glu Asp Pro Gln Glu Asp Met Glu Val Ile Val
775                 780                 785                 790
AAG TGT TGT TCG TGG TCT GCT GAT GGT GCA AGG ATA ATG GTG GCA GCA   2995
Lys Cys Cys Ser Trp Ser Ala Asp Gly Ala Arg Ile Met Val Ala Ala
                795                 800                 805
AAA AAT AAA ATC TTT TTG TGG AAT ACA GAC TCA CGT TCA AAG GTG GCT   3043
Lys Asn Lys Ile Phe Leu Trp Asn Thr Asp Ser Arg Ser Lys Val Ala
                810                 815                 820
GAT TGC AGA GGA CAT TTA AGT TGG GTT CAT GGT GTG ATG TTT TCT CCT   3091
Asp Cys Arg Gly His Leu Ser Trp Val His Gly Val Met Phe Ser Pro
                825                 830                 835
GAT GGA TCA TCA TTT TTG ACA TCT TCT GAT GAC CAG ACA ATC AGG CTC   3139
Asp Gly Ser Ser Phe Leu Thr Ser Ser Asp Asp Gln Thr Ile Arg Leu
                840                 845                 850
```

*Fig. 19D*

```
TGG GAG ACA AAG AAA GTA TGT AAG AAC TCT GCT GTA ATG TTA AAG CAA     3187
Trp Glu Thr Lys Lys Val Cys Lys Asn Ser Ala Val Met Leu Lys Gln
855             860             865             870
GAA GTA GAT GTT GTG TTT CAA GAA AAT GAA GTG ATG GTC CTT GCA GTT     3235
Glu Val Asp Val Val Phe Gln Glu Asn Glu Val Met Val Leu Ala Val
                875             880             885
GAC CAT ATA AGA CGT CTG CAA CTC ATT AAT GGA AGA ACA GGT CAG ATT     3283
Asp His Ile Arg Arg Leu Gln Leu Ile Asn Gly Arg Thr Gly Gln Ile
            890             895             900
GAT TAT CTG ACT GAA GCT CAA GTT AGC TGC TGT TGC TTA AGT CCA CAT     3331
Asp Tyr Leu Thr Glu Ala Gln Val Ser Cys Cys Cys Leu Ser Pro His
        905             910             915
CTT CAG TAC ATT GCA TTT GGA GAT GAA AAT GGA GCC ATT GAG ATT TTA     3379
Leu Gln Tyr Ile Ala Phe Gly Asp Glu Asn Gly Ala Ile Glu Ile Leu
    920             925             930
GAA CTT GTA AAC AAT AGA ATC TTC CAG TCC AGG TTT CAG CAC AAG AAA     3427
Glu Leu Val Asn Asn Arg Ile Phe Gln Ser Arg Phe Gln His Lys Lys
935             940             945             950
ACT GTA TGG CAC ATC CAG TTC ACA GCC GAT GAG AAG ACT CTT ATT TCA     3475
Thr Val Trp His Ile Gln Phe Thr Ala Asp Glu Lys Thr Leu Ile Ser
                955             960             965
AGT TCT GAT GAT GCT GAA ATT CAG GTA TGG AAT TGG CAA TTG GAC AAA     3523
Ser Ser Asp Asp Ala Glu Ile Gln Val Trp Asn Trp Gln Leu Asp Lys
            970             975             980
TGT ATC TTT CTA CGA GGC CAT CAG GAA ACA GTG AAA GAC TTT AGA CTC     3571
Cys Ile Phe Leu Arg Gly His Gln Glu Thr Val Lys Asp Phe Arg Leu
        985             990             995
TTG AAA AAT TCA AGA CTG CTT TCT TGG TCA TTT GAT GGA ACA GTG AAG     3619
Leu Lys Asn Ser Arg Leu Leu Ser Trp Ser Phe Asp Gly Thr Val Lys
    1000            1005            1010
GTA TGG AAT ATT ATT ACT GGA AAT AAA GAA AAA GAC TTT GTC TGT CAC     3667
Val Trp Asn Ile Ile Thr Gly Asn Lys Glu Lys Asp Phe Val Cys His
1015            1020            1025            1030
CAG GGT ACA GTA CTT TCT TGT GAC ATT TCT CAC GAT GCT ACC AAG TTT     3715
Gln Gly Thr Val Leu Ser Cys Asp Ile Ser His Asp Ala Thr Lys Phe
                1035            1040            1045
TCA TCT ACC TCT GCT GAC AAG ACT GCA AAG ATC TGG AGT TTT GAT CTC     3763
Ser Ser Thr Ser Ala Asp Lys Thr Ala Lys Ile Trp Ser Phe Asp Leu
            1050            1055            1060
CTT TTG CCA CTT CAT GAA TTG AGG GGC CAC AAC GGC TGT GTG CGC TGC     3811
Leu Leu Pro Leu His Glu Leu Arg Gly His Asn Gly Cys Val Arg Cys
        1065            1070            1075
```

*Fig. 19E*

```
TCT GCC TTC TCT GTG GAC AGT ACC CTG CTG GCA ACG GGA GAT GAC AAT       3859
Ser Ala Phe Ser Val Asp Ser Thr Leu Leu Ala Thr Gly Asp Asp Asn
    1080            1085                1090
GGA GAA ATC AGG ATA TGG AAT GTC TCA AAC GGT GAG CTT CTT CAT TTG       3907
Gly Glu Ile Arg Ile Trp Asn Val Ser Asn Gly Glu Leu Leu His Leu
1095            1100                1105                    1110
TGT GCT CCG CTT TCA GAA GAA GGA GCT GCT ACC CAT GGA GGC TGG GTG       3955
Cys Ala Pro Leu Ser Glu Glu Gly Ala Ala Thr His Gly Gly Trp Val
                1115                1120                1125
ACT GAC CTT TGC TTT TCT CCA GAT GGC AAA ATG CTT ATC TCT GCT GGA       4003
Thr Asp Leu Cys Phe Ser Pro Asp Gly Lys Met Leu Ile Ser Ala Gly
                1130                1135                1140
GGA TAT ATT AAG TGG TGG AAC GTT GTC ACT GGG GAA TCC TCA CAG ACC       4051
Gly Tyr Ile Lys Trp Trp Asn Val Val Thr Gly Glu Ser Ser Gln Thr
        1145                1150                1155
TTC TAC ACA AAT GGA ACC AAT CTT AAG AAA ATA CAC GTG TCC CCT GAC       4099
Phe Tyr Thr Asn Gly Thr Asn Leu Lys Lys Ile His Val Ser Pro Asp
    1160                1165                1170
TTC AAA ACA TAT GTG ACT GTG GAT AAT CTT GGT ATT TTA TAT ATT TTA       4147
Phe Lys Thr Tyr Val Thr Val Asp Asn Leu Gly Ile Leu Tyr Ile Leu
1175            1180                1185                    1190
CAG ACT TTA GAA TAAAATAGTTAAG CATTAATGTA GTTGAACTTT TTAAATTTTT        4202
Gln Thr Leu Glu
```

```
GAATTGGAAA AAAATTCTAA TGAAACCCTG ATATCAACTT TTTATAAAGC TCTTAATTGT     4262
TGTGCAGTAT TGCATTCATT ACAAAAGTGT TTGTGGTTGG ATGAATAATA TTAATGTAGC     4322
TTTTTCCCAA ATGAACATAC CTTTAATCTT GTTTTTCATG ATCATCATTA ACAGTTTGTC     4382
CTTAGGATGC AAATGAAAAT GTGAATACAT ACCTTGTTGT ACTGTTGGTA AAATTCTGTC     4442
TTGATGCATT CAAAATGGTT GACATAATTA ATGAGAAGAA TTTGGAAGAA ATTGGTATTT     4502
TAATACTGTC TGTATTTATT ACTGTTATGC AGGCTGTGCC TCAGGGTAGC AGTGGCCTGC     4562
TTTTTGAACC ACACTTACCC CAAGGGGGTT TTGTTCTCCT AAATACAATC TTAGAGGTTT     4622
TTTGCACTCT TTAAATTTGC TTTAAAAATA TTGTGTCTGT GTGCATAGTC TGCAGCATTT     4682
CCTTTAATTG ACTCAATAAG TGAGTCTTGG ATTTAGCAGG CCCCCCCACC TTTTTTTTTT     4742
GTTTTTGGAG ACAGAGTCTT GCTTTGTTGC CAGGCTGGAG TGCAGTGGCG CGATCTCGGC     4802
TCACCACAAT CGCTGCCTCC TGGGTTCAAG CAATTCTCCT GCCTCAGCCT CCCGAGTAGC     4862
TGGGACTACA GGTGTGCGCA CATGCCAGGC TAATTTTTGT ATTTTTAGTA GAGACGGGGT     4922
TTCACCATGT TGGCCGGGAT GGTCTCGATC TCTTGACCTC ATGATCTACC CGCCTTGGCC     4982
TCCCAAAGTG CTGAGATTAC AGGCGTGAGC CACCGTGCCT GGCCAGGCCC CTTCTCTTTT     5042
AATGGAGACA GGGTCTTGCA CTATCACCCA GGCTGGAGTG CAGTGGCATA ATCATACCTC     5102
ATTGCAGCCT CAGACTCCTG GGTTCAAGCA ATCCTCCTGC CTCAGCCTCC CAAGTAGCTG     5162
AGACTGCAGG CACGAGCCAC CACACCCAGC TAATTTTTAA GTTTTCTTGT AGAGACAGGG     5222
TCTCACTATG TTGTCTAGGC TGGTCTTGAA CTCTTGGCCT CAAGTAATCC TCCTGCCTCA     5282
GCCTCCCAAA GTGTTGGGAT TGCAGATATG AGCCACTGGC CTGGCCTTCA GCAGTTCTTT     5342
TTGTGAAGTA AAACTTGTAT GTTGGAAAGA GTAGATTTTA TTGGTCTACC CTTTTCTCAC     5402
TGTAGCTGCT GGCAGCCCTG TGCCATATCT GGACTCTAGT TGTCAGTATC TGAGTTGGAC     5462
ACTATTCCTG CTCCCTCTTG TTTCTTACAT ATCAGACTTC TTACTTGAAT GAAACCTGAT     5522
CTTTCCTAAT CCTCACTTTT TTCTTTTTTA AAAAGCAGTT TCTCCACTGC TAAATGTTAG     5582
TCATTGAGGT GGGGCCAATT TTAATCATAA GCCTTAATAA GATTTTTCTA AGAAATGTGA     5642
AATAGAACAA TTTTCATCTA ATTCCATTTA CTTTTAGATG AATGGCATTG TGAATGCCAT     5702
TCTTTTAATG AATTTCAAGA GAATTCTCTG GTTTTCTGTG TAATTCCAGA TGAGTCACTG     5762
```

*Fig. 19F*

```
TAACTCTAGA AGATTAACCT TCCAGCCAAC CTATTTTCCT TTCCCTTGTC TCTCTCATCC    5822
TCTTTTCCTT CCTTCTTTCC TTTCTCTTCT TTTATCTCCA AGGTTAATCA GGAAAAATAG    5882
CTTTTGACAG GGGAAAAAAC TCAATAACTA GCTATTTTTG ACCTCCTGAT CAGGAACTTT    5942
AGTTGAAGCG TAAATCTAAA GAAACATTTT CTCTGAAATA TATTATTAAG GGCAATGGAG    6002
ATAAATTAAT AGTAGATGTG GTTCCCAGAA AATATAATCA AAATTCAAAG ATTTTTTTTG    6062
TTTCTGTAAC TGGAACTAAA TCAAATGATT ACTAGTGTTA ATAGTAGATA ACTTGTTTTT    6122
ATTGTTGGTG CATATTAGTA TAACTGTGGG GTAGGTCGGG GAGAGGGTAA GGGAATAGAT    6182
CACTCAGATG TATTTTAGAT AAGCTATTTA GCCTTTGATG GAATCATAAA TACAGTGAAT    6242
ACAATCCTTT GCATTGTTAA GGAGGTTTTT TGTTTTTAAA TGGTGGGTCA AGGAGCTAGT    6302
TTACAGGCTT ACTGTGATTT AAGCAAATGT GAAAAGTGAA ACCTTAATTT TATCAAAAGA    6362
AATTTCTGTA AATGGTATGT CTCCTTAGAA TACCCAAATC ATAATTTTAT TTGTACACAC    6422
TGTTAGGGGC TCATCTCATG TAGGCAGAGT ATAAAGTATT ACCTTTTGGA ATTAAAAGCC    6482
ACTGACTGTT ATAAAGTATA ACAACACACA TCAGGTTTTA AAAAGCCTTG AATGGCCCTT    6542
GTCTTAAAAA GAAATTAGGA GCCAGGTGCG GTGGCACGTG CCTGTAGTCC CAGCTCCTTG    6602
GGAGGCTGAG ACAGGAGGAT TCCTTGAGCC CTGGAGTTTG AGTCCAGCCT GGGTGACATA    6662
GCAAGACCCT GTCTTAAAAG AAAAATGGGA AGAAAGACAA GGTAACATGA AGAAAGAAGA    6722
GATACCTAGT ATGATGGAGC TGCAAATTTC ATGGCAGTTC ATGCAGTCGG TCAAGAGGAG    6782
GATTTTGTTT TGTAGTTTGC AGATGAGCAT TTCTAAAGCA TTTTCCCTTG CTGTATTTTT    6842
TTGTATTATA AATTACATTG GACTTCATAT ATATAATTTT TTTTTACATT ATATGTCTCT    6902
TGTATGTTTT GAAACTCTTG TATTTATGAT ATAGCTTATA TGATTTTTTT GCCTTGGTAT    6962
ACATTTTAAA ATATGAATTT AAAAAATTTT TGTAAAAATA AAATTCACAA AATTGTTTTG    7022
AAAAACAAAA AAAAAAAAAA                                                7042
```

*Fig. 19G*

```
   1  gccatggacg aagcggatcg gcggctcctg cggcggtgcc ggctgcggct ggtggaagag
  61  ctgcaggtgg accagctctg ggacgtcctg ctgagccgcg agctgttcag gccccatatg
 121  atcgaggaca tccagcgggc aggctctgga tctcggcggg atcaggccag gcagctgatc
 181  atagatctgg agactcgagg gagtcaggct cttcctttgt tcatctcctg cttagaggac
 241  acaggccagg acatgctggc ttcgtttctg cgaactaaca ggcaagcagg aaagttgtcg
 301  aagccaaccc tagaaaacct taccccagtg gtgctcagac cagagattcg caaaccagag
 361  gttctcagac cggaaacacc cagaccagtg gacattggtt ctggaggatt cggtgatgtc
 421  ggtgctcttg agagtttgag gggaaatgca gatttggctt acatcctgag catggagccc
 481  tgtggccact gcctcattat caacaatgtg aacttctgcc gtgagtccgg gctccgcacc
 541  cgcactggct ccaacatcga ctgtgagaag ttgcggcgtc gcttctcctc gctgcatttc
 601  atggtggagg tgaagggcga cctgactgcc aagaaaatgg tgctggcttt gctggagctg
 661  gcgcggcagg accacggtgc tctggactgc tgcgtggtgg tcattctctc tcacggctgt
 721  caggccagcc acctgcagtt cccaggggct gtctacggca cagatggatg ccctgtgtcg
 781  gtcgagaaga ttgtgaacat cttcaatggg accagctgcc ccagcctggg agggaagccc
 841  aagctctttt catccaggc ctgtggtggg gagcagaaag accatgggtt tgaggtggcc
 901  tccacttccc ctgaagacga gtccctggc agtaaccccg agccagatgc caccccgttc
 961  caggaaggtt tgaggacctt cgaccagctg gacgccatat ctagtttgcc cacacccagt
1021  gacatctttg tgtcctactc tactttccca ggttttgttt cctggaggga ccccaagagt
1081  ggctcctggt acgttgagac cctggacgac atctttgagc agtgggctca ctctgaagac
1141  ctgcagtccc tcctgcttag ggtcgctaat gctgtttcgg tgaaagggat ttataaacag
1201  atgcctggtt gctttaattt cctccggaaa aaactttcct ttaaaacatc ataaggccag
1261  ggcccctcac cctgccttat cttgcacccc caaagctttc ctgccccagg cctgaaagag
1321  gctgaggcct ggactttcct gcaactcaag gactttgcag ccggcacagg gtctgctctt
1381  tctctgccag tgacagacag gctcttagca gcttccagat tgacgacaag tgctgaacag
1441  tggaggaaga gggacagatg aatgccgtgg attgcacgtg g
```

*Fig. 20*

SEQUENCE LISTING

```
<160> NUMBER OF SEQ ID NOS: 15

<210> SEQ ID NO 1
<211> LENGTH: 7042
<212> TYPE: DNA
<213> ORGANISM: Homo sapien
<220> FEATURE:
<221> NAME/KEY: CDS
<222> LOCATION: (578)...(4159)

<400> SEQUENCE: 1
aagaagaggt agcgagtgga cgtgactgct ctatcccggg caaaagggat agaaccagag      60
gtggggagtc tgggcagtcg gcgacccgcg aagacttgag gtgccgcagc ggcatccgga     120
gtagcgccgg gctccctccg gggtgcagcc gccgtcgggg gaagggcgcc acaggccggg     180
aagacctcct ccctttgtgt ccagtagtgg ggtccaccgg agggcggccc gtgggccggg     240
cctcaccgcg gcgctccggg actgtggggt caggctgcgt tgggtggacg cccacctcgc     300
caaccttcgg aggtccctgg gggtcttcgt gcgcccgggg gctgcagaga tccaggggag     360
gcgcctgtga ggcccggacc tgccccgggg cgaagggtat gtggcgagac agagccctgc     420
acccctaatt cccggtggaa aactcctgtt gccgtttccc tccaccggcc tggagtctcc     480
cagtcttgtc ccggcagtgc cgccctcccc actaagacct aggcgcaaag gcttggctca     540
tggttgacag ctcagagaga gaaagatctg agggaag atg gat gca aaa gct cga     595
                                           Met Asp Ala Lys Ala Arg
                                           1               5
```

| | |
|---|---|
| aat tgt ttg ctt caa cat aga gaa gct ctg gaa aag gac atc aag aca<br>Asn Cys Leu Leu Gln His Arg Glu Ala Leu Glu Lys Asp Ile Lys Thr<br>          10                    15                  20 | 643 |
| tcc tac atc atg gat cac atg att agt gat gga ttt tta aca ata tca<br>Ser Tyr Ile Met Asp His Met Ile Ser Asp Gly Phe Leu Thr Ile Ser<br>          25                    30                  35 | 691 |
| gaa gag gaa aaa gta aga aat gag ccc act caa cag caa aga gca gct<br>Glu Glu Glu Lys Val Arg Asn Glu Pro Thr Gln Gln Gln Arg Ala Ala<br>40                    45                    50 | 739 |
| atg ctg att aaa atg ata ctt aaa aaa gat aat gat tcc tac gta tca<br>Met Leu Ile Lys Met Ile Leu Lys Lys Asp Asn Asp Ser Tyr Val Ser<br>55                    60                    65                  70 | 787 |
| ttc tac aat gct cta cta cat gaa gga tat aaa gat ctt gct gcc ctt<br>Phe Tyr Asn Ala Leu Leu His Glu Gly Tyr Lys Asp Leu Ala Ala Leu<br>          75                    80                  85 | 835 |
| ctc cat gat ggc att cct gtt gtc tct tct tcc agt gta agg aca gtc<br>Leu His Asp Gly Ile Pro Val Val Ser Ser Ser Ser Val Arg Thr Val<br>                  90                    95                  100 | 883 |
| ctg tgt gaa ggt gga gta cca cag agg cca gtt gtt ttt gtc aca agg<br>Leu Cys Glu Gly Gly Val Pro Gln Arg Pro Val Val Phe Val Thr Arg<br>          105                    110                  115 | 931 |
| aag aag ctg gtg aat gca att cag cag aag ctc tcc aaa ttg aaa ggt<br>Lys Lys Leu Val Asn Ala Ile Gln Gln Lys Leu Ser Lys Leu Lys Gly<br>120                    125                    130 | 979 |
| gaa cca gga tgg gtc acc ata cat gga atg gca ggc tgt ggg aag tct<br>Glu Pro Gly Trp Val Thr Ile His Gly Met Ala Gly Cys Gly Lys Ser<br>135                    140                    145                  150 | 1027 |
| gta tta gct gca gaa gct gtt aga gat cat tcc ctt tta gaa ggt tgt<br>Val Leu Ala Ala Glu Ala Val Arg Asp His Ser Leu Leu Glu Gly Cys<br>                  155                    160                  165 | 1075 |
| ttc cca ggg gga gtg cat tgg gtt tca gtt ggg aaa caa gac aaa tct<br>Phe Pro Gly Gly Val His Trp Val Ser Val Gly Lys Gln Asp Lys Ser<br>          170                    175                  180 | 1123 |
| ggg ctt ctg atg aaa ctg cag aat ctt tgc aca cgg ttg gat cag gat<br>Gly Leu Leu Met Lys Leu Gln Asn Leu Cys Thr Arg Leu Asp Gln Asp<br>185                    190                    195 | 1171 |
| gag agt ttt tcc cag agg ctt cca ctt aat att gaa gag gct aaa gac<br>Glu Ser Phe Ser Gln Arg Leu Pro Leu Asn Ile Glu Glu Ala Lys Asp<br>200                    205                    210 | 1219 |
| cgt ctc cgc att ctg atg ctt cgc aaa cac cca agg tct ctc ttg atc<br>Arg Leu Arg Ile Leu Met Leu Arg Lys His Pro Arg Ser Leu Leu Ile<br>215                    220                    225                  230 | 1267 |
| ttg gat gat gtt tgg gac tct tgg gtg ttg aaa gct ttt gac agt cag<br>Leu Asp Asp Val Trp Asp Ser Trp Val Leu Lys Ala Phe Asp Ser Gln<br>                  235                    240                  245 | 1315 |
| tgt cag att ctt ctt aca acc aga gac aag agt gtt aca gat tca gta<br>Cys Gln Ile Leu Leu Thr Thr Arg Asp Lys Ser Val Thr Asp Ser Val<br>          250                    255                  260 | 1363 |
| atg ggt cct aaa tat gta gtc cct gtg gag agt tcc tta gga aag gaa<br>Met Gly Pro Lys Tyr Val Val Pro Val Glu Ser Ser Leu Gly Lys Glu<br>265                    270                    275 | 1411 |
| aaa gga ctt gaa att tta tcc ctt ttt gtt aat atg aag aag gca gat<br>Lys Gly Leu Glu Ile Leu Ser Leu Phe Val Asn Met Lys Lys Ala Asp<br>280                    285                    290 | 1459 |
| ttg cca gaa caa gct cat agt att ata aaa gaa tgt aaa ggc tct ccc<br>Leu Pro Glu Gln Ala His Ser Ile Ile Lys Glu Cys Lys Gly Ser Pro<br>295                    300                    305                  310 | 1507 |
| ctt gta gta tct tta att ggt gca ctt tta cgt gat ttt ccc aat cgc<br>Leu Val Val Ser Leu Ile Gly Ala Leu Leu Arg Asp Phe Pro Asn Arg<br>          315                    320                  325 | 1555 |

-continued

```
tgg gag tac tac ctc aaa cag ctt cag aat aag cag ttt aag aga ata    1603
Trp Glu Tyr Tyr Leu Lys Gln Leu Gln Asn Lys Gln Phe Lys Arg Ile
            330                 335                 340 agg aaa tct tcg tct tat gat tat gag gct cta gat gaa gcc atg tct    1651
Arg Lys Ser Ser Ser Tyr Asp Tyr Glu Ala Leu Asp Glu Ala Met Ser
        345                 350                 355 ata agt gtt gaa atg ctc aga gaa gac atc aaa gat tat tac aca gat    1699
Ile Ser Val Glu Met Leu Arg Glu Asp Ile Lys Asp Tyr Tyr Thr Asp
    360                 365                 370 ctt tcc atc ctt cag aag gac gtt aag gtg cct aca aag gtg tta tgt    1747
Leu Ser Ile Leu Gln Lys Asp Val Lys Val Pro Thr Lys Val Leu Cys
375                 380                 385                 390 att ctc tgg gac atg gaa act gaa gaa gtt gaa gac ata ctg cag gag    1795
Ile Leu Trp Asp Met Glu Thr Glu Glu Val Glu Asp Ile Leu Gln Glu
                395                 400                 405 ttt gta aat aag tct ctt tta ttc tgt gat cgg aat gga aag tcg ttt    1843
Phe Val Asn Lys Ser Leu Leu Phe Cys Asp Arg Asn Gly Lys Ser Phe
            410                 415                 420 cgt tat tat tta cat gat ctt caa gta gat ttt ctt aca gag aag aat    1891
Arg Tyr Tyr Leu His Asp Leu Gln Val Asp Phe Leu Thr Glu Lys Asn
        425                 430                 435 tgc agc cag ctt cag gat cta cat aag aag ata atc act cag ttt cag    1939
Cys Ser Gln Leu Gln Asp Leu His Lys Lys Ile Ile Thr Gln Phe Gln
    440                 445                 450 aga tat cac cag ccg cat act ctt tca cca gat cag gaa gac tgt atg    1987
Arg Tyr His Gln Pro His Thr Leu Ser Pro Asp Gln Glu Asp Cys Met
455                 460                 465                 470 tat tgg tac aac ttt ctg gcc tat cac atg gcc agt gcc aag atg cac    2035
Tyr Trp Tyr Asn Phe Leu Ala Tyr His Met Ala Ser Ala Lys Met His
                475                 480                 485 aag gaa ctt tgt gct tta atg ttt tcc ctg gat tgg att aaa gca aaa    2083
Lys Glu Leu Cys Ala Leu Met Phe Ser Leu Asp Trp Ile Lys Ala Lys
            490                 495                 500 aca gaa ctt gta ggc cct gct cat ctg att cat gaa ttt gtg gaa tac    2131
Thr Glu Leu Val Gly Pro Ala His Leu Ile His Glu Phe Val Glu Tyr
        505                 510                 515 aga cat ata cta gat gaa aag gat tgt gca gtc agt gag aat ttt cag    2179
Arg His Ile Leu Asp Glu Lys Asp Cys Ala Val Ser Glu Asn Phe Gln
    520                 525                 530 gag ttt tta tct tta aat gga cac ctt ctt gga cga cag cca ttt cct    2227
Glu Phe Leu Ser Leu Asn Gly His Leu Leu Gly Arg Gln Pro Phe Pro
535                 540                 545                 550 aat att gta caa ctg ggt ctc tgt gag ccg gaa act tca gaa gtt tat    2275
Asn Ile Val Gln Leu Gly Leu Cys Glu Pro Glu Thr Ser Glu Val Tyr
                555                 560                 565 cag caa gct aag ctg cag gcc aag cag gag gtc gat aat gga atg ctt    2323
Gln Gln Ala Lys Leu Gln Ala Lys Gln Glu Val Asp Asn Gly Met Leu
            570                 575                 580 tac ctg gaa tgg ata aac aaa aaa aac atc acg aat ctt tcc cgc tta    2371
Tyr Leu Glu Trp Ile Asn Lys Lys Asn Ile Thr Asn Leu Ser Arg Leu
        585                 590                 595 gtt gtc cgc ccc cac aca gat gct gtt tac cat gcc tgc ttt tct gag    2419
Val Val Arg Pro His Thr Asp Ala Val Tyr His Ala Cys Phe Ser Glu
    600                 605                 610 gat ggt cag aga ata gct tct tgt gga gct gat aaa acc tta cag gtg    2467
Asp Gly Gln Arg Ile Ala Ser Cys Gly Ala Asp Lys Thr Leu Gln Val
615                 620                 625                 630 ttc aaa gct gaa aca gga gag aaa ctt cta gaa atc aag gct cat gag    2515
Phe Lys Ala Glu Thr Gly Glu Lys Leu Leu Glu Ile Lys Ala His Glu
```

-continued

```
                635                 640                 645
gat gaa gtg ctt tgt tgt gca ttc tct aca gat gac aga ttt ata gca      2563
Asp Glu Val Leu Cys Cys Ala Phe Ser Thr Asp Asp Arg Phe Ile Ala
            650                 655                 660 acc tgc tca gtg gat aaa aaa gtg aag att tgg aat tct atg act ggg      2611
Thr Cys Ser Val Asp Lys Lys Val Lys Ile Trp Asn Ser Met Thr Gly
        665                 670                 675 gaa cta gta cac acc tat gat gag cac tca gag caa gtc aat tgc tgc      2659
Glu Leu Val His Thr Tyr Asp Glu His Ser Glu Gln Val Asn Cys Cys
    680                 685                 690 cat ttc acc aac agt agt cat cat ctt ctc tta gcc act ggg tca agt      2707
His Phe Thr Asn Ser Ser His His Leu Leu Leu Ala Thr Gly Ser Ser
695                 700                 705                 710 gac tgc ttc ctc aaa ctt tgg gat ttg aat caa aaa gaa tgt cga aat      2755
Asp Cys Phe Leu Lys Leu Trp Asp Leu Asn Gln Lys Glu Cys Arg Asn
                715                 720                 725 acc atg ttt ggt cat aca aat tca gtc aat cac tgc aga ttt tca cca      2803
Thr Met Phe Gly His Thr Asn Ser Val Asn His Cys Arg Phe Ser Pro
            730                 735                 740 gat gat aag ctt ttg gct agt tgt tca gct gat gga acc tta aag ctt      2851
Asp Asp Lys Leu Leu Ala Ser Cys Ser Ala Asp Gly Thr Leu Lys Leu
        745                 750                 755 tgg gat gcg aca tca gca aat gag agg aaa agc att aat gtg aaa cag      2899
Trp Asp Ala Thr Ser Ala Asn Glu Arg Lys Ser Ile Asn Val Lys Gln
    760                 765                 770 ttc ttc cta aat ttg gag gac cct caa gag gat atg gaa gtg ata gtg      2947
Phe Phe Leu Asn Leu Glu Asp Pro Gln Glu Asp Met Glu Val Ile Val
775                 780                 785                 790 aag tgt tgt tcg tgg tct gct gat ggt gca agg ata atg gtg gca gca      2995
Lys Cys Cys Ser Trp Ser Ala Asp Gly Ala Arg Ile Met Val Ala Ala
                795                 800                 805 aaa aat aaa atc ttt ttg tgg aat aca gac tca cgt tca aag gtg gct      3043
Lys Asn Lys Ile Phe Leu Trp Asn Thr Asp Ser Arg Ser Lys Val Ala
            810                 815                 820 gat tgc aga gga cat tta agt tgg gtt cat ggt gtg atg ttt tct cct      3091
Asp Cys Arg Gly His Leu Ser Trp Val His Gly Val Met Phe Ser Pro
        825                 830                 835 gat gga tca tca ttt ttg aca tct tct gat gac cag aca atc agg ctc      3139
Asp Gly Ser Ser Phe Leu Thr Ser Ser Asp Asp Gln Thr Ile Arg Leu
    840                 845                 850 tgg gag aca aag aaa gta tgt aag aac tct gct gta atg tta aag caa      3187
Trp Glu Thr Lys Lys Val Cys Lys Asn Ser Ala Val Met Leu Lys Gln
855                 860                 865                 870 gaa gta gat gtt gtg ttt caa gaa aat gaa gtg atg gtc ctt gca gtt      3235
Glu Val Asp Val Val Phe Gln Glu Asn Glu Val Met Val Leu Ala Val
                875                 880                 885 gac cat ata aga cgt ctg caa ctc att aat gga aga aca ggt cag att      3283
Asp His Ile Arg Arg Leu Gln Leu Ile Asn Gly Arg Thr Gly Gln Ile
            890                 895                 900 gat tat ctg act gaa gct caa gtt agc tgc tgt tgc tta agt cca cat      3331
Asp Tyr Leu Thr Glu Ala Gln Val Ser Cys Cys Cys Leu Ser Pro His
        905                 910                 915 ctt cag tac att gca ttt gga gat gaa aat gga gcc att gag att tta      3379
Leu Gln Tyr Ile Ala Phe Gly Asp Glu Asn Gly Ala Ile Glu Ile Leu
    920                 925                 930 gaa ctt gta aac aat aga atc ttc cag tcc agg ttt cag cac aag aaa      3427
Glu Leu Val Asn Asn Arg Ile Phe Gln Ser Arg Phe Gln His Lys Lys
935                 940                 945                 950 act gta tgg cac atc cag ttc aca gcc gat gag aag act ctt att tca      3475
```

-continued

| | | |
|---|---|---|
| Thr Val Trp His Ile Gln Phe Thr Ala Asp Glu Lys Thr Leu Ile Ser<br>955 960 965 | | |
| agt tct gat gat gct gaa att cag gta tgg aat tgg caa ttg gac aaa<br>Ser Ser Asp Asp Ala Glu Ile Gln Val Trp Asn Trp Gln Leu Asp Lys<br>970 975 980 | 3523 | |
| tgt atc ttt cta cga ggc cat cag gaa aca gtg aaa gac ttt aga ctc<br>Cys Ile Phe Leu Arg Gly His Gln Glu Thr Val Lys Asp Phe Arg Leu<br>985 990 995 | 3571 | |
| ttg aaa aat tca aga ctg ctt tct tgg tca ttt gat gga aca gtg aag<br>Leu Lys Asn Ser Arg Leu Leu Ser Trp Ser Phe Asp Gly Thr Val Lys<br>1000 1005 1010 | 3619 | |
| gta tgg aat att att act gga aat aaa gaa aaa gac ttt gtc tgt cac<br>Val Trp Asn Ile Ile Thr Gly Asn Lys Glu Lys Asp Phe Val Cys His<br>1015 1020 1025 1030 | 3667 | |
| cag ggt aca gta ctt tct tgt gac att tct cac gat gct acc aag ttt<br>Gln Gly Thr Val Leu Ser Cys Asp Ile Ser His Asp Ala Thr Lys Phe<br>1035 1040 1045 | 3715 | |
| tca tct acc tct gct gac aag act gca aag atc tgg agt ttt gat ctc<br>Ser Ser Thr Ser Ala Asp Lys Thr Ala Lys Ile Trp Ser Phe Asp Leu<br>1050 1055 1060 | 3763 | |
| ctt ttg cca ctt cat gaa ttg agg ggc cac aac ggc tgt gtg cgc tgc<br>Leu Leu Pro Leu His Glu Leu Arg Gly His Asn Gly Cys Val Arg Cys<br>1065 1070 1075 | 3811 | |
| tct gcc ttc tct gtg gac agt acc ctg ctg gca acg gga gat gac aat<br>Ser Ala Phe Ser Val Asp Ser Thr Leu Leu Ala Thr Gly Asp Asp Asn<br>1080 1085 1090 | 3859 | |
| gga gaa atc agg ata tgg aat gtc tca aac ggt gag ctt ctt cat ttg<br>Gly Glu Ile Arg Ile Trp Asn Val Ser Asn Gly Glu Leu Leu His Leu<br>1095 1100 1105 1110 | 3907 | |
| tgt gct ccg ctt tca gaa gaa gga gct gct acc cat gga ggc tgg gtg<br>Cys Ala Pro Leu Ser Glu Glu Gly Ala Ala Thr His Gly Gly Trp Val<br>1115 1120 1125 | 3955 | |
| act gac ctt tgc ttt tct cca gat ggc aaa atg ctt atc tct gct gga<br>Thr Asp Leu Cys Phe Ser Pro Asp Gly Lys Met Leu Ile Ser Ala Gly<br>1130 1135 1140 | 4003 | |
| gga tat att aag tgg tgg aac gtt gtc act ggg gaa tcc tca cag acc<br>Gly Tyr Ile Lys Trp Trp Asn Val Val Thr Gly Glu Ser Ser Gln Thr<br>1145 1150 1155 | 4051 | |
| ttc tac aca aat gga acc aat ctt aag aaa ata cac gtg tcc cct gac<br>Phe Tyr Thr Asn Gly Thr Asn Leu Lys Lys Ile His Val Ser Pro Asp<br>1160 1165 1170 | 4099 | |
| ttc aaa aca tat gtg act gtg gat aat ctt ggt att tta tat att tta<br>Phe Lys Thr Tyr Val Thr Val Asp Asn Leu Gly Ile Leu Tyr Ile Leu<br>1175 1180 1185 1190 | 4147 | |
| cag act tta gaa taaaatagtt aagcattaat gtagttgaac tttttaaatt<br>Gln Thr Leu Glu | 4199 | |
| tttgaattgg aaaaaaattc taatgaaacc ctgatatcaa cttttttataa agctcttaat | 4259 | |
| tgttgtgcag tattgcattc attacaaaag tgtttgtggt tggatgaata atattaatgt | 4319 | |
| agctttttcc caaatgaaca tacctttaat cttgttttc atgatcatca ttaacagttt | 4379 | |
| gtccttagga tgcaaatgaa aatgtgaata catacctgt tgtactgttg gtaaaattct | 4439 | |
| gtcttgatgc attcaaaatg gttgacataa ttaatgagaa gaatttggaa gaaattggta | 4499 | |
| ttttaatact gtctgtattt attactgtta tgcaggctgt gcctcagggt agcagtggcc | 4559 | |
| tgcttttga accacactta ccccaagggg gttttgttct cctaaataca atcttagagg | 4619 | |
| ttttttgcac tctttaaatt tgctttaaaa atattgtgtc tgtgtgcata gtctgcagca | 4679 | |
| tttcctttaa ttgactcaat aagtgagtct tggatttagc aggcccccc acctttttt | 4739 | |

-continued

```
tttgtttttg gagacagagt cttgctttgt tgccaggctg gagtgcagtg gcgcgatctc    4799
ggctcaccac aatcgctgcc tcctgggttc aagcaattct cctgcctcag cctcccgagt    4859
agctgggact acaggtgtgc gcacatgcca ggctaatttt tgtattttta gtagagacgg    4919
ggtttcacca tgttggccgg gatggtctcg atctcttgac ctcatgatct acccgccttg    4979
gcctcccaaa gtgctgagat tacaggcgtg agccaccgtg cctggccagg ccccttctct    5039
tttaatggag acagggtctt gcactatcac ccaggctgga gtgcagtggc ataatcatac    5099
ctcattgcag cctcagactc ctgggttcaa gcaatcctcc tgcctcagcc tcccaagtag    5159
ctgagactgc aggcacgagc caccacaccc agctaatttt taagttttct tgtagagaca    5219
gggtctcact atgttgtcta ggctggtctt gaactcttgg cctcaagtaa tcctcctgcc    5279
tcagcctccc aaagtgttgg gattgcagat atgagccact ggcctggcct tcagcagttc    5339
tttttgtgaa gtaaaacttg tatgttggaa agagtagatt ttattggtct acccttttct    5399
cactgtagct gctggcagcc ctgtgccata tctggactct agttgtcagt atctgagttg    5459
gacactattc ctgctccctc ttgtttctta catatcagac ttcttacttg aatgaaacct    5519
gatctttcct aatcctcact tttttctttt ttaaaaagca gtttctccac tgctaaatgt    5579
tagtcattga ggtggggcca attttaatca taagccttaa taagattttt ctaagaaatg    5639
tgaaatagaa caattttcat ctaattccat ttactttag atgaatggca ttgtgaatgc     5699
cattctttta atgaatttca agagaattct ctggttttct gtgtaattcc agatgagtca    5759
ctgtaactct agaagattaa ccttccagcc aacctatttt cctttccctt gtctctctca    5819
tcctcttttc cttccttctt tcctttctct tcttttatct ccaaggttaa tcaggaaaaa    5879
tagcttttga caggggaaaa aactcaataa ctagctattt ttgacctcct gatcaggaac    5939
tttagttgaa gcgtaaatct aaagaaacat tttctctgaa atatattatt aagggcaatg    5999
gagataaatt aatagtagat gtggttccca gaaaatataa tcaaaattca aagatttttt    6059
ttgtttctgt aactggaact aaatcaaatg attactagtg ttaatagtag ataacttgtt    6119
tttattgttg gtgcatatta gtataactgt ggggtaggtc ggggagaggg taagggaata    6179
gatcactcag atgtattta gataagctat ttagcctttg atggaatcat aaatacagtg     6239
aatacaatcc tttgcattgt taaggaggtt ttttgttttt aaatggtggg tcaaggagct    6299
agtttacagg cttactgtga tttaagcaaa tgtgaaaagt gaaaccttaa ttttatcaaa    6359
agaaatttct gtaaatggta tgtctcctta gaatacccaa atcataattt tatttgtaca    6419
cactgttagg ggctcatctc atgtaggcag agtataaagt attacctttt ggaattaaaa    6479
gccactgact gttataaagt ataacaacac acatcaggtt ttaaaaagcc ttgaatggcc    6539
cttgtcttaa aaagaaatta ggagccaggt gcggtggcac gtgcctgtag tcccagctcc    6599
tgggaggct gagacaggag gattccttga gccctggagt ttgagtccag cctgggtgac     6659
atagcaagac cctgtcttaa aagaaaaatg ggaagaaaga caaggtaaca tgaagaaaga    6719
agagatacct agtatgatgg agctgcaaat ttcatggcag ttcatgcagt cggtcaagag    6779
gaggattttg ttttgtagtt tgcagatgag catttctaaa gcattttccc ttgctgtatt    6839
tttttgtatt ataaattaca ttggacttca tatatataat tttttttac attatatgtc     6899
tcttgtatgt tttgaaactc ttgtatttat gatatagctt atatgatttt tttgccttgg    6959
tatacatttt aaaatatgaa tttaaaaaat ttttgtaaaa ataaaattca caaaattgtt    7019
ttgaaaaaca aaaaaaaaaa aaa                                            7042
```

-continued

```
<210> SEQ ID NO 2
<211> LENGTH: 1194
<212> TYPE: PRT
<213> ORGANISM: Homo sapien

<400> SEQUENCE: 2

Met Asp Ala Lys Ala Arg Asn Cys Leu Leu Gln His Arg Glu Ala Leu
 1               5                  10                  15

Glu Lys Asp Ile Lys Thr Ser Tyr Ile Met Asp His Met Ile Ser Asp
             20                  25                  30

Gly Phe Leu Thr Ile Ser Glu Glu Lys Val Arg Asn Glu Pro Thr
         35                  40                  45

Gln Gln Gln Arg Ala Ala Met Leu Ile Lys Met Ile Leu Lys Lys Asp
     50                  55                  60

Asn Asp Ser Tyr Val Ser Phe Tyr Asn Ala Leu Leu His Glu Gly Tyr
 65                  70                  75                  80

Lys Asp Leu Ala Ala Leu Leu His Asp Gly Ile Pro Val Val Ser Ser
                 85                  90                  95

Ser Ser Val Arg Thr Val Leu Cys Glu Gly Gly Val Pro Gln Arg Pro
            100                 105                 110

Val Val Phe Val Thr Arg Lys Lys Leu Val Asn Ala Ile Gln Gln Lys
            115                 120                 125

Leu Ser Lys Leu Lys Gly Glu Pro Gly Trp Val Thr Ile His Gly Met
    130                 135                 140

Ala Gly Cys Gly Lys Ser Val Leu Ala Ala Glu Ala Val Arg Asp His
145                 150                 155                 160

Ser Leu Leu Glu Gly Cys Phe Pro Gly Gly Val His Trp Val Ser Val
                165                 170                 175

Gly Lys Gln Asp Lys Ser Gly Leu Leu Met Lys Leu Gln Asn Leu Cys
            180                 185                 190

Thr Arg Leu Asp Gln Asp Glu Ser Phe Ser Gln Arg Leu Pro Leu Asn
        195                 200                 205

Ile Glu Glu Ala Lys Asp Arg Leu Arg Ile Leu Met Leu Arg Lys His
    210                 215                 220

Pro Arg Ser Leu Leu Ile Leu Asp Asp Val Trp Asp Ser Trp Val Leu
225                 230                 235                 240

Lys Ala Phe Asp Ser Gln Cys Gln Ile Leu Leu Thr Thr Arg Asp Lys
                245                 250                 255

Ser Val Thr Asp Ser Val Met Gly Pro Lys Tyr Val Pro Val Glu
            260                 265                 270

Ser Ser Leu Gly Lys Glu Lys Gly Leu Glu Ile Leu Ser Leu Phe Val
    275                 280                 285

Asn Met Lys Lys Ala Asp Leu Pro Glu Gln Ala His Ser Ile Ile Lys
290                 295                 300

Glu Cys Lys Gly Ser Pro Leu Val Val Ser Leu Ile Gly Ala Leu Leu
305                 310                 315                 320

Arg Asp Phe Pro Asn Arg Trp Glu Tyr Tyr Leu Lys Gln Leu Gln Asn
                325                 330                 335

Lys Gln Phe Lys Arg Ile Arg Lys Ser Ser Tyr Asp Tyr Glu Ala
            340                 345                 350

Leu Asp Glu Ala Met Ser Ile Ser Val Glu Met Leu Arg Glu Asp Ile
        355                 360                 365

Lys Asp Tyr Tyr Thr Asp Leu Ser Ile Leu Gln Lys Asp Val Lys Val
    370                 375                 380
```

-continued

```
Pro Thr Lys Val Leu Cys Ile Leu Trp Asp Met Glu Thr Glu Glu Val
385                 390                 395                 400

Glu Asp Ile Leu Gln Glu Phe Val Asn Lys Ser Leu Leu Phe Cys Asp
            405                 410                 415

Arg Asn Gly Lys Ser Phe Arg Tyr Tyr Leu His Asp Leu Gln Val Asp
        420                 425                 430

Phe Leu Thr Glu Lys Asn Cys Ser Gln Leu Gln Asp Leu His Lys Lys
            435                 440                 445

Ile Ile Thr Gln Phe Gln Arg Tyr His Gln Pro His Thr Leu Ser Pro
450                 455                 460

Asp Gln Glu Asp Cys Met Tyr Trp Tyr Asn Phe Leu Ala Tyr His Met
465                 470                 475                 480

Ala Ser Ala Lys Met His Lys Glu Leu Cys Ala Leu Met Phe Ser Leu
            485                 490                 495

Asp Trp Ile Lys Ala Lys Thr Glu Leu Val Gly Pro Ala His Leu Ile
            500                 505                 510

His Glu Phe Val Glu Tyr Arg His Ile Leu Asp Glu Lys Asp Cys Ala
        515                 520                 525

Val Ser Glu Asn Phe Gln Glu Phe Leu Ser Leu Asn Gly His Leu Leu
        530                 535                 540

Gly Arg Gln Pro Phe Pro Asn Ile Val Gln Leu Gly Leu Cys Glu Pro
545                 550                 555                 560

Glu Thr Ser Glu Val Tyr Gln Gln Ala Lys Leu Gln Ala Lys Gln Glu
                565                 570                 575

Val Asp Asn Gly Met Leu Tyr Leu Glu Trp Ile Asn Lys Lys Asn Ile
            580                 585                 590

Thr Asn Leu Ser Arg Leu Val Val Arg Pro His Thr Asp Ala Val Tyr
        595                 600                 605

His Ala Cys Phe Ser Glu Asp Gly Gln Arg Ile Ala Ser Cys Gly Ala
        610                 615                 620

Asp Lys Thr Leu Gln Val Phe Lys Ala Glu Thr Gly Glu Lys Leu Leu
625                 630                 635                 640

Glu Ile Lys Ala His Glu Asp Glu Val Leu Cys Cys Ala Phe Ser Thr
                645                 650                 655

Asp Asp Arg Phe Ile Ala Thr Cys Ser Val Asp Lys Lys Val Lys Ile
            660                 665                 670

Trp Asn Ser Met Thr Gly Glu Leu Val His Thr Tyr Asp Glu His Ser
        675                 680                 685

Glu Gln Val Asn Cys Cys His Phe Thr Asn Ser Ser His Leu Leu
        690                 695                 700

Leu Ala Thr Gly Ser Ser Asp Cys Phe Leu Lys Leu Trp Asp Leu Asn
705                 710                 715                 720

Gln Lys Glu Cys Arg Asn Thr Met Phe Gly His Thr Asn Ser Val Asn
                725                 730                 735

His Cys Arg Phe Ser Pro Asp Asp Lys Leu Leu Ala Ser Cys Ser Ala
            740                 745                 750

Asp Gly Thr Leu Lys Leu Trp Asp Ala Thr Ser Ala Asn Glu Arg Lys
        755                 760                 765

Ser Ile Asn Val Lys Gln Phe Phe Leu Asn Leu Glu Asp Pro Gln Glu
        770                 775                 780

Asp Met Glu Val Ile Val Lys Cys Cys Ser Trp Ser Ala Asp Gly Ala
785                 790                 795                 800
```

-continued

Arg Ile Met Val Ala Lys Asn Lys Ile Phe Leu Trp Asn Thr Asp
         805                 810                 815

Ser Arg Ser Lys Val Ala Asp Cys Arg Gly His Leu Ser Trp Val His
        820                 825                 830

Gly Val Met Phe Ser Pro Asp Gly Ser Ser Phe Leu Thr Ser Ser Asp
        835                 840                 845

Asp Gln Thr Ile Arg Leu Trp Glu Thr Lys Lys Val Cys Lys Asn Ser
    850                 855                 860

Ala Val Met Leu Lys Gln Glu Val Asp Val Phe Gln Glu Asn Glu
865                 870                 875                 880

Val Met Val Leu Ala Val Asp His Ile Arg Arg Leu Gln Leu Ile Asn
                885                 890                 895

Gly Arg Thr Gly Gln Ile Asp Tyr Leu Thr Glu Ala Gln Val Ser Cys
        900                 905                 910

Cys Cys Leu Ser Pro His Leu Gln Tyr Ile Ala Phe Gly Asp Glu Asn
        915                 920                 925

Gly Ala Ile Glu Ile Leu Glu Leu Val Asn Asn Arg Ile Phe Gln Ser
        930                 935                 940

Arg Phe Gln His Lys Lys Thr Val Trp His Ile Gln Phe Thr Ala Asp
945                 950                 955                 960

Glu Lys Thr Leu Ile Ser Ser Ser Asp Asp Ala Glu Ile Gln Val Trp
                965                 970                 975

Asn Trp Gln Leu Asp Lys Cys Ile Phe Leu Arg Gly His Gln Glu Thr
        980                 985                 990

Val Lys Asp Phe Arg Leu Leu Lys Asn Ser Arg Leu Leu Ser Trp Ser
        995                 1000                1005

Phe Asp Gly Thr Val Lys Val Trp Asn Ile Ile Thr Gly Asn Lys Glu
    1010                1015                1020

Lys Asp Phe Val Cys His Gln Gly Thr Val Leu Ser Cys Asp Ile Ser
1025                1030                1035                1040

His Asp Ala Thr Lys Phe Ser Ser Thr Ser Ala Asp Lys Thr Ala Lys
                1045                1050                1055

Ile Trp Ser Phe Asp Leu Leu Leu Pro Leu His Glu Leu Arg Gly His
        1060                1065                1070

Asn Gly Cys Val Arg Cys Ser Ala Phe Ser Val Asp Ser Thr Leu Leu
        1075                1080                1085

Ala Thr Gly Asp Asp Asn Gly Glu Ile Arg Ile Trp Asn Val Ser Asn
    1090                1095                1100

Gly Glu Leu Leu His Leu Cys Ala Pro Leu Ser Glu Glu Gly Ala Ala
1105                1110                1115                1120

Thr His Gly Gly Trp Val Thr Asp Leu Cys Phe Ser Pro Asp Gly Lys
                1125                1130                1135

Met Leu Ile Ser Ala Gly Gly Tyr Ile Lys Trp Trp Asn Val Val Thr
        1140                1145                1150

Gly Glu Ser Ser Gln Thr Phe Tyr Thr Asn Gly Thr Asn Leu Lys Lys
        1155                1160                1165

Ile His Val Ser Pro Asp Phe Lys Thr Tyr Val Thr Val Asp Asn Leu
    1170                1175                1180

Gly Ile Leu Tyr Ile Leu Gln Thr Leu Glu
1185                1190

<210> SEQ ID NO 3
<211> LENGTH: 1481
<212> TYPE: DNA

<213> ORGANISM: Homo sapien

<400> SEQUENCE: 3

| | | | | | |
|---|---|---|---|---|---|
| gccatggacg | aagcggatcg | gcggctcctg | cggcggtgcc | ggctgcggct | ggtggaagag | 60 |
| ctgcaggtgg | accagctctg | ggacgtcctg | ctgagccgcg | agctgttcag | gccccatatg | 120 |
| atcgaggaca | tccagcgggc | aggctctgga | tctcggcggg | atcaggccag | gcagctgatc | 180 |
| atagatctgg | agactcgagg | gagtcaggct | cttcctttgt | tcatctcctg | cttagaggac | 240 |
| acaggccagg | acatgctggc | ttcgtttctg | cgaactaaca | gcaagcagg | aaagttgtcg | 300 |
| aagccaaccc | tagaaaacct | taccccagtg | gtgctcagac | cagagattcg | caaaccagag | 360 |
| gttctcagac | cggaaacacc | cagaccagtg | gacattggtt | ctggaggatt | cggtgatgtc | 420 |
| ggtgctcttg | agagtttgag | gggaaatgca | gatttggctt | acatcctgag | catggagccc | 480 |
| tgtggccact | gcctcattat | caacaatgtg | aacttctgcc | gtgagtccgg | gctccgcacc | 540 |
| cgcactggct | ccaacatcga | ctgtgagaag | ttgcggcgtc | gcttctcctc | gctgcatttc | 600 |
| atggtggagg | tgaagggcga | cctgactgcc | aagaaaatgg | tgctggcttt | gctggagctg | 660 |
| gcgcggcagg | accacggtgc | tctggactgc | tgcgtggtgg | tcattctctc | tcacggctgt | 720 |
| caggccagcc | acctgcagtt | cccagggct | gtctacggca | cagatggatg | ccctgtgtcg | 780 |
| gtcgagaaga | ttgtgaacat | cttcaatggg | accagctgcc | ccagcctggg | agggaagccc | 840 |
| aagctctttt | tcatccaggc | ctgtggtggg | gagcagaaag | accatggtt | tgaggtggcc | 900 |
| tccacttccc | ctgaagacga | gtcccctggc | agtaacccg | agccagatgc | cacccgttc | 960 |
| caggaaggtt | tgaggacctt | cgaccagctg | gacgccatat | ctagtttgcc | cacacccagt | 1020 |
| gacatctttg | tgtcctactc | tactttccca | ggttttgttt | cctggaggga | ccccaagagt | 1080 |
| ggctcctggt | acgttgagac | cctggacgac | atctttgagc | agtgggctca | ctctgaagac | 1140 |
| ctgcagtccc | tcctgcttag | ggtcgctaat | gctgtttcgg | tgaaagggat | ttataaacag | 1200 |
| atgcctggtt | gctttaattt | cctccggaaa | aaacttttct | ttaaaacatc | ataaggccag | 1260 |
| ggcccctcac | cctgccttat | cttgcacccc | caaagctttc | ctgccccagg | cctgaaagag | 1320 |
| gctgaggcct | ggactttcct | gcaactcaag | gactttgcag | ccggcacagg | gtctgctctt | 1380 |
| tctctgccag | tgacagacag | gctcttagca | gcttccagat | tgacgacaag | tgctgaacag | 1440 |
| tggaggaaga | gggacagatg | aatgccgtgg | attgcacgtg | g | | 1481 |

<210> SEQ ID NO 4
<211> LENGTH: 26
<212> TYPE: DNA
<213> ORGANISM: Artificial Sequence
<220> FEATURE:
<223> OTHER INFORMATION: Primer for used PCR generation of APAF-530

<400> SEQUENCE: 4
cgggatccga tggatgcaaa agctcg       26

<210> SEQ ID NO 5
<211> LENGTH: 34
<212> TYPE: DNA
<213> ORGANISM: Artificial Sequence
<220> FEATURE:
<223> OTHER INFORMATION: Primer used for PCR generation of APAF-530

<400> SEQUENCE: 5
ccgctcgagc tcactgactg cacaaatcct tttc       34

```
<210> SEQ ID NO 6
<211> LENGTH: 26
<212> TYPE: DNA
<213> ORGANISM: Artificial Sequence
<220> FEATURE:
<223> OTHER INFORMATION: Primer used for PCR generation of APAF-420

<400> SEQUENCE: 6
cgggatccga tggatgcaaa agctcg                                    26

<210> SEQ ID NO 7
<211> LENGTH: 28
<212> TYPE: DNA
<213> ORGANISM: Artificial Sequence
<220> FEATURE:
<223> OTHER INFORMATION: Primer used for PCR generation of APAF-420

<400> SEQUENCE: 7
ccgctcgagc tttccattcc gatcacag                                  28

<210> SEQ ID NO 8
<211> LENGTH: 26
<212> TYPE: DNA
<213> ORGANISM: Artificial Sequence
<220> FEATURE:
<223> OTHER INFORMATION: Primer used for PCR generation of APAF-350

<400> SEQUENCE: 8
cgggatccga tggatgcaaa agctcg                                    26

<210> SEQ ID NO 9
<211> LENGTH: 32
<212> TYPE: DNA
<213> ORGANISM: Artificial Sequence
<220> FEATURE:
<223> OTHER INFORMATION: Primer used for PCR generation of APAF-350

<400> SEQUENCE: 9
cgcctcgagg cctttacatt cttttataat ac                             32

<210> SEQ ID NO 10
<211> LENGTH: 26
<212> TYPE: DNA
<213> ORGANISM: Artificial Sequence
<220> FEATURE:
<223> OTHER INFORMATION: Primer used for PCR generation of APAF-97

<400> SEQUENCE: 10
cgggatccga tggatgcaaa agctcg                                    26

<210> SEQ ID NO 11
<211> LENGTH: 27
<212> TYPE: DNA
<213> ORGANISM: Artificial Sequence
<220> FEATURE:
<223> OTHER INFORMATION: Primer used for PCR generation of APAF-97

<400> SEQUENCE: 11
cgcctcgagg gaagaagaga caacagg                                   27

<210> SEQ ID NO 12
<211> LENGTH: 27
<212> TYPE: DNA
<213> ORGANISM: Artificial Sequence
<220> FEATURE:
<223> OTHER INFORMATION: Primer used for PCR generation of
      APAF-530deltaCARD
```

```
<400> SEQUENCE: 12
cgcggatcca gtgtaaggac agtcctg                                          27

<210> SEQ ID NO 13
<211> LENGTH: 33
<212> TYPE: DNA
<213> ORGANISM: Artificial Sequence
<220> FEATURE:
<223> OTHER INFORMATION: Primer used for PCR generation of
      APAF-530deltaCARD

<400> SEQUENCE: 13
ccgctcgagc tcactgactg cacaatcctt ttc                                   33

<210> SEQ ID NO 14
<211> LENGTH: 34
<212> TYPE: DNA
<213> ORGANISM: Artificial Sequence
<220> FEATURE:
<223> OTHER INFORMATION: Primer used for PCR generation of APAF-WD

<400> SEQUENCE: 14
cgggatccat ggagaatttt caggagtttt tatc                                  34

<210> SEQ ID NO 15
<211> LENGTH: 39
<212> TYPE: DNA
<213> ORGANISM: Artificial Sequence
<220> FEATURE:
<223> OTHER INFORMATION: Primer used for PCR generation of APAF-WD

<400> SEQUENCE: 15
cgcctcgagt tctaaagtct gtaaaatata taaaatacc                             39
```

TRUNCATED APAF-1 AND METHODS OF USE THEREOF

TECHNICAL FIELD

The present invention relates generally the regulation of apoptosis, and more particularly, to truncated Apaf-1 and methods of using truncated Apaf-1 and self-oligomerizing caspases to identify modulators of apoptosis.

BACKGROUND OF THE INVENTION

Apoptosis is the normal physiological process of programmed cell death that maintains tissue homeostasis. Changes to the apoptotic pathway that prevent or delay normal cell turnover can be just as important in the pathogenesis of diseases as are abnormalities in the regulation of the cell cycle. Like cell division, which is controlled through complex interactions between cell cycle regulatory proteins, apoptosis is similarly regulated under normal circumstances by the interaction of gene products that either prevent or induce cell death.

Since apoptosis functions in maintaining tissue homeostasis in a range of physiological processes such as embryonic development, immune cell regulation and normal cellular turnover, the dysfunction or loss of regulated apoptosis can lead to a variety of pathological disease states. For example, the loss of apoptosis can lead to the pathological accumulation of self-reactive lymphocytes that occurs with many autoimmune diseases. Inappropriate loss or inhibition of apoptosis can also lead to the accumulation of virally infected cells and of hyperproliferative cells such as neoplastic or tumor cells. Similarly, the inappropriate activation of apoptosis can also contribute to a variety of pathological disease states including, for example, acquired immunodeficiency syndrome (AIDS), neurodegenerative diseases and ischemic injury. Treatments which are specifically designed to modulate the apoptotic pathways in these and other pathological conditions can alter the natural progression of many of these diseases.

Although apoptosis is mediated by diverse signals and complex interactions of cellular gene products, the results of these interactions ultimately feed into a cell death pathway that is evolutionarily conserved between humans and invertebrates. The pathway, itself, is a cascade of proteolytic events analogous to that of the blood coagulation cascade.

Several gene families and products that modulate the apoptotic process have now been identified. One family is the aspartate-specific cysteine proteases ("caspases"). The human caspase family includes, for example, Ced-3, human ICE (interleukin-1-β converting enzyme) (caspase-1), ICH-1 (caspase-2), CPP32 (caspase-3), $ICE_{rel}II$ (caspase-4), $ICE_{rel}III$ (caspase-5), Mch2 (caspase-6), ICE-LAP3 (casepase-7), Mch5 (caspase-8), ICE-LAP6 (caspase-9), Mch4 (caspase-10), and others.

The caspase proteins share several common features. In this regard, caspases are cysteine proteases (named for a cysteine residue in the active site) that cleave substrates at Asp-X bonds. Furthermore, caspases are primarily produced as inactive zymogens that require proteolytic cleavage at specific internal aspartate residues for activation. The primary gene product is arranged such that the N-terminal peptide (prodomain) precedes a large subunit domain, which precedes a small subunit domain. The large subunit contains the conserved active site pentapeptide QACXG (X=R, Q, G) which contains the nucleophilic cysteine residue. The small subunit contains residues that bind the Asp carboxylate side chain and others that determine substrate specificity. Cleavage of a caspase yields the two subunits, the large (generally approximately 20 kD) and the small (generally approximately 10 kD) subunit that associate non-covalently: to form a heterodimer, and, in some caspases, an N-terminal peptide of varying length. The heterodimer may combine non-covalently to form a tetramer.

Caspase zymogens are themselves substrates for caspases. Inspection of the interdomain linkages in each zymogen reveals target sites (i.e. protease sites) that indicate a hierarchical relationship of caspase activation. By analyzing such pathways, it has been demonstrated that caspases are required for apoptosis to occur. Moreover, caspases appear to be necessary for the accurate and limited proteolytic events which are the hallmark of classic apoptosis (see Salvesen and Dixit, *Cell* 91:443–446, 1997). Once activated, most caspases can process and activate their own and other inactive procaspases in vitro (Fernandes-Alnemri et al., *Proc. Natl. Acad. Sci. USA* 93:7464–7469, 1996; Srinivasula et al., *Proc. Natl. Acad. Sci. USA* 93:13706–13711, 1996. This characteristic suggests that caspases implicated in apoptosis may execute the apoptotic program through a cascade of sequential activation of initiators and executioner procaspases (Salvesen and Dixit, *Cell* 91:443–446, 1997). The initiators are responsible for processing and activation of the executioners. The executioners are responsible for proteolytic cleavage of a number of cellular proteins leading to the characteristic morphological changes and DNA fragmentation that are often associated with apoptosis (reviewed by (Cohen, *Biochem. J.* 326:1–16, 1997; Henkart, *Immunity* 4:195–201, 1996; Martin and Green, *Cell* 82:349–352, 1995; Nicholson and Thornberry, *TIBS* 257:299–306, 1997; Porter et al., *BioEssays* 19:501–507, 1997; Salvesen and Dixit, *Cell* 91:443–446, 1997. The first evidence for an apoptotic caspase cascade was obtained from studies on death receptor signaling (reviewed by (Fraser and Evan, *Cell* 85:781–784, 1996; Nagata, *Cell* 88:355–365, 1997) which indicated that the death signal is transmitted in part by sequential activation of the initiator procaspase-8 and the executioner procaspase-3 (Boldin et al., *Cell* 85:803–815, 1996; Fernandes-Alnemri et al., *Proc. Natl. Acad. Sci. USA* 93:7464–7469, 1996; Muzio et al., *Cell* 85:817–827, 1996; Srinivasula et al., *Proc. Natl. Acad. Sci. USA* 93:13706–13711, 1996). More direct evidence was provided, recently, when it was demonstrated that the cytochrome c death signal is transmitted through activation of a cascade involving procaspase-9 and -3 (Li et al., *Cell* 91:479–489, 1997).

However, it remains unclear how the initiator caspases, like procaspase-8 and -9 are activated. While Apaf-1 is known to play a role in the activation of procaspase-9 the exact mechanism has yet to be determined.

Therefore, there exists a need in the art for methods of assaying compounds for their ability to affect Apaf-1 mediated caspase activity as well as for methods of modulating apoptosis in order to treat diseases and syndromes. The present invention fulfills this need, while further providing other related advantages.

SUMMARY OF THE INVENTION

The present invention generally provides truncated Apaf-1. In one aspect, the invention provides an isolated nucleic acid molecule encoding a truncated Apaf-1 or a variant thereof. In one embodiment, the encoded truncated Apaf-1 is a human truncated Apaf-1. In another embodiment, the human truncated Apaf-1 has the amino acid sequence of SEQ ID NO:2 or a variant thereof. In another embodiment, the nucleic acid molecule encoding a truncated Apaf-1 or variant thereof has the nucleic acid sequence of SEQ ID NO:1 or a variant thereof. In another embodiment, the nucleic acid molecule encodes a truncated Apaf-1 or fragment thereof that oligomerizes with a caspase. In yet another embodiment, the nucleic acid molecule encodes a human truncated Apaf-1 having the amino acid sequence of SEQ ID NO:2 or variant thereof that oligomerizes with a caspase.

It is another aspect of the invention to provide an expression vector comprising any of the nucleic acid molecules encoding a truncated Apaf-1 or a variant thereof referred to above, wherein the nucleic acid molecule encoding the truncated Apaf-1 is operatively linked to a promoter. In one embodiment, the promoter is inducible. In another aspect, the invention provides a host cell transfected with such expression vectors. In certain embodiments, the host cell may be a bacterium, an insect cell or a mammalian cell.

Another aspect of the invention pertains to an isolated truncated Apaf-1 polypeptide or fragment thereof. In one embodiment, the isolated truncated Apaf-1 polypeptide or fragment thereof oligomerizes with a caspase. In another embodiment, the isolated truncated Apaf-1 polypeptide or fragment thereof is a human truncated Apaf-1, which in a further embodiment may oligomerize with a caspase. In certain embodiments, the caspase with which an isolated truncated Apaf-1 polypeptide or fragment thereof oligomerizes may be caspase-1, caspase-2, caspase-3, caspase-4, caspase-5, caspase-6, caspase-7, caspase-8, caspase-9, caspase-10, caspase-11, caspase-12 or caspase-13. In certain embodiments, the caspase with which an isolated human truncated Apaf-1 polypeptide or fragment thereof oligomerizes may be caspase-1, caspase-2, caspase-3, caspase-4, caspase-5, caspase-6, caspase-7, caspase-8, caspase-9, procaspase-9, caspase-10, caspase-11, caspase-12 or caspase-13. In another embodiment, the isolated human truncated Apaf-1 polypeptide or fragment thereof comprises SEQ ID NO:2 or a variant thereof. In another embodiment, the isolated human truncated Apaf-1 polypeptide or fragment thereof is encoded by SEQ ID NO:1 or a variant thereof.

It is another aspect of the invention to provide a method of identifying an inhibitor or enhancer of Apaf-1 mediated caspase processing, by contacting a sample containing a truncated Apaf-1 or fragment thereof and one or more caspases with a candidate inhibitor or candidate enhancer, detecting the presence of large and small caspase subunits, and therefrom determining the level of caspase processing activity, wherein a decrease in processing indicates the presence of a caspase processing inhibitor, and wherein an increase in processing indicates the presence of a caspase processing enhancer. In one embodiment of this aspect of the invention, at least one of the caspases is procaspase-9 or a functional fragment thereof. In another embodiment, the caspase is in vitro translated and labeled. In a further embodiment, the label may be a radioactive label, a peptide tag, an enzyme or biotin.

Another aspect of the invention provides a method of identifying an inhibitor or enhancer of Apaf-1 mediated caspase processing, by contacting a cell transfected with a vector expressing a nucleic acid encoding truncated Apaf-1 or a variant thereof as described above with a candidate inhibitor or candidate enhancer, detecting the presence of large and small caspase subunits, and therefrom determining the level of caspase processing activity, wherein a decrease in processing indicates the presence of a caspase inhibitor, and wherein an increase in processing indicates the presence of a caspase processing enhancer.

In certain embodiments of these methods of identifying an inhibitor or enhancer of Apaf-1 mediated caspase processing, the step of detecting comprises gel electrophoresis.

Turning to another aspect of the invention, a method is provided for identifying an inhibitor or enhancer of Apaf-1 mediated apoptosis by contacting a cell transfected with a vector expressing truncated Apaf-1 or a variant thereof as described above with a candidate inhibitor or candidate enhancer, and detecting cell viability, wherein an increase in cell viability indicates the presence of an inhibitor and an decrease in cell viability indicates an enhancer.

It is another aspect of the invention to provide a method for inducing apoptosis in a cell, by delivering to a cell an effective amount of a nucleic acid molecule encoding a truncated Apaf-1 polypeptide, and maintaining the cell under conditions sufficient for expression of the polypeptide. In one embodiment, the step of delivering comprises injecting the nucleic acid molecule into the cell. In another embodiment, the step of delivering comprises administering the nucleic acid molecule to the circulatory system of a warm-blooded mammal in which the cell is located.

In another aspect of the invention, an antisense nucleic acid molecule is provided comprising a nucleic acid sequence that is complementary to a nucleic acid molecule encoding a truncated Apaf-1.

In another aspect of the invention, a gene delivery vehicle is provided comprising a nucleic acid molecule encoding truncated Apaf-1 or a variant thereof as described above wherein the nucleic acid molecule is operatively linked to a promoter. In certain embodiments the vehicle is a retrovirus or adenovirus. In certain other embodiments, the nucleic acid molecule is associated with a polycation. In certain other embodiments, the gene delivery vehicle may further comprise a ligand that binds a cell surface receptor.

The invention also provides a method of treating cancer, by administering to a patient a gene delivery vehicle comprising a nucleic acid molecule encoding truncated Apaf-1 or a variant thereof as described above, wherein the nucleic acid molecule is operatively linked to a promoter and wherein the gene delivery vehicle is internalized by tumor cells.

In another aspect the invention provides a method of treating autoimmune disease by administering to a patient a gene delivery vehicle comprising a nucleic acid molecule encoding truncated Apaf-1 or a variant thereof as described above wherein the nucleic acid molecule is operatively linked to a promoter and which may further be a retrovirus or adenovirus, a nucleic acid molecule associated with a polycation or a ligand that binds a cell surface receptor, and wherein the gene delivery vehicle is internalized by cells mediating autoimmune disease.

Another aspect of the invention provides a method of identifying an inhibitor of Apaf-1 mediated caspase processing by contacting a cell transfected with an inducible expression vector expressing truncated Apaf-1 or a variant thereof as described above with a candidate inhibitor; contacting the transfected cell with an inducer capable of inducing truncated Apaf-1 expression, and detecting the presence of large and small caspase subunits, and therefrom determining the level of caspase processing activity, wherein a decrease in processing indicates the presence of a caspase processing inhibitor. In one embodiment, the step of detecting comprises gel electrophoresis.

In another aspect of the invention, a method is provided for identifying an inhibitor of Apaf-1 mediated apoptosis by contacting a cell transfected with an inducible expression vector expressing truncated Apaf-1 or a variant thereof as described above with a candidate inhibitor, contacting the transfected cell with an inducer capable of inducing truncated Apaf-1 expression; and detecting cell viability, wherein an increase in cell viability indicates the presence of an inhibitor.

Another aspect of the invention provides a method of identifying an inhibitor of apoptosis by contacting a cell transfected with an inducible expression vector capable of expressing a self-oligomerizing and self-processing caspase with a candidate inhibitor; contacting the transfected cell with an inducer capable of inducing self-oligomerizing caspase expression, and detecting the presence of large and small caspase subunits, and therefrom determining the level of caspase processing activity, wherein a decrease in processing indicates the presence of an apoptosis inhibitor. In one embodiment, the step of detecting comprises gel electrophoresis.

Another aspect of the invention provides a method of identifying an inhibitor of apoptosis, by contacting a cell transfected with an inducible expression vector capable of expressing a self-oligomerizing and self-processing caspase with a candidate inhibitor; contacting the transfected cell with an inducer capable of inducing self-oligomerizing caspase expression; and detecting cell viability, wherein an increase in cell viability indicates the presence of an inhibitor.

Another aspect of the invention provides a method for inhibiting apoptosis in a cell by delivering to a cell an effective amount of a nucleic acid molecule encoding a caspase-9 prodomain; and maintaining the cell under conditions sufficient for expression of the polypeptide.

Another aspect of the invention provides a method for inducing apoptosis in a cell, by delivering to a cell an effective amount of a nucleic acid molecule encoding a self-oligomerizing caspase-9 polypeptide; and maintaining the cell under conditions sufficient for expression of the polypeptide. In one embodiment, the step of delivering comprises injecting the nucleic acid molecule into the cell. In another embodiment, the step of delivering comprises administering the nucleic acid molecule to the circulatory system of a warm-blooded mammal in which the cell is located.

Another aspect of the invention provides a gene delivery vehicle comprising a nucleic acid molecule encoding a self-oligomerizing caspase-9 polypeptide, wherein the nucleic acid molecule is operatively linked to a promoter. In certain embodiments, the vehicle is a retrovirus or adenovirus. In certain other embodiments, the nucleic acid molecule is associated with a polycation. In certain other embodiments, the gene delivery vehicle may further comprise a ligand that binds a cell surface receptor.

Turning to another aspect, the invention provides a method of treating cancer by administering to a patient a gene delivery vehicle comprising a nucleic acid molecule encoding a self-oligomerizing caspase-9 polypeptide, wherein the nucleic acid molecule is operatively linked to a promoter, wherein the gene delivery vehicle is internalized by tumor cells. In certain embodiments, the vehicle is a retrovirus or adenovirus. In certain other embodiments, the nucleic acid molecule is associated with a polycation, and in certain other embodiments, the gene delivery vehicle may further comprise a ligand that binds a cell surface receptor.

It is yet another aspect of the invention to provide a method of treating autoimmune disease by administering to a patient a gene delivery vehicle comprising a nucleic acid molecule encoding a self-oligomerizing caspase-9 polypeptide, wherein the nucleic acid molecule is operatively linked to a promoter and wherein the gene delivery vehicle is internalized by tumor cells. In certain embodiments, the vehicle is a retrovirus or adenovirus. In certain other embodiments, the nucleic acid molecule is associated with a polycation.

These and other aspects of the present invention will become evident upon reference to the following detailed description and attached drawings. In addition, the various references set forth below that describe in more detail certain procedures or compositions (e.g., plasmids, etc.), and are therefore incorporated by reference in their entirety.

Figure 12:
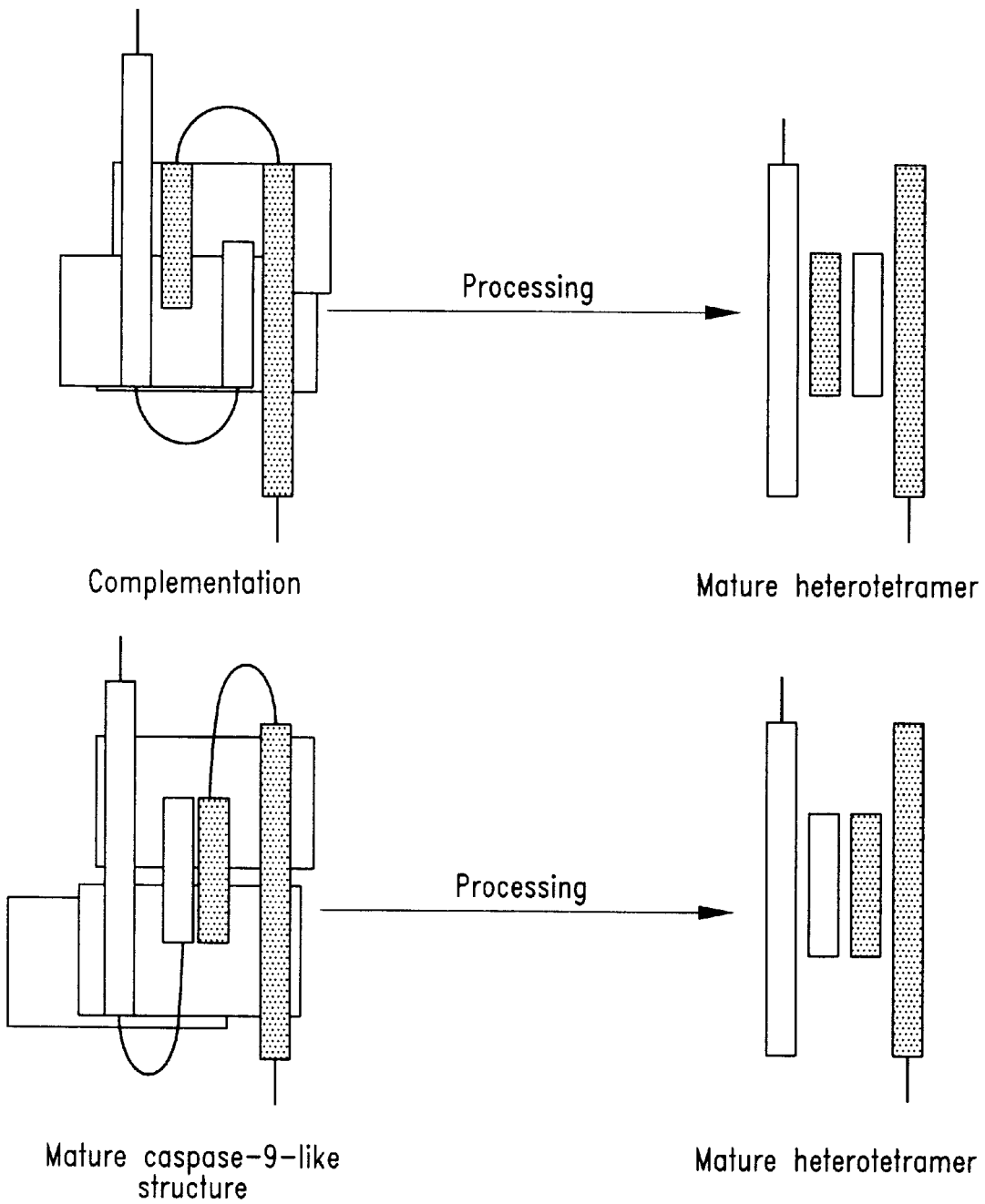

FIG. 12 is a schematic diagram illustrating two possible mechanisms of activation of procaspase-9 by oligomerization.

Figure 13:
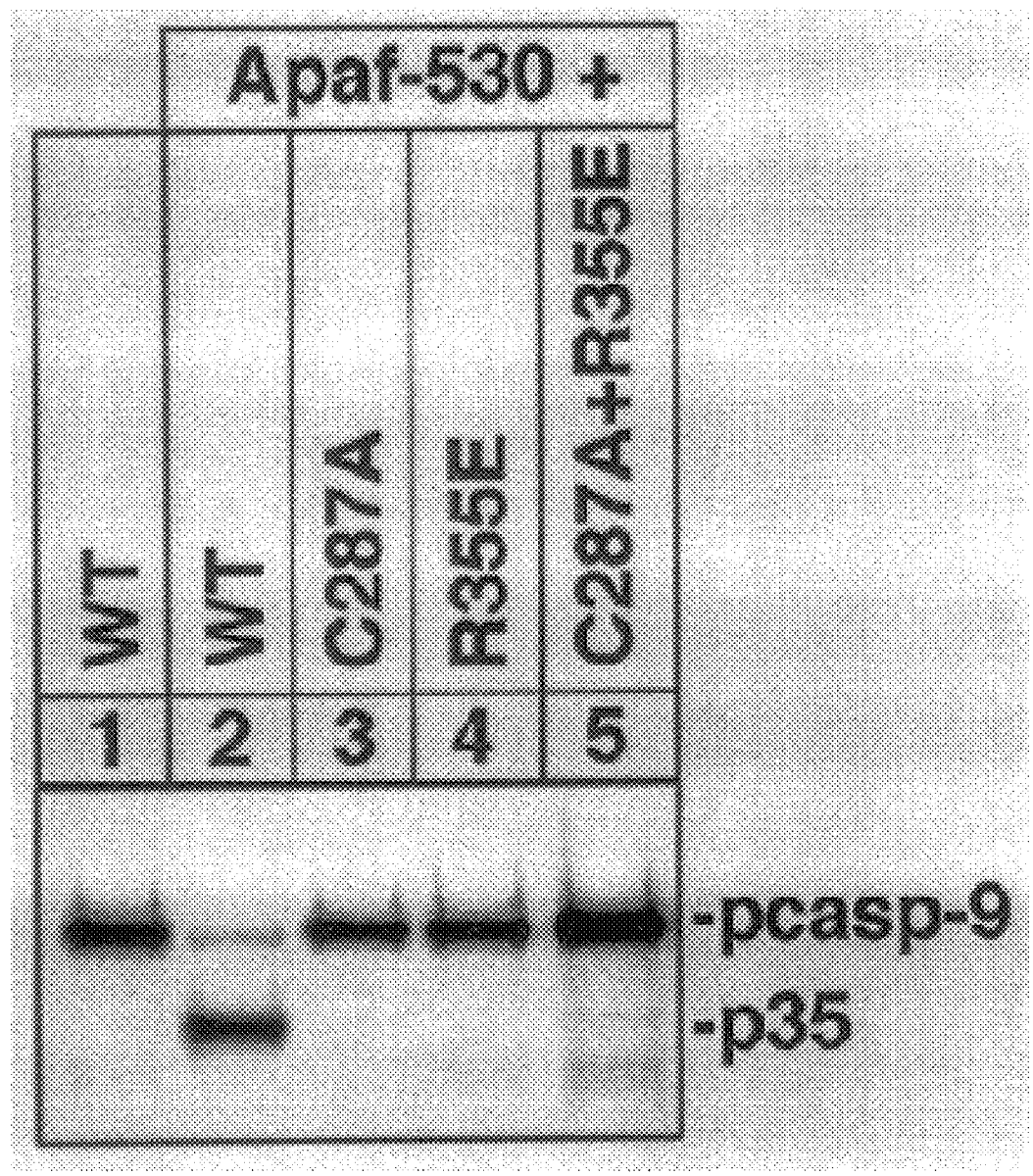

FIG. 13 is a scanned image of an autoradiogram representing SDS-PAGE analysis of the complementary processing ability of procaspase-9 mutants in the presence of Apaf-530.

Figure 14:
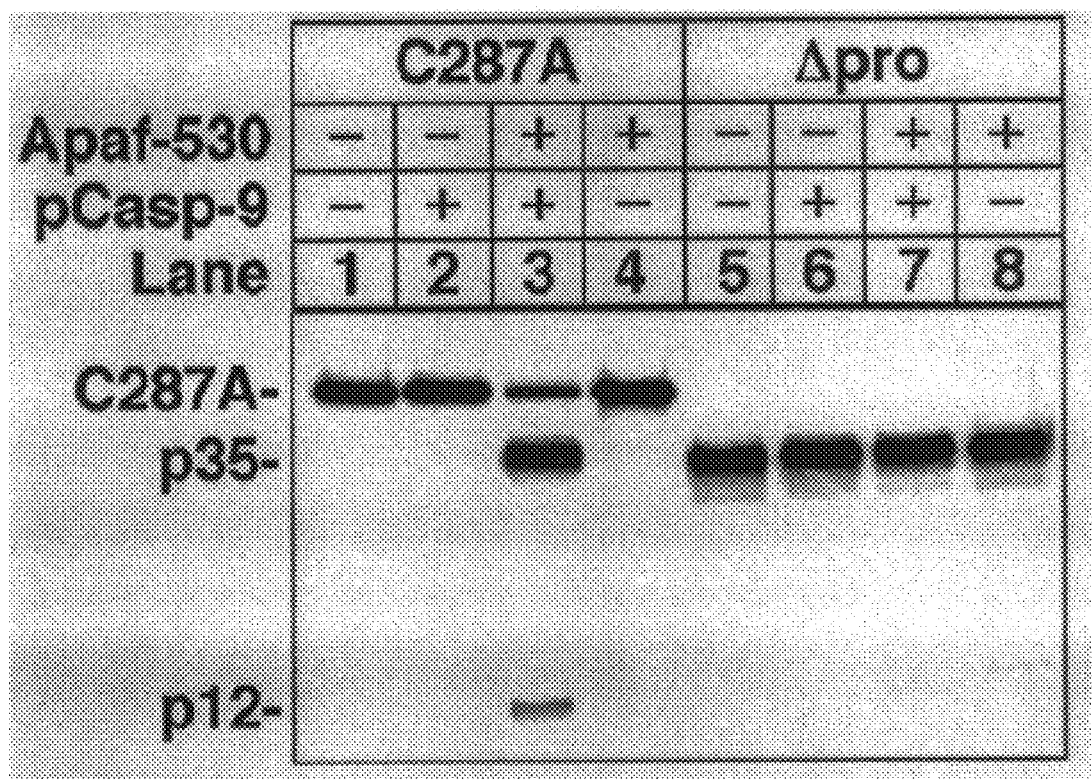

FIG. 14 is a scanned image of an autoradiogram representing SDS-PAGE analysis of the ability of WT procaspase-9 in the presence of Apaf-530 to induce autoprocessing of procaspase-9 mutants.

Figure 15:
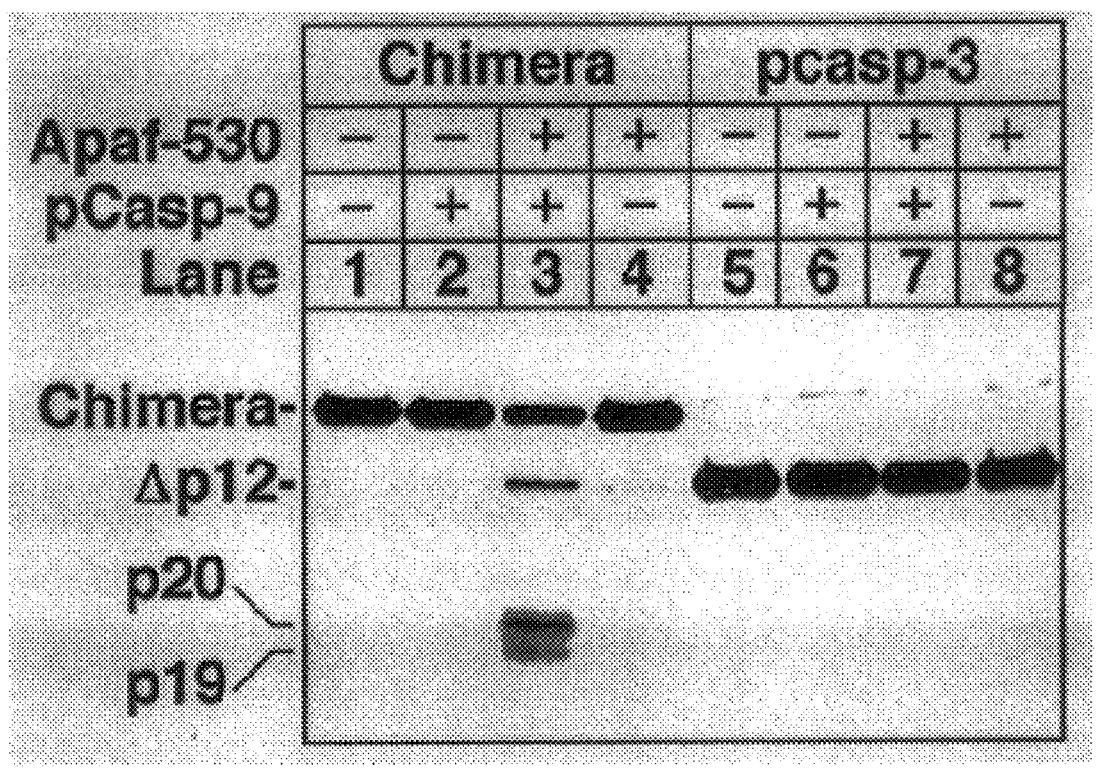

FIG. 15 is a scanned image of an autoradiogram representing SDS-PAGE analysis of the ability of mature Apaf-530-bound caspase-9 to process a chimeric procaspase-3 with an N-terminal procaspase-9 prodomain. Δp 12 indicates the chimeric procaspase-3 without its p12 region.

Figure 16:
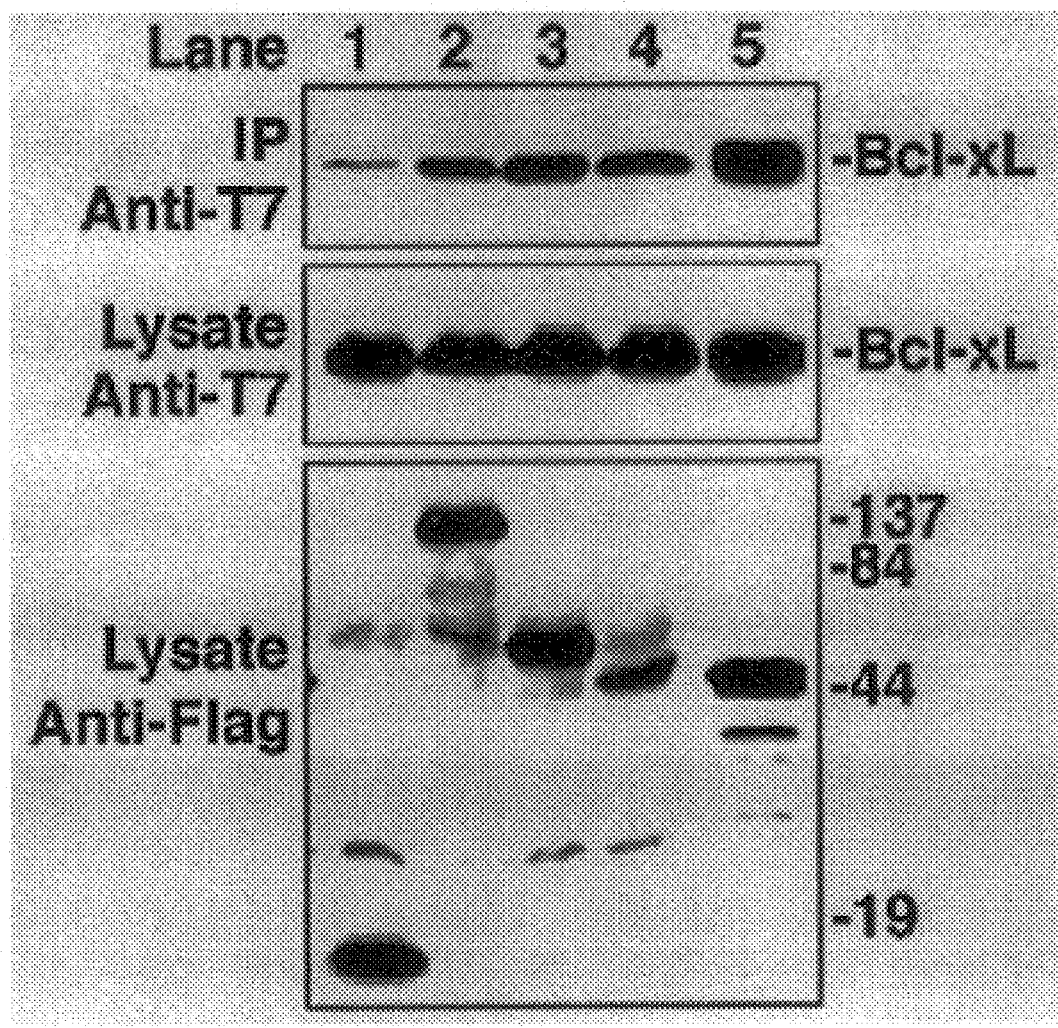

FIG. 16 is a scanned image of an immunoblot representing SDS-PAGE analysis of the ability of Apaf-1 to interact with Bcl-$x_L$. The molecular mass markers are indicated to the right of the lower panel.

Figure 17:
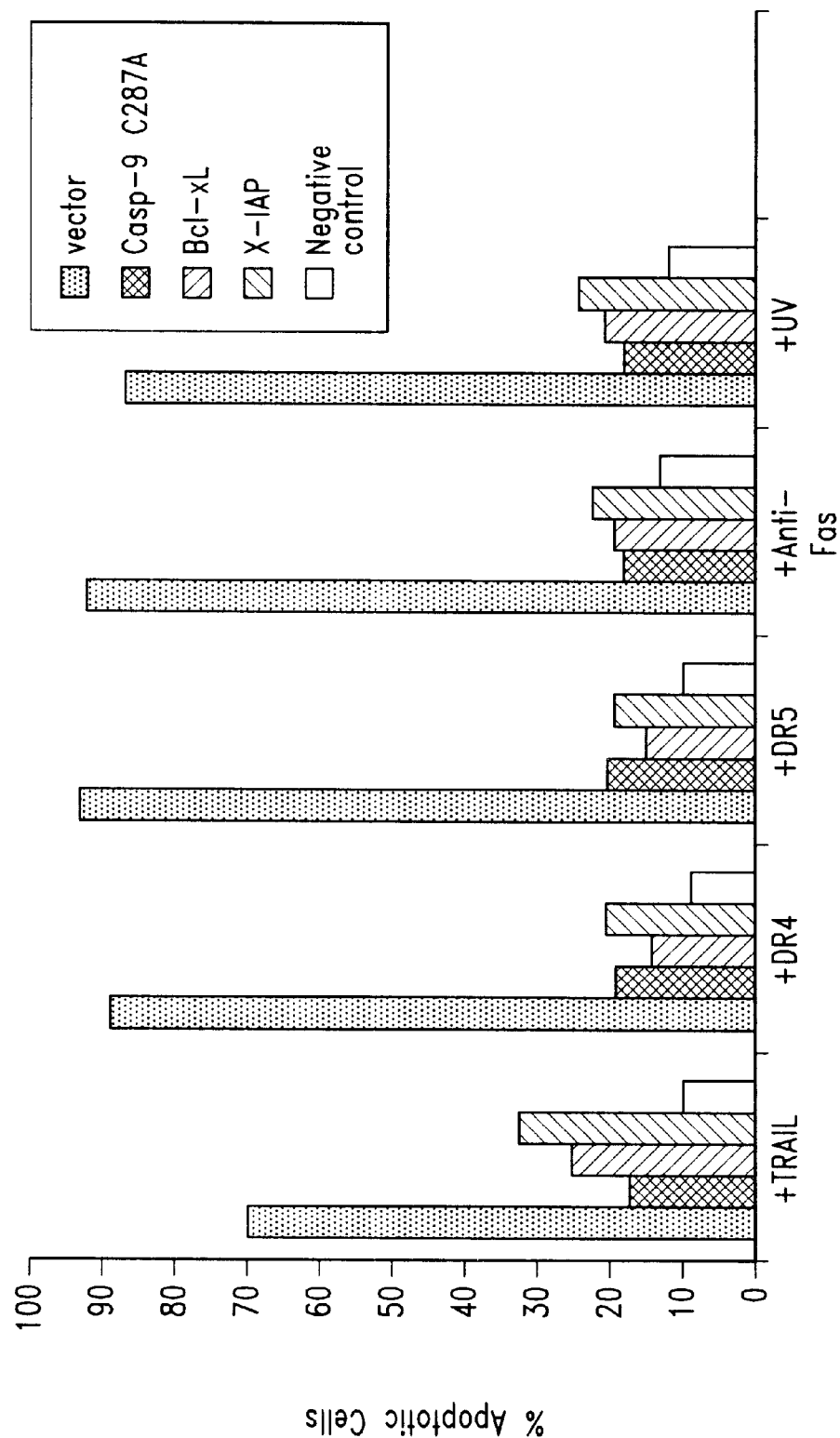

FIG. 17 is a bar diagram representing the ability of dominant negative procaspase-9 to inhibit apoptosis in vivo.

Figure 18:
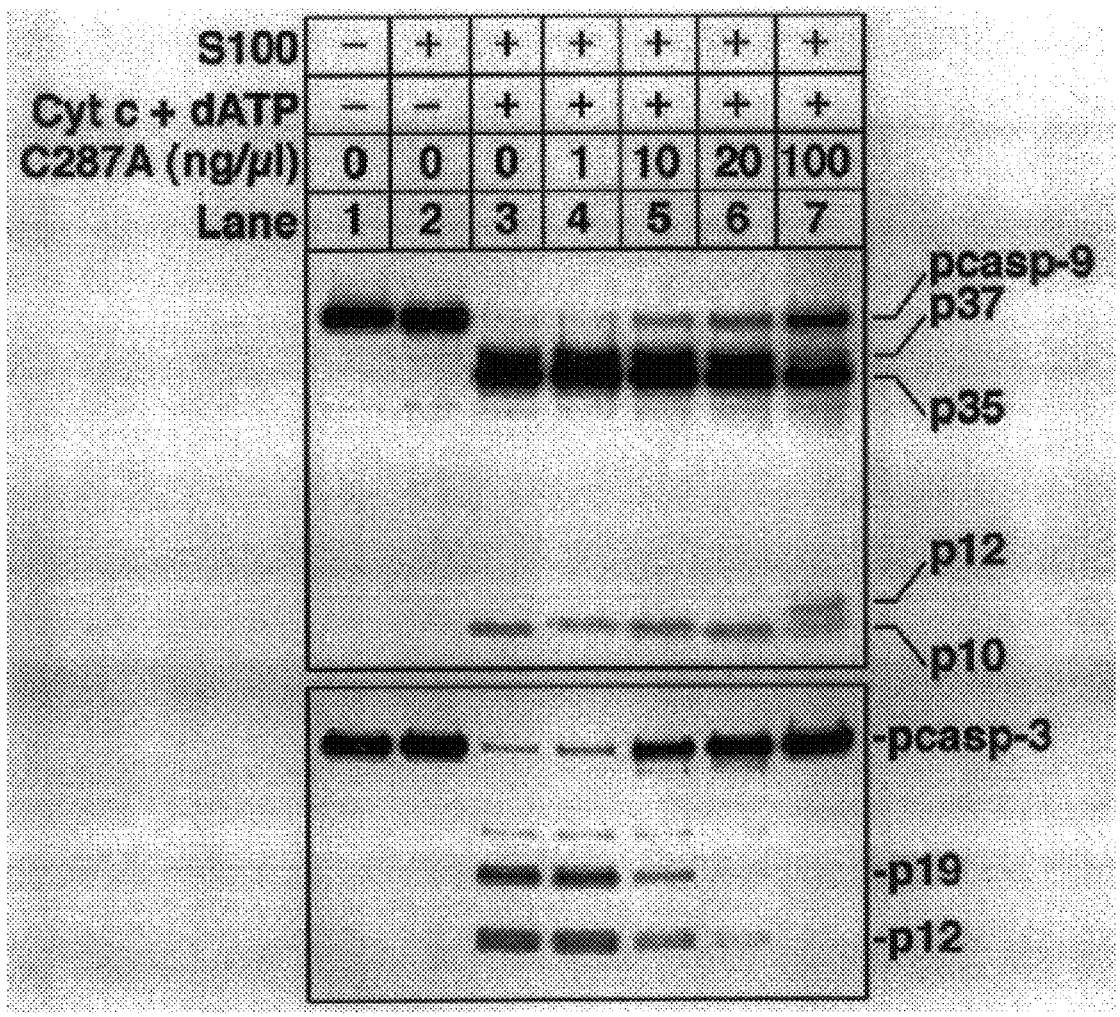

FIG. 18 is a scanned image of an autoradiogram representing SDS-PAGE analysis of the ability of dominant negative procaspase-9-C287A mutant to inhibit autoprocessing of procaspase-3 and -9 in vitro.

FIG. 19 depicts the nucleic acid sequence (SEQ ID NO:1) and the amino acid sequence (SEQ ID NO:2) of Apaf-1.

FIG. 20 depicts the nucleic acid sequence (SEQ ID NO:3) of Caspase-9.

DETAILED DESCRIPTION OF THE INVENTION

Prior to setting forth the invention, it may be helpful to an understanding thereof to set forth definitions of certain terms that will be used hereinafter.

"Truncated Apaf-1" refers to an Apaf-1 molecule comprising less than 60% and in some embodiments less than 50% and other embodiments less than 45% of the native human sequence and being capable of oligomerizing with a caspase in the absence of cytochrome c and dATP. Briefly, Apaf-1 is the functional homolog of *C. elegans* CED-4 (Yuan and Horvitz, *Development* 16:309–320, 1992; Zou et al., *Cell* 90:405–413, 1997). It is composed of three functional domains, a short N-terminal CARD (caspase recruitment domains) (Hofmann et al., *Trends Biochem. Sci.* 257:155–156, 1997), a central CED-4 homology domain and a long WD-40 repeat domain. Binding of Apaf-1 to cytochrome c in the presence of dATP exposes its CARD, which then binds to a corresponding motif in the prodomain of procaspase-9 resulting in its recruitment to this complex (Li et al., *Cell* 91:479–489, 1997). Recruitment of procaspase-9 to the Apaf-1 complex results in its activation by an as yet unknown mechanism.

The truncated Apaf-1 molecules of the subject invention also include variants (including alleles) of the native protein sequence. Briefly, such variants may result from natural polymorphisms or may be synthesized by recombinant methodology, and differ from wild-type protein by one or more amino acid substitutions, insertions, deletions, or the like. Variants generally have at least 75% nucleotide identity to native sequence, preferably at least 80%–85%, and most preferably at least 90% nucleotide identity. Typically, when engineered, amino acid substitutions will be conservative, i.e., substitution of amino acids within groups of polar, non-polar, aromatic, charged, etc. amino acids. In the region of homology to the native sequence, variants should preferably have at least 90% amino acid sequence identity, and within certain embodiments, greater than 92%, 95%, or 97% identity. Such amino acid sequence identity may be determined by standard methodologies, including use of the National Center for Biotechnology Information BLAST search methodology available at www.ncbi.nlm.nih.gov. The identity methodologies most preferred are those described in U.S. Pat. No. 5,691,179 and Altschul et al., Nucleic Acids Res. 25:3389–3402, 1997, both of which are incorporated herein by reference.

As will be appreciated by those skilled in the art, a nucleotide sequence encoding a truncated Apaf-1 or variant thereof may differ from known native sequence, due to codon degeneracies, nucleotide polymorphisms, or amino acid differences. In certain embodiments, variants will preferably hybridize to the native nucleotide sequence at conditions of normal stringency, which is approximately 25–30° C. below Tm of the native duplex (e.g., 5×SSPE, 0.5% SDS, 5×Denhardt's solution, 50% formamide, at 42° C. or equivalent conditions; see generally, Sambrook et al. *Molecular Cloning: A Laboratory Manual*, 2nd ed., Cold Spring Harbor Press, 1989; Ausubel et al., *Current Protocols in Molecular Biology*, Greene Publishing, 1995). By way of comparison, low stringency hybridizations utilize conditions approximately 40° C. below Tm, and high stringency hybridizations utilize conditions approximately 10° C. below Tm.

A "caspase" refers to a cysteine protease that specifically cleaves proteins after Asp residues. Caspases are initially expressed as zymogens, in which a large subunit is N-terminal to a small subunit. Caspases are generally activated by cleavage at internal Asp residues. These proteins have been identified in many eukaryotes, including *C. elegans*, Drosophila, mouse, and humans. Currently, there are at least 13 known caspase genes, named caspase-1 through caspase-13. Caspases are found in myriad organisms, including human, mouse, insect (e.g., Drosophila), and other invertebrates (e.g., *C. elegans*). In Table 1, ten human caspases are listed along with their alternative names.

| Caspase | Alternative name |
| --- | --- |
| Caspase-1 | ICE |
| Caspase-2 | ICH-1 |
| Caspase-3 | CPP32, Yama, apopain |
| Caspase-4 | $ICE_{rel}II$; TX, ICH-2 |
| Caspase-5 | $ICE_{rel}III$; TY |
| Caspase-6 | Mch2 |
| Caspase-7 | Mch3, ICE-LAP3, CMH-1 |
| Caspase-8 | FLICE; MACH; Mch5 |
| Caspase-9 | ICE-LAP6; Mch6 |
| Caspase-10 | Mch4, FLICE-2 |

An "isolated nucleic acid molecule" refers to a polynucleotide molecule in the form of a separate fragment or as a component of a larger nucleic acid construct, that has been separated from its source cell (including the chromosome it normally resides in) at least once, and preferably in a substantially pure form. Nucleic acid molecules may be comprised of a wide variety of nucleotides, including DNA, RNA, nucleotide analogues, or combination thereof.

The term "self-oligomerizing" refers to the ability of a polypeptide construct to form multimers with other copies of itself. The polypeptide may be caspases which are chimeras of other caspases, caspase-fusion constructs (e.g., Fc-caspase fusions), mutagenized caspases, or truncated caspases. Self-oligomerizing constructs which are useful within the context of the invention are caspases which either activate caspases, following oligomerization, thereby activating apoptosis, or which bind to and inhibit or sequester other caspases, thereby inhibiting caspase activation and resulting apoptosis.

The term "in vitro" refers to cell free systems.

The term "in vivo" refers to whole cell systems, which include, for example, primary and secondary cell culture, whole organs culture, whole organisms, and similar systems as known to those of ordinary skill in the art.

A. TRUNCATED APAF-1 NUCLEIC ACID MOLECULES AND ENCODED PRODUCTS THEREOF

1. Isolation of Apaf-1 and Caspase Nucleic Acid Molecules

The present invention provides truncated Apaf-1 nucleic acid molecules which, in certain embodiments, are constructed from full-length Apaf-1 nucleic acid molecules. Apaf-1 and caspase nucleic acid molecules used in the subject invention may be isolated from either genomic DNA or preferably cDNA (see U.S. Ser. No. 08/869,553 and U.S. Pat. No. 5,550,019, each of which are incorporated herein by reference). Isolation of Apaf-1 and caspase nucleic acid molecules from genomic DNA or cDNA typically can proceed by, first, generating an appropriate DNA library through techniques for constructing libraries that are known in the art (see Sambrook et al., *Molecular Cloning: A Laboratory Manual*, Cold Spring Harbor Press, 1989) or purchased from commercial sources (e.g., Clontech, Palo Alto, Calif.). Briefly, cDNA libraries can be constructed in bacteriophage vectors (e.g.,λZAPII), plasmids, or others, which are suitable for screening, while genomic DNA libraries can be constructed in chromosomal vectors, such as YACs (yeast artificial chromosomes), bacteriophage vectors, such as λEMBL3, λgt10, cosmids, or plasmids.

In one embodiment, known Apaf-1 and caspase sequences may be utilized to design an oligonucleotide hybridization probe suitable for screening genomic or cDNA libraries. Preferably, such oligonucleotide probes are 20–30 bases in length. To facilitate hybridization detection, the oligonucleotide may be conveniently labeled, generally at the 5' end, with a reporter molecule, such as a radionuclide, (e.g., $^{32}P$), enzymatic label, protein label, fluorescent label, or biotin. Such libraries are then generally plated as phage or colonies, depending upon the vector used. Subsequently, a nitrocellulose or nylon membrane, to which the colonies or phage have been transferred, is probed to identify candidate clones which contain the caspase gene. Such candidates may be verified as containing caspase DNA by any of various means including, for example, DNA sequence analysis or hybridization with a second, non-overlapping probe.

Once a library is identified as containing an Apaf-1 or caspase nucleic acid molecule, the molecule can be isolated by amplification. Briefly, when using cDNA library DNA as a template, amplification primers are designed based upon known Apaf-1 or caspase nucleic acid sequences (see GenBank Accession Nos. AF013263 (Apaf-1), X65019 (caspase-1), U13021 (caspase-2), U13737 (caspase-3), U25804 (caspase-4), U28015 (caspase-5), U20536 (caspase-6), U37448 (caspase-7), U60520 (caspase-8), U56390 (caspase-9), U60519 (caspase-10), and sequences provided herein). Amplification of cDNA libraries made from cells with high caspase or Apaf-1 activity is preferred. Primers for amplification are preferably derived from sequences in the 5' and 3' untranslated region in order to isolate a full-length cDNA. The primers preferably have a GC content of about 50% and contain restriction sites to facilitate cloning and do not have self-complementary sequences nor do they contain complementary sequences at their 3' end (to prevent primer-dimer formation). The primers are annealed to cDNA or genomic DNA and sufficient amplification cycles are performed to yield a product readily visualized by gel electrophoresis and staining. The amplified fragment is purified and inserted into a vector, such as λgt10 or pBS(M13+), and propagated. Confirmation of the nature of the fragment may be obtained by DNA sequence analysis, or indirectly through amino acid sequencing of the encoded protein.

Other methods may also be used to obtain an Apaf-1 or caspase encoding nucleic acid molecule. For example, a nucleic acid molecule encoding an Apaf-1 or caspase may be obtained from an expression library by screening with an antibody or antibodies reactive to such an Apaf-1 or caspase (see, Sambrook, et al. *Molecular Cloning: A Laboratory Manual*, 2nd Ed., Cold Spring Harbor Laboratory Press, NY, 1989; Ausubel, et al. *Current Protocols in Molecular Biology*, Greene Publishing Associates and Wiley-Interscience, NY, 1995).

Apaf-1 and caspase nucleic acid molecules from a variety of species may be isolated using the compositions provided herein. For closely related species, the human sequence or portion thereof may be utilized as a probe on a genomic or cDNA library. For example, a fragment of nucleic acid that encodes a polypeptide region that encompasses the CARD domain of Apaf-1 or the catalytic site of a caspase may be labeled and used as a probe on a library constructed from mouse, primate, rat, dog, or other vertebrate, warm-blooded or mammalian species. An initial hybridization at normal stringency may yield candidate clones or fragments. If no hybridization is initially observed, varying degrees of stringency may be used (see Sambrook et al., supra, and other well-known sources for stringency conditions). While such probes may also be used to probe libraries from evolutionarily diverse species, such as Drosophila, hybridization conditions will likely be less stringent.

While relaxed hybridization conditions using probes designed from human sequences may identify Apaf-1 or caspase nucleic acid molecules of evolutionarily diverse species, it may be more beneficial to attempt to directly isolate these molecules from a library using methods which do not require the human sequence per se. These methods include, but are not limited to, amplification using primers derived from conserved areas, amplification using degenerate primers from various regions, antibody probing of expression libraries, and the like. For example, random-primed amplification (e.g., polymerase chain reaction) may be employed (see, e.g., *Methods Enzymol.* 254:275, 1995; *Trends Genet.* 11:242, 1995; Liang and Pardee, *Science* 257:967, 1992; Welsh et al., *Nucl. Acids Res.* 20:4965, 1992). In addition, variations of random-primed PCR may also be used, especially when a particular gene or gene family is desired. In such a method, one of the amplification primers is an "anchored oligo(dT) (oligo(dT)dN)" and the other primer is a degenerate primer based upon amino acid or nucleotide sequence of a related gene. A gene sequence is identified as an Apaf-1 or caspase by amino acid similarity and/or nucleic acid similarity. Generally, amino acid similarity is preferred. Candidate Apaf-1 or caspase genes may be examined for enzyme activity by one of the functional assays described herein, or other equivalent assays.

Variants of Apaf-1, truncated Apaf-1, and caspase nucleic acid molecules provided herein may be engineered from natural variants (e.g., polymorphisms, splice variants, mutants), synthesized or constructed. Many methods have been developed for generating mutants (see, generally, Sambrook et al., supra; Ausubel, et al., supra, and the discussion above). Briefly, preferred methods for generating nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, typically *E. coli*, but alternatively, other prokaryotes, yeast or other eukaryotes. Standard screening and vector growth protocols are used to identify mutant sequences and obtain high yields.

Similarly, deletions and/or insertions of the Apaf-1, truncated Apaf-1, or caspase nucleic acid molecule may be constructed by any of a variety of known methods as discussed supra. For example, the nucleic acid molecule can be digested with restriction enzymes and religated, thereby deleting or religating a sequence with additional sequences, such that an insertion or large substitution is made. Other means of generating variant sequences may be employed using methods known in the art, for example those described in Sambrook et al., supra; Ausubel et al., supra. Verification of variant sequences is typically accomplished by restriction enzyme mapping, sequence analysis, or probe hybridization. Variants of caspase nucleic acid molecules whose encoded product is capable of oligomerizing to itself or a form of Apaf-1 or capable of being processed to an active form which will catalyze Asp-specific cleavages, are useful in the context of the subject invention. Moreover, the variant Apaf-1 and truncated Apaf-1 nucleic acid molecules which encode products capable of oligomerizing with caspases, caspase variants, or Bcl-$x_L$ proteins are useful in the context of this invention.

B. TRUNCATED APAF-1

Figure 1:
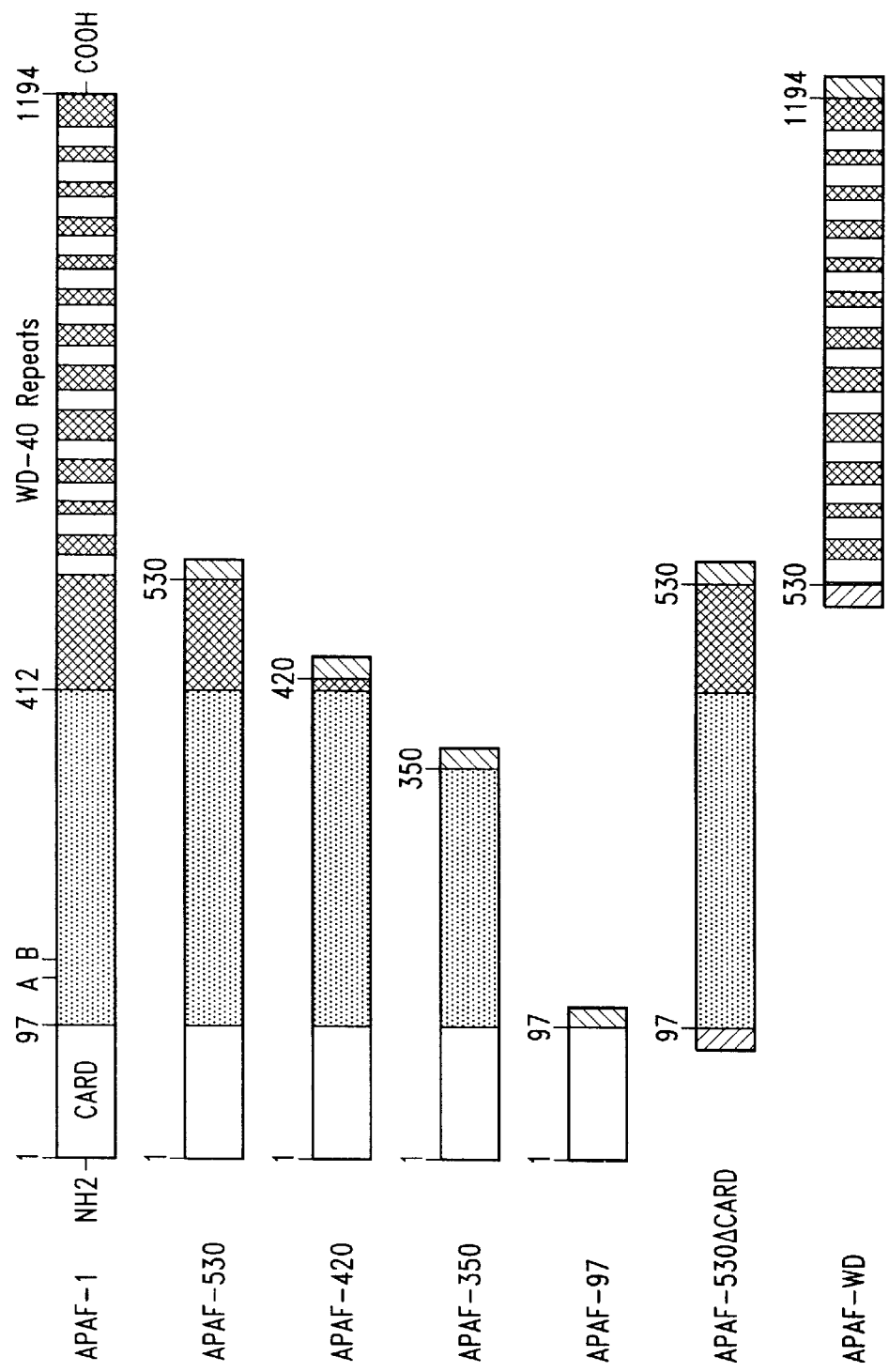
FIG. 1 is a schematic diagram of full length Apaf-1 and truncated forms thereof. The hatched boxes at the C-termini represent His6-tags, to facilitate purification, while the hatched boxes located at the N-termini represent T7-tags, to aid in immunoblot detection. The N-terminal CARD domain is labeled and represented as a white box (residues 1–97), the central CED-4 homology domain (residues 98–412) containing Walker A and B (represented by A and B) sequences which include a P-loop sequence for nucleotide binding (residues 139–157) and a putative $Mg^{++}$ binding site (residues 228–235) is represented by black box, and the C-terminal domain that contains 12 WD-40 repeats (residues 413–1194) is illustrated by box containing gray and white rectangles.

The truncated Apaf-1 molecules of the present invention may be generated by truncating the gene sequence of the Apaf-1 gene, or variant thereof. In certain embodiments, the nucleic acid sequence encodes an Apaf-1 molecule lacking most, and preferably all, of the WD-40 repeats (FIG. 1).

The sequence motifs contained within Apaf-1 are related to those contained in initiator caspases which contain large prodomains. (Ahmad et al., *Cancer. Res.* 57:615–619, 1997; Boldin et al., *J. Biol. Chem.* 270:7795–7798, 1995; Chinnaiyan et al., *Cell* 81:505–512, 1995; Duan and Dixit, *Nature* 385:86–89, 1997; Zou et al., *Cell* 90:405–413, 1997). While such motifs exist in the cytochrome c-Apaf-1 signaling pathway (Li et al., *Cell* 91:479, 1997; Zou et al., *Cell* 90:405–413, 1997), studies of Apaf-1 have demonstrated that both cytochrome c and dATP are necessary for activation of caspases, such as procaspase-9 (Liu et al., *Cell* 86:147, 1996). The domains of several caspase molecules are demonstrated below.

| Caspase | Prodomain | Large Subunit | Intervening sequence | Small Subunit |
|---|---|---|---|---|
| Caspase-1 | 1–357 | 358–891 | 892–948 | 949–1212 |
| Caspase-2 | 1–456 | 457–948 | 949–990 | 991–1305 |
| Caspase-3 | 1–84 | 85–525 | | 526–831 |
| Caspase-4 | 1–240 | 241–810 | 811–867 | 868–1131 |
| Caspase-5 | 1–363 | 364–933 | | 934–1254 |
| Caspase-6 | 1–69 | 70–537 | 538–579 | 580–879 |

-continued

| Caspase | Prodomain | Large Subunit | Intervening sequence | Small Subunit |
|---|---|---|---|---|
| Caspase-7 | 1–69 | 70–594 | | 595–909 |
| Caspase-8 | 1–681 | 682–1173 | | 1174–1488 |
| Caspase-9 | 1–390 | 391–945 | 946–990 | 991–1248 |
| Caspase-10 | 1–657 | 658–1116 | | 1117–1437 |

The truncated Apaf-1 of the present invention, in one embodiment, can oligomerize with a caspase. In a further embodiment, the truncated Apaf-1 of the present invention is capable of inducing the processing of a caspase in the absence of dATP and cytochrome c.

1. Structure of Truncated Apaf-1

Full length Apaf-1 is 1194 amino acids in length. It contains an N-terminal CARD that is homologous to the CED-3 prodomain (residues 1–97), a central CED-4 homology domain (residues 98–412) and a C-terminal domain that contains 12 WD-40 repeats (residues 413–1194). The CED-4 homology domain contains Walker A and B sequences which include a P-loop sequence for nucleotide binding (residues 139–157) and a putative $Mg^{++}$ binding site (residues 228–235) (FIG. 1). Truncated Apaf-1 molecules of the present invention comprise at least a portion of CARD domain and at least a portion of the central CED-4 homology domain. In preferred embodiments, the truncated Apaf-1 also includes a portion of the 12 WD-40 repeats. In other embodiments, a truncated Apaf-1 is fused to other polypeptide sequences to aid in expression, purification, oligomerization and/or targeting. For example, fusions with His6, T7, and Flag tags may aid in purification and/or immunoidentification.

In one embodiment, truncated Apaf-1 encoding nucleic acid molecules are designed that encode amino acid residues 1 through at least 420 of SEQ ID NO:2. In a further embodiment, truncated Apaf-1 encoding nucleic acid molecules are designed that encode amino acid residues 1 through at least 530 (SEQ ID NO:2). One of skill in the art would recognize that the absolute length of the Apaf-1 is only a secondary consideration when designing a truncated form which is capable of initiating caspase processing without the presence of cytochrome c or dATP. Such constructs can be readily tested for their ability to initiate caspase processing by the assays described herein. Further, such constructs can be tested for their ability to oligomerize a caspase, (e.g., procaspase-9). Such oligomerization may be determined by a variety of means, including radiolabeling a caspase and counting the resulting complex to determine the extent of oligomer formation. Such experiments are readily performed by those of skill in the art.

2. Construction of Truncated Apaf-1

Truncated Apaf-1 molecules of the subject invention may be constructed from Apaf-1 sequences by a variety of methods known in the art. A preferred method is amplification (e.g., polymerase chain reaction (PCR)) to selectively amplify the individual regions and place these in cloning vectors such as pUC such as described in Example 1. Moreover, such PCR reactions can be performed in a variety of ways such that the primers used for amplification contain specific restriction endonuclease sites to facilitate insertion into a vector.

Further, a variety of other methodologies besides PCR may be used to attain the desired construct. For example, one skilled in the art may employ isothermal methods to amplify the nucleotide sequence of interest, using existing restriction endonuclease sites present in the nucleotide sequence to excise and insert sequences, or by the introduction of distinct restriction endonuclease sites by site-directed mutagenesis followed by excision and insertion. These and other methods are described in Sambrook et al., supra; Ausubel, et al., supra. Briefly, one methodology is to generate single-stranded cDNA of Apaf-1, followed by annealing a primer, which is complementary except for the desired alteration (e.g., a small insertion, deletion, or mutation such that a unique restriction site is created between the domains). Bacterial cells are transformed and screened for those cells which contain the desired construct. This construct is then digested to liberate the desired sequences, which can then be purified and religated into the appropriate orientation.

As indicated above, Apaf-1 nucleic acid molecules may be manipulated to contain insertions, deletions or substitutions. Moreover, such variant Apaf-1 molecules useful in the context of this invention include those which inhibit or facilitate caspase processing.

C. VECTORS, HOST CELLS AND METHODS OF EXPRESSING AND PRODUCING PROTEIN

Truncated Apaf-1 may be expressed in a variety of host organisms. In certain embodiments, truncated Apaf-1 is produced in bacteria, such as *E. coli*, or mammalian cells (e.g., CHO and COS-7), for which many expression vectors have been developed and are available. Other suitable host organisms include other bacterial species, and eukaryotes, such as yeast (e.g., *Saccharomyces cerevisiae*), and insect cells (e.g., Sf9).

In one embodiment, a DNA sequence encoding a truncated Apaf-1 is introduced into an expression vector appropriate for the host cell. In certain embodiments, truncated Apaf-1 is inserted into a vector such that a fusion protein is produced. The truncated Apaf-1 sequence is derived as described herein. As discussed above, the sequence may contain alternative codons for each amino acid with multiple codons. The alternative codons can be chosen as "optimal" for the host species. Restriction sites are typically incorporated into the primer sequences and are chosen with regard to the cloning site of the vector. If necessary, translational initiation and termination codons can be engineered into the primer sequences.

At a minimum, the vector will contain a promoter sequence. As used herein, a "promoter" refers to a nucleotide sequence that contains elements that direct the transcription of a linked gene. At a minimum, a promoter contains an RNA polymerase binding site. More typically, in eukaryotes, promoter sequences contain binding sites for other transcriptional factors that control the rate and timing of gene expression. Such sites include TATA box, CAAT box, POU box, AP1 binding site, and the like. Promoter regions may also contain enhancer elements. When a promoter is linked to a gene so as to enable transcription of the gene, it is "operatively linked".

Other regulatory sequences may be included. Such sequences include a transcription termination sequence, secretion signal sequence, origin of replication, selectable marker, and the like. The regulatory sequences are operationally associated with one another to allow transcription or translation.

The expression vectors used herein include a promoter designed for expression of the proteins in a host cell (e.g., bacterial). Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, CMV IE promoter, RSV LTR, SV40, metallothionein promoter (see, e.g., U.S. Pat. No. 4,870,009), ecdysone response element system, tetracycline-reversible silencing system (tet-on, tet-off), and the like.

The promoter controlling transcription of truncated Apaf-1 may itself be controlled by a repressor. In some systems, the promoter can be derepressed by altering the physiological conditions of the cell, for example, by the addition of a molecule that competitively binds the repressor, or by altering the temperature of the growth media. referred repressor proteins include, but are not limited to the *E. coli* lacI repressor esponsive to IPTG induction, the temperature sensitive λcI857 repressor, and the like.

In other optional embodiments, the vector also includes a transcription termination sequence. A "transcription terminator region" has either a sequence that provides a signal that terminates transcription by the polymerase that recognizes the selected promoter and/or a signal sequence for polyadenylation.

In one aspect, the vector is capable of replication in the host cells. Thus, when the host cell is a bacterium, the vector preferably contains a bacterial origin of replication. Bacterial origins of replication include the f1-ori and col E1 origins of replication, especially the ori derived from pUC plasmids. In yeast, ARS or CEN sequences can be used to assure replication. A well-used system in mammalian cells is SV40 ori.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene ($Amp^r$), tetracycline resistance gene ($Tc^r$) and the kanamycin resistance gene ($Kan^r$). The kanarnycin resistance gene is presently preferred. Suitable markers for eukaryotes usually require a complementary deficiency in the host (e.g., thymidine kinase (tk) in tk- hosts). However, drug markers are also available (e.g., G418 resistance and hygromycin resistance).

The sequence of nucleotides encoding truncated Apaf-1 may also include a secretion signal, whereby the resulting peptide is a precursor protein processed and secreted. The resulting processed protein may be recovered from the periplasmic space or the fermentation medium. Secretion signals suitable for use are widely available and are well known in the art (von Heijne, *J. Mol. Biol.* 184:99–105, 1985). Prokaryotic and eukaryotic secretion signals that are functional in *E. coli* (or other host) may be employed. The presently preferred secretion signals include, but are not limited to, those encoded by the following *E. coli* genes: pelB (Lei et al., *J. Bacteriol.* 169:4379, 1987), phoA, ompA, ompT, ompF, ompC, beta-lactamase, and alkaline phosphatase.

One skilled in the art will appreciate that there are a wide variety of suitable vectors for expression in bacterial cells and which are readily obtainable. Vectors such as the pET series (Novagen, Madison, Wis.), the tac and trc series (Pharmacia, Uppsala, Sweden), pTTQ18 (Amersham International plc, England), pACYC 177, pGEX series, and the like are suitable for expression of a truncated Apaf-1. Baculovirus vectors, such as pBlueBac (see, e.g., U.S. Pat. Nos. 5,278,050, 5,244,805, 5,243,041, 5,242,687, 5,266, 317, 4,745,051, and 5,169,784; available from nvitrogen, San Diego) may be used for expression in insect cells, such as *Spodoptera frugiperda* sf9 cells (see, U.S. Pat. No. 4,745,051). The choice of a bacterial host for he expression of a truncated Apaf-1 is dictated in part by the vector. Commercially available vectors are paired with suitable hosts.

A wide variety of suitable vectors for expression in eukaryotic cells are also available. Such vectors include pCMVLacI, pXT1 (Stratagene Cloning Systems, La Jolla, Calif.); pCDNA series, pREP series, pEBVHis (Invitrogen, Carlsbad, Calif.). In certain embodiments, the truncated Apaf-1 nucleic acid molecule is cloned into a gene targeting vector, such as pMC1neo, a pOG series vector (Stratagene Cloning Systems).

Truncated Apaf-1 may be isolated by standard methods, such as affinity chromatography, size exclusion chromatography, metal ion chromatography, ionic exchange chromatography, HPLC, and other known protein isolation methods. (see generally Ausubel et al. supra; Sambrook et al. supra). An isolated purified protein gives a single band on SDS-PAGE when stained with Coomassie blue.

Truncated Apaf-1 may be expressed as a hexa-his (His6) fusion protein and isolated by metal-containing chromatography, such as nickel-coupled beads. Briefly, a sequence encoding His6 is linked to a DNA sequence encoding a truncated Apaf-1. Although the His6 sequence can be positioned anywhere in the molecule, preferably it is linked at the 5' end or at the 3' end immediately preceding the termination codon. The fusion may be constructed by any of a variety of methods. A convenient method is amplification of the truncated Apaf-1 nucleic acid molecule using a downstream primer that contains the codons for His6. In a similar manner T7, Flag, and a variety of other fusions are possible.

Caspase proteins/polypeptides and nucleic acid molecules may be isolated, modified, and expressed by all the methods described above applicable to truncated Apaf-1. For example, nucleic acid molecules may be manipulated as previously described, to create molecules encoding caspase fusion proteins (e.g., Fc-caspase), caspase chimeras (e.g., Example 11), and other caspase variants capable of oligomerization with self, other caspase molecules, or a form of Apaf-1. In one embodiment caspases constructed such that they can oligomerize with procaspase-9 or other caspases and inhibit their processing are useful in inhibiting apoptosis. For example, a nucleic acid encoding an active site mutant caspase can be constructed such that upon introduction to a cell, the encoded product binds to and inhibits processing of or sequesters other caspases or endogenous Apaf-1, thereby inhibiting apoptosis. In a further embodiment, the prodomain of a caspase, such as caspase-9 may be introduced to a cell to inhibit apoptosis. For example, a nucleic acid molecule encoding the caspase-9 prodomain may be introduced into a cell under a constitutive promoter such that the encoded polypeptide competes with endogenous caspase-9 for endogenous Apaf-1 binding. In another embodiment, chimeric caspases or protein fusion-caspases can be constructed by standard molecular biological techniques as described by Sambrook et al., supra; Ausubel et al., supra. Briefly, the region of interest of one caspase can be cloned into a cloning vector and with the aid of restriction enzymes digested such that the nucleic acid sequence of another caspase may be fused thereto, thereby creating a chimeric nucleic acid molecule encoding a chimeric protein. The same procedure can be used to create a caspase fusion protein, however, in this case many vectors are commercially available which contain fusion constructs and allow direct cloning of the insert of interest into the vector in a simple one step process.

Purified truncated Apaf-1 protein and caspase fusion proteins may be used in assays to screen for molecules which modulate apoptosis as described in detail infra. In further embodiments, these proteins may also be crystallized and subjected to X-ray analysis to determine the 3-dimensional structure or utilized to generate antibodies.

D. USES OF TRUNCATED APAF-1 NUCLEIC ACID MOLECULES AND ENCODED PRODUCTS THEREOF

1. Identification of Inhibitors and Enhancers of Caspase Activity

Candidate inhibitors and enhancers may be isolated or procured from a variety of sources, such as bacteria, fungi, plants, parasites, libraries of chemicals, peptides or peptide derivatives and the like. Inhibitors and enhancers may be also be rationally designed, based on the protein structures determined from X-ray crystallography. In certain preferred embodiments, the inhibitor targets the Apaf-1/caspase interaction.

Without being wishing to be bound to a particular theory or held to a particular mechanism, the inhibitor may act by preventing processing of caspase or by preventing enzymatic activity, by inhibiting Apaf-1/caspase complex formation, or by other mechanisms. The inhibitor may act directly or indirectly. In preferred embodiments, inhibitors interfere in the processing of the caspase protein or the Apaf-1/caspase complex formation and/or the integrity of the complex. In other embodiments, the inhibitors are small molecules. In one embodiment, the inhibitors prevent apoptosis. Inhibitors should have a minimum of side effects and are preferably non-toxic. Inhibitors that can penetrate cells are preferred.

In addition, enhancers of caspase processing activity or expression are desirable in certain circumstances. At times, increasing apoptosis will have a herapeutic effect. For example, tumors or cells that mediate autoimmune diseases are appropriate cells for destruction. Enhancers may increase the rate or efficiency of caspase processing, increase transcription or translation, or act through other mechanisms. As will be apparent to those skilled in the art, many of the guidelines presented above apply to the design of enhancers as well. Within the context of the present invention truncated Apaf-1 itself can act as an enhancer. Further, other compounds which facilitate caspase oligomerization are reasonably expected to enhance apoptosis. For example, caspase proteins fused to Fc domains, FKBP (FK506 binding protein), or the like can form oligomers which lead to caspase activation (e.g., Example 8).

Screening assays for inhibitors and enhancers will vary according to the type of inhibitor or enhancer and the nature of the activity that is being affected. Assays may be performed in vitro or in vivo. In general, in vitro assays are designed to evaluate caspase protein processing or caspase enzymatic activity, and in vivo assays are designed to evaluate caspase protein processing, caspase enzymatic activity, apoptosis, or caspase cleavage of substrate. In any of the assays, a statistically significant increase or decrease compared to a proper control is indicative of enhancement or inhibition. In one embodiment, the caspase utilized for the assays is procaspase-9.

One in vitro assay can be performed by examining the effect of a candidate compound on processing of a caspase into two subunits. Briefly, a caspase, that is a primary translation product, is obtained from an in vitro translation system. The caspase is preferably constructed to be capable of normal auto-processing, but can be constructed so that the caspase self-oligomerizes, thereby inducing auto-processing. As mentioned above, self-oligomerization may be achieved by creating a fusion with the caspase and a domain known to self associate, such as an Fc domain. Further, chimeric caspase constructs can be created such that the domain responsible for oligomerization in one caspase is transferred to another (e.g., see EXAMPLE 11). Such chimeric constructs can be readily tested for self, Apaf-1, or truncated Apaf-1 oligomerization by known methods of detecting protein-protein binding. For example, one can utilize sedimentation analysis, electrophoretic gel shift analysis, radiolabeled binding studies, and the like. In addition, if the primary in vitro translation product is constructed to self-oligomerize, it is contacted with or without, or translated in the presence or absence of, a candidate compound and assessed for appearance of the two subunits. Further, to facilitate detection, typically the in vitro translation product is labeled during translation. Alternatively, truncated Apaf-1 can be contacted with a caspase (typically, in vitro translated in the presence of a label) in the presence or absence of a candidate compound and the processing of the caspase assessed by the appearance of the two caspase subunits. The two subunits may be readily detected by autoradiography after gel electrophoresis. One skilled in the art will recognize that other methods of labeling and detection may be used alternatively.

An alternative in vitro assay is designed to measure cleavage of a caspase substrate (e.g., Acetyl DEVD-aminomethyl coumarin (amc), lamin, PRPP, PARP, and the like). Substrate turnover by the caspase of interest may be assayed which will provide data as to the degree of processing of the caspase. Briefly, in this method, the caspase is translated and allowed sufficient time to oligomerize in the presence or absence of a candidate compound. As described above, the oligomerization may occur by having truncated Apaf-1 in the mixture or constructing self-oligomerizing caspases as previously described. The caspase substrate is then added to the reaction. Detection of cleaved substrate is performed by any one of a variety of standard methods. Generally, the substrate will be labeled and followed by an appropriate detection means.

Moreover, any known enzymatic analysis can be used to follow the inhibitory or enhancing ability of a candidate compound with regard to the ability of self-oligomerizing caspases or truncated Apaf-1/caspase complexes to produce enzymatically active caspases. For example, one could express a self-oligomerizing caspase construct or a truncated Apaf-1 construct of interest in a cell line, be it bacterial, insect, mammalian or other, and purify the resulting polypeptide. The purified truncated Apaf-1 or self-oligomerizing caspase could then be used in a variety of assays to follow its ability to facilitate processing or catalytic ability in the presence of candidate compounds, as noted above. Such methods of expressing and purifying recombinant proteins are known in the art and examples can be found in Sambrook et al., *Molecular Cloning: A Laboratory Manual*, Cold Spring Harbor Press, 1989 as well as in a number of other sources.

In vivo assays are typically performed in cells transfected either transiently or stably with an expression vector containing truncated Apaf-1 nucleic acid molecule or a self-oligomerizing caspase nucleic acid molecule, such as those described herein. These cells are used to measure caspase processing, substrate turnover, or apoptosis in the presence or absence of a candidate compound. When assaying apoptosis, a variety of cell analyses may be used including, for example, dye staining and microscopy to examine nucleic acid fragmentation and porosity of the cells. Further, in vivo assaying for the ability of the transfected self-oligomerizing caspases to cleave known substrates or truncated Apaf-1 to facilitate cleavage of native caspases can be performed by co-transfecting known substrates or placing these substrates in the cell culture media in the presence of the candidate compound thereby allowing for the detection and determination of substrate turnover.

The assays briefly described herein may be used to identify an enhancer or inhibitor that is specific for an individual caspase or for the Apaf-1/caspase interaction.

A variety of methodologies exist that can be used to investigate the effect of a candidate compound. Such methodologies are those commonly used to analyze enzymatic reactions and include, for example, SDS-PAGE, spectroscopy, HPLC analysis, autoradiography, chemiluminescence, chromogenic reactions, and immunochemistry (e.g., blotting, precipitating, etc.).

2. Uses of Inhibitors and Enhancers

Inhibitors and enhancers may also be used in the context of this invention to exert control over the cell death process or cytokine activation (e.g., IL-1, which is activated by caspase-1). Thus, these inhibitors and enhancers will have utility in diseases characterized by either excessive or insufficient levels of apoptosis. Inhibitors of caspase activation may be used to treat the major neurodegenerative diseases: stroke, Parkinson's Disease, Alzheimers Disease, and ALS. As well, caspase activation inhibitors may be used to inhibit apoptosis in the heart following myocardial infarction, in the kidney following acute ischemia, and in diseases of the liver. Enhancers of caspase activation may be used in contexts where apoptosis or cytokine activation are desired. For example, inducing or increasing apoptosis in cancer cells or aberrantly proliferating cells may be effected by delivery of a caspase enhancer. In this regard truncated Apaf-1 and self-oligomerizing caspases (e.g., procaspase-9), themselves, can function as enhancers of apoptosis when introduced into a cell.

Further embodiments include the inhibition of neoplasia or apoptosis by utilizing specific antisense polynucleotides complementary to all or part of the nucleic acid sequence SEQ ID NO:1 encoding truncated Apaf-1 or the nucleic acid sequence SEQ ID NO:3 encoding caspase-9. Such complementary antisense polynucleotides may include substitutions, additions, deletions, or transpositions, as long as specific hybridization to the relevant target sequence in SEQ ID NO:1 or SEQ ID NO:3 is retained as a functional property of the polynucleotide. Antisense polynucleotides that prevent transcription and/or translation of mRNA corresponding to caspase-9 and Apaf-1 may inhibit apoptosis. Antisense polynucleotides of various lengths may be produced and used, however, the sequence length is typically at least 20 consecutive nucleotides that are substantially or wholly identical the sequence of SEQ ID NO:1 or SEQ ID NO:3. (see U.S. Pat. No. 5,691,179 and *Antisense RNA and DNA*, D. A. Melton, Ed., Cold Spring Harbor Laboratory, Cold Spring Harbor, N.Y. 1988, each of which is incorporated herein by reference).

The inhibitors and enhancers may be further coupled with a targeting moiety that binds a cell surface receptor specific to the cells. Administration of inhibitors or enhancers will generally follow established protocols. The compositions of the present invention may be administered either alone, or as a pharmaceutical composition. Briefly, pharmaceutical compositions of the present invention may comprise one or more of the inhibitors or enhancers as described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration. One skilled in the art may further formulate the enhancers or inhibitors of this invention in an appropriate manner, and in accordance with accepted practices, such as those disclosed in *Remington's Pharmaceutical Sciences*, Gennaro, Ed., Mack Publishing Co., Easton, Pa. 1990.

3. Gene Therapy

As noted above, truncated Apaf-1 or self-oligomerizing caspases may be delivered to cells in combination with gene delivery vehicles. In many diseases and syndromes, insufficient apoptosis is an important feature in their development. Treatment of many autoimmune diseases and tumors would benefit from increased apoptosis. One means to increase apoptosis is to provide target cells with self-oligomerizing caspase nucleic acid molecules in an expressible and form. Alternatively, one may provide target cells with truncated Apaf-1 nucleic acid molecules in an expressible form. These methods may be accomplished by delivery of DNA or cDNA capable of in vivo transcription of either the truncated Apaf-1 or the self-oligomerizing caspase. More specifically, in order to produce either truncated Apaf-1 or self-oligomerizing caspases in vivo, a nucleic acid sequence coding for either is placed under the control of a eukaryotic promoter (e.g., a pol III promoter, CMV or SV40 promoter). Where it is desired to more specifically control transcription, the truncated Apaf-1 or self-oligomerizing caspase may be placed under the control of a tissue or cell specific promoter (e.g., to target cells in the liver), or an inducible promoter, such as MMTV LTR, CMV IE promoter, RSV LTR, SV40, metallothionein promoter (see, e.g., U.S. Pat. No. 4,870,009), ecdysone response element system, tetracycline-reversible silencing system (tet-on, tet-off), and the like.

Many techniques for introduction of nucleic acids into cells are known. Such methods include retroviral vectors and subsequent retrovirus infection, adenoviral or adeno-associated viral vectors and subsequent infection, and complexes of nucleic acid with a condensing agent (e.g., polylysine). These complexes or viral vectors may be targeted to particular cell types by way of a ligand incorporated into the vehicle. Many ligands specific for tumor cells and other cells are well known in the art.

A wide variety of vectors may be utilized within the context of the present invention, including for example, plasmids, viruses, retrotransposons and cosmids. Representative examples include adenoviral vectors (e.g., WO 94/26914, WO 93/9191; Yei et al., *Gene Therapy* 1:192–200, 1994; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10):1287–1291, 1993), adeno-associated type 1 ("AAV-1") or adeno-associated type 2 ("AAV-2") vectors (see WO 95/13365; Flotte et al., *PNAS* 90(22):10613–10617, 1993), hepatitis delta vectors, live, attenuated delta viruses and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218.

Within certain aspects of the invention, nucleic acid molecules that encode truncated Apaf-1 or self-oligomerizing caspases may be introduced into a host cell utilizing a gene delivery vehicle, or by various physical methods. Representative examples of such methods include transformation using calcium phosphate precipitation (Dubensky et al., *PNAS* 81:7529–7533, 1984), direct microinjection of such nucleic acid molecules into intact target cells (Acsadi et al., *Nature* 352:815–818, 1991), and electroporation whereby cells suspended in a conducting solution are subjected to an intense electric field in order to transiently polarize the membrane, allowing entry of the nucleic acid molecules. Other procedures include the use of. nucleic acid molecules linked to an inactive adenovirus (Cotton et al., *PNAS* 89:6094, 1990), lipofection (Felgner et al, *Proc. Natl. Acad. Sci. USA* 84:7413–7417, 1989), microprojectile bombardment (Williams et al., *PNAS* 88:2726–2730, 1991), polycation compounds such as polylysine, receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., *Pharmac. Ther.* 29:69, 1985; and Friedmann et al., *Science* 244:1275, 1989), and DNA ligand (Wu et al., *J. Biol. Chem.* 264:16985–16987, 1989), as well as psoralen inactivated viruses such as Sendai or Adenovirus. In one embodiment, the truncated Apaf-1 or self-oligomerizing caspase construct is introduced into the host cell using a liposome.

As noted above, pharmaceutical compositions also are provided by this invention. These compositions may contain any of the above described inhibitors, enhancers, DNA molecules, vectors or host cells, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes, including for example intraarticularly, intracranially, intradermally, intrahepatically, intramuscularly, intraocularly, intraperitoneally, intrathecally, intravenously, subcutaneously or even directly into a tumor. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition. Pharmaceutical compositions are useful for both diagnostic or therapeutic purposes.

Pharmaceutical compositions of the present invention may be administered in a manner appropriate to the disease to be treated (or prevented). The quantity and frequency of administration will be determined by such factors as the condition of the patient, and the type and severity of the patient's disease. Dosages may be determined most accurately during clinical trials. Patients may be monitored for therapeutic effectiveness by appropriate technology, including signs of clinical exacerbation, imaging and the like.

The following examples are offered by way of illustration, and not by way of limitation.

EXAMPLES

Example 1

GENERATION OF cDNA EXPRESSION CONSTRUCTS cDNAs encoding truncated or mutated Apaf-1 variants were generated by PCR and subcloned into the bacterial expression vectors pET-28a or pET-21b (Invitrogen). Recombinant proteins with C-terminal His6 tags were expressed in BL-21 DE3 bacteria and purified by affinity purification on a $Ni^{2+}$-affinity resin. Constructs encoding wild type (WT) or mutant caspase-9, procaspase-3, Apaf-1, DR4, DR5 or Bcl-$x_L$ have been described previously (Hegde et al., *J. Biol. Chem.*, 273:7783–7786, 1998; Li et al., *Cell* 91:479–489, (1997); MacFarlane et al., *J. Biol. Chem.*, 272:25417–25420, 1997; Srinivasula et al., *J. Biol. Chem.*, 271:27099–27106, 1996). Constructs encoding T7- or Flag-epitope tagged proteins were made by cloning cDNAs of the respective genes in frame into the mammalian expression vectors T7-pcDNA3 or pFLAG-CMV-2.

Primers used for truncated form amplification are provided below:

APAF-530
　Bam-ATG primer (SEQ ID NO:4): CGGGATC-CGATGGATGCAAAAGCTCG
　530Xho-end primer (SEQ ID NO:5): CCGCTC-GAGCTCACTGACTGCACAATCCTTTTC APAF-420
　Bam-ATG primer (SEQ ID NO:4): CGGGATC-CGATGGATGCAAAAGCTCG
　420Xho-end primer (SEQ ID NO:6): CCGCTC-GAGCTTTCCATTCCGATCACAG APAF-350
　Bam-ATG primer (SEQ ID NO:4): CGGGATC-CGATGGATGCAAAAGCTCG
　Aplice Xho-end primer (SEQ ID NO:7): CGCCTC-GAGGCCTTTACATTCTTTTATAATAC APAF-97
　Bam-ATG primer (SEQ ID NO:4): CGGGATC-CGATGGATGCAAAAGCTCG
　H Domain Xho-end primer (SEQ ID NO:8): CGCCTC-GAGGGAAGAAGAGACAACAGG APAF-530ΔCARD
　ΔCARD-Bam-Start primer (SEQ ID NO:9): CGCG-GATCCAGTGTAAGGACAGTCCTG
　530Xho-end primer (SEQ ID NO:5): CCGCTC-GAGCTCACTGACTGCACAATCCTTTTC APAF-WD
　APAF-WD start primer (SEQ ID NO:10): CGGGATC-CATGGAGAATTTTCAGGAGTTTTTATC
　APAF-Xho-end primer (SEQ ID NO:11): CGCCTC-GAGTTCTAAAGTCTG-TAAAATATATAAAATACC Example 2

IN VITRO CASPASE 9 ACTIVATION ASSAY

Figure 2A:
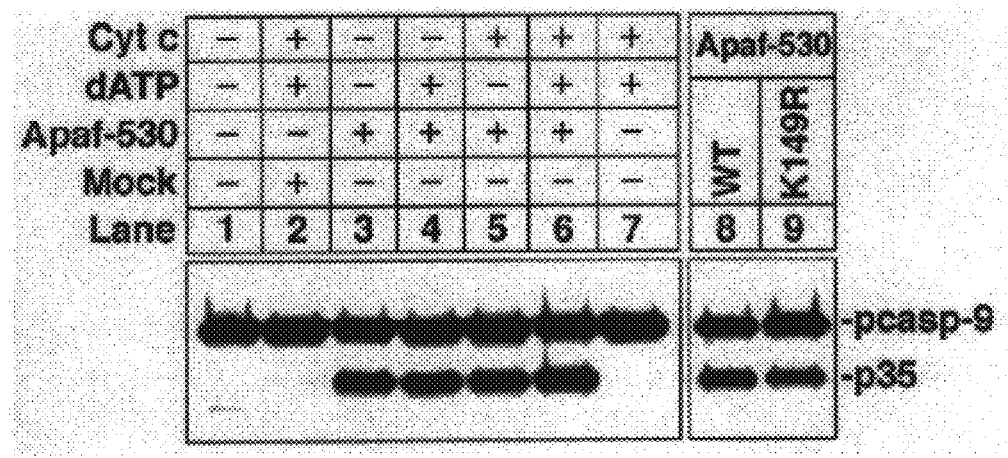
FIGS. 2A and 2B are scanned images representing SDS-PAGE analysis of the processing of procaspase-9 either by truncated Apaf-530 in the presence and absence of cytochrome c and dATP (2A imaged by autoradiogram) or truncated forms of Apaf-1 (2B upper panel imaged by autoradiogram, lower panel imaged by immunoblot).
Figure 2B:
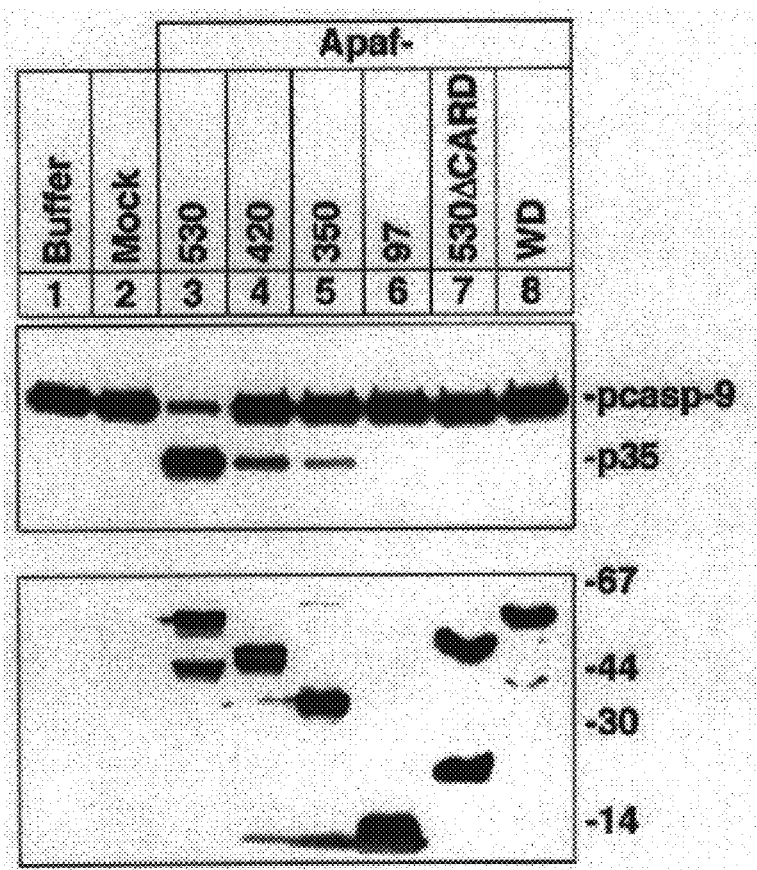

Affinity purified Apaf-1 variants were incubated (2 h) with in vitro translated WT or mutant procaspase-9 in buffer A (20 mM HEPES, pH 7.5, 10 mM KCl, 1.5 mM $MgCl_2$, 1 mM EDTA, 1 mM EGTA, 1 mM DTT, 0.1 mM PMSF) in the presence or absence of cytochrome c and/or dATP. SDS sample buffer was then added to each sample, boiled and subjected to SDS-PAGE analysis followed by autoradiography. In FIG. 2A procaspase-9 was in vitro translated in the presence of $^{35}S$-methionine. Following translation procaspase-9 was desalted by gel filtration through a biospin column (BioRad) to remove unincorporated methionine and free nucleotides. Desalted procaspase-9 was then incubated with 200 ng $Ni^{2+}$-affinity purified bacterially expressed recombinant Apaf-530 (WT or K149R mutant) in the presence or absence of cytochrome c or dATP or both for 2 h at 30° C. A mock sample containing $Ni^{2+}$-affinity purified material from bacteria transformed with an empty vector was used as a negative control. Following incubation the products were analyzed by SDS-PAGE and autoradiography. In FIG. 2B $^{35}S$-labeled procaspase-9 (as described above) was incubated with bacterial lysates containing truncated Apaf-1 variants as indicated and then analyzed as above (2B upper panel). The bacterial lysates were analyzed by SDS-PAGE and immunoblotted with an Apaf-1 antibody which recognizes the N-terminus of Apaf-1 (lanes 2–6) and an anti T7-tag antibody (lanes 7–8) to confirm expression and equivalent concentration of the different Apaf-1 variants (2B lowerpanel). The molecular mass markers are indicated to the right of the lower panel.

$^{35}S$-labeled caspases were obtained by in vitro translation in the presence of $^{35}S$-methionine using a coupled transcription/translation system in rabbit reticulocyte lysate using TNT Kit (Promega) according to the manufacturer's recommendations.

Example 3

EXPRESSION OF TRUNCATED APAF-1 CONSTRUCTS IN MAMMALIAN CELLS AND ASSAY FOR APOPTOSIS

To express the caspases or truncated Apaf-1 in mammalian cells and assay their apoptotic activity, they were amplified with the T7-tag primer and reverse primers using the pET28a constructs as templates, and subcloned into the mammalian double expression vector pRSC-LacZ (MacFarlane et al., *J. Biol. Chem.*, 272:25417–25420, 1997; Tsang et al., *Bio/Technology*, 22:68, 1997) or as previously described (Li et al., *Cell* 91:479–489, 1997; Srinivasula et al., *J. Biol. Chem.*, 272:18452–18545, 1997). This vector allows the expression of lacZ under the Rous Sarcoma virus promoter, and the test cDNA under the CMV promoter. To assay for apoptosis, MCF-7 or 293 cells were transfected, using the method commercially available as the Lipofect Amine method (Life Technologies, Inc.), with the pRSC-LacZ constructs in the presence or absence of different apoptosis-inhibitors. 30 h after transfection cells were stained with β-galactosidase and examined for morphological signs of apoptosis. The percentage of round blue apoptotic cells (mean±SD) were determined by phase contrast microscopy and then represented as a function of total blue cells under each condition (n≧3).

Example 4

TRUNCATED APAF-1 WITHOUT ITS WD REPEATS FUNCTIONS INDEPENDENT OF CYTOCHROME C AND DATP

To determine the role of the WD-40 repeat in the mechanism of Apaf-1-induced processing of procaspase-9, truncated Apaf-1 (Apaf-530) lacking its WD-40 repeats (FIG. 1) was expressed and purified. To reconstitute a recombinant caspase-9 activation system, the truncated Apaf-530 was incubated with in vitro translated recombinant procaspase-9 in the presence or absence of cytochrome c and dATP. Unlike previous observations with the full length native Apaf-1 (Li et al., Cell 91:479–489, 1997), recombinant Apaf-530 was able to promote processing of procaspase-9 to produce a 35 kDa fragment (p35) in the absence of cytochrome c or dATP (FIG. 2A). It was previously shown that mutation of CED-4 K165R which is required for nucleotide binding destroys its activity (Chinnaiyan et al., Nature 388:728–729, 1997; Jarnes et al., Curr. Biol. 7:246–252, 1997; Seshagiri and Miller, Curr. Biol. 7:455–460, 1997). Interestingly, a similar mutation in Apaf-1 (K149R) slightly reduced but did not inhibit the activity of recombinant Apaf-530 (FIG. 2A). These observations suggest that the WD-40 repeats may exert a dominant negative effect on the activity of Apaf-1. Therefore, either binding of Apaf-1 to cytochrome c and dATP or deletion of the repeats could induce a conformational change enabling Apaf-1 to bind and process procaspase-9.

To determine the minimal sequence of Apaf-1 that is able to promote activation of procaspase-9, reconstitution experiments were performed with several truncated recombinant Apaf-1 variants (FIG. 1). As shown in FIG. 2B, Apaf-420 (residues 1–420) which contains the minimal conserved sequence between Apaf-1 and CED-4, produced nearly 90% less activity than Apaf-530 (lane 4). Further deletions in the CED-4 homology region of Apaf-1 (Apaf-350, residues 1–350) further reduced its activity (lane 5). Deletion of the entire CED-4 homology region (Apaf-97, residues 1–97) or the CARD domain of Apaf-1 (Apaf-53OΔCARD, residues 98–530), inactivated Apaf-1 (lanes 6 and 7). The WD-40 repeat region (Apaf-WD, residues 530–1194) was also inactive (lane 8). Therefore, a portion of the CED-4 homology region of Apaf-1 and at least a portion of its CARD domain are required for its activity.

Example 5

PROCESSING OF PROCASPASE-9 BY APAF-530 OCCURS BY AUTOCATALYSIS

To map the exact processing site(s) in procaspase-9 and to determine whether processing of procaspase-9 occurs by autocatalysis, two potential processing sites (Asp315 and Asp330) and the active site Cys287 were mutated. If processing occurs at these sites by autocatalysis, then mutation of the processing sites or the active site C287 should prevent processing. To investigate this processing event, the Apaf-530 reconstitution system was utilized.

Figure 3:
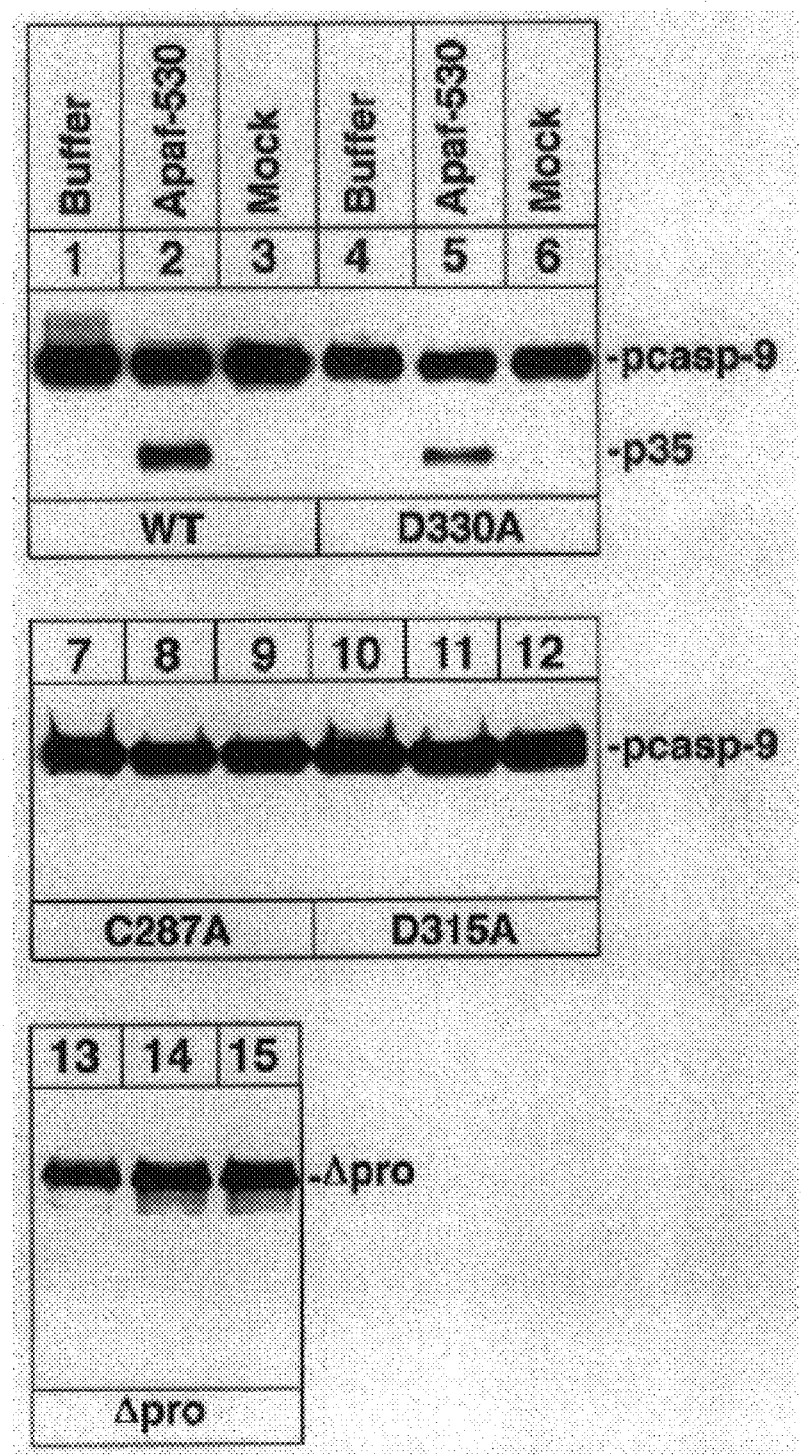
FIG. 3 is a scanned image of an autoradiogram representing SDS-PAGE analysis of Apaf-530 mediated procaspase-9 autoprocessing at Asp315.

In FIG. 3, $^{35}$S-labeled WT or mutant D330A, D315A or C287A mutants of procaspase-9 or prodomainless procaspase-9 (Δpro, residues 134–416) were incubated with buffer (lanes 1, 4, 7, 10, 13), purified Apaf-530 (lanes 2, 5, 8, 11, 14) or mock purified material (lanes, 3, 6, 9, 12, 15) and then analyzed by SDS-PAGE and autoradiography.

As demonstrated by FIG. 3, incubation of Apaf-530 with WT or D330A mutant procaspase-9 produced the p35 fragment (lanes 2 and 5). However, Apaf-530 was unable to process the D315A mutant procaspase-9 indicating that processing occurs at Asp315 (lane 11). Therefore, Apaf-1 triggers processing of procaspase-9 only at Asp315. Apaf-530 was also unable to promote processing of the procaspase-9 active site C287A mutant (lane 8), suggesting that Apaf-1 does not have a proteolytic activity capable of processing procaspase-9. Hence, Apaf-1-mediated processing of procaspase-9 is an intrinsic activity of procaspase-9 itself and occurs by autocatalysis.

The prodomain of caspase-9 is also necessary for activation of procaspase-9 by Apaf-530. Deletion of this domain prevented processing of procaspase-9 (FIG. 3, lane 14). Taken together these data demonstrate that interaction of procaspase-9 with Apaf-1 through-its prodomain induces it to undergo autoproteolytic processing at Asp315.

Example 6

PROCASPASE-9 PROCESSING IN THE CYTOCHROME C/ APAF-1-DEPENDENT PATHWAY

Figure 4:
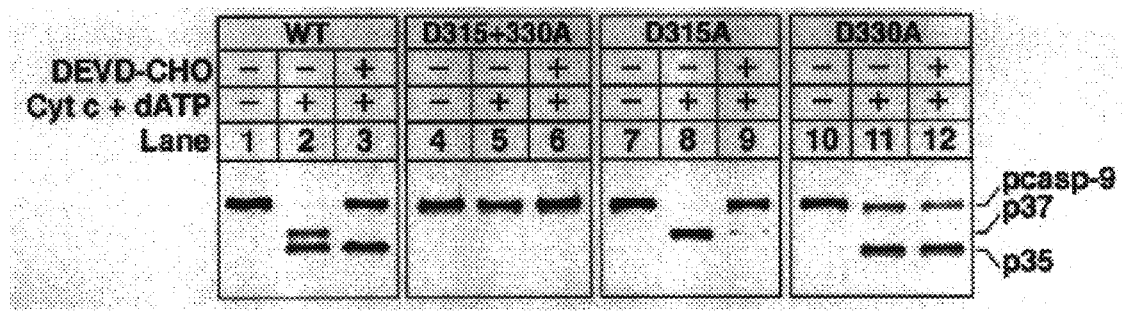
FIG. 4 is a scanned image of an autoradiogram representing SDS-PAGE analysis of cytochrome c/dATP-dependent processing of mutant forms of procaspase-9 in 293 cellular extracts.

To study processing of procaspase-9 in the cytochrome c/Apaf-1-dependent pathway, WT and the Asp to Ala mutants of procaspase-9 were incubated with a cellular S100 extract in the presence or absence of cytochrome c and dATP. As illustrated in FIG. 4, $^{35}$S-labeled WT (lanes 1–3) or mutant D315A+D330A (lanes 4–6), D315A (lanes 7–9), D330A (lanes 10–12) procaspase-9 were incubated with S100 extract from 293 cells in the presence or absence of cytochrome c plus dATP or DEVD-CHO (a caspase-3 and -7 inhibitor), or both for 1 h at 30° C. Samples were then analyzed by SDS-PAGE and autoradiography.

FIG. 4 demonstrates that cytochrome c and dATP induced processing of WT procaspase-9 to generate a 37 kDa fragment (p37) and a 35 kDa fragment (P35) (lane 2). Further, cytochrome c and dATP were unable to induce processing of the double mutant Asp315+330 (lane 5). However, they were able to induce processing of the Asp315 or Asp330 mutants to generate a p37 (lane 8) or a p35 (lane 11) fragment, respectively. This confirms that processing at Asp315 produces the p35 fragment, whereas processing at Asp330 produces the p37 fragment. Interestingly, processing at Asp330 (lanes 3 and 9) but not at Asp315 (lanes 3 and 12) was sensitive to inhibition by DEVD-CHO (Asp-Glu-Val-Asp-aldehyde). Since processing at Asp315 activates caspase-9 which directly activates the downstream caspase-3, the processing at Asp330 must be attributed to activated caspase-3 that is potently inhibited by DEVD-CHO.

Figure 5:
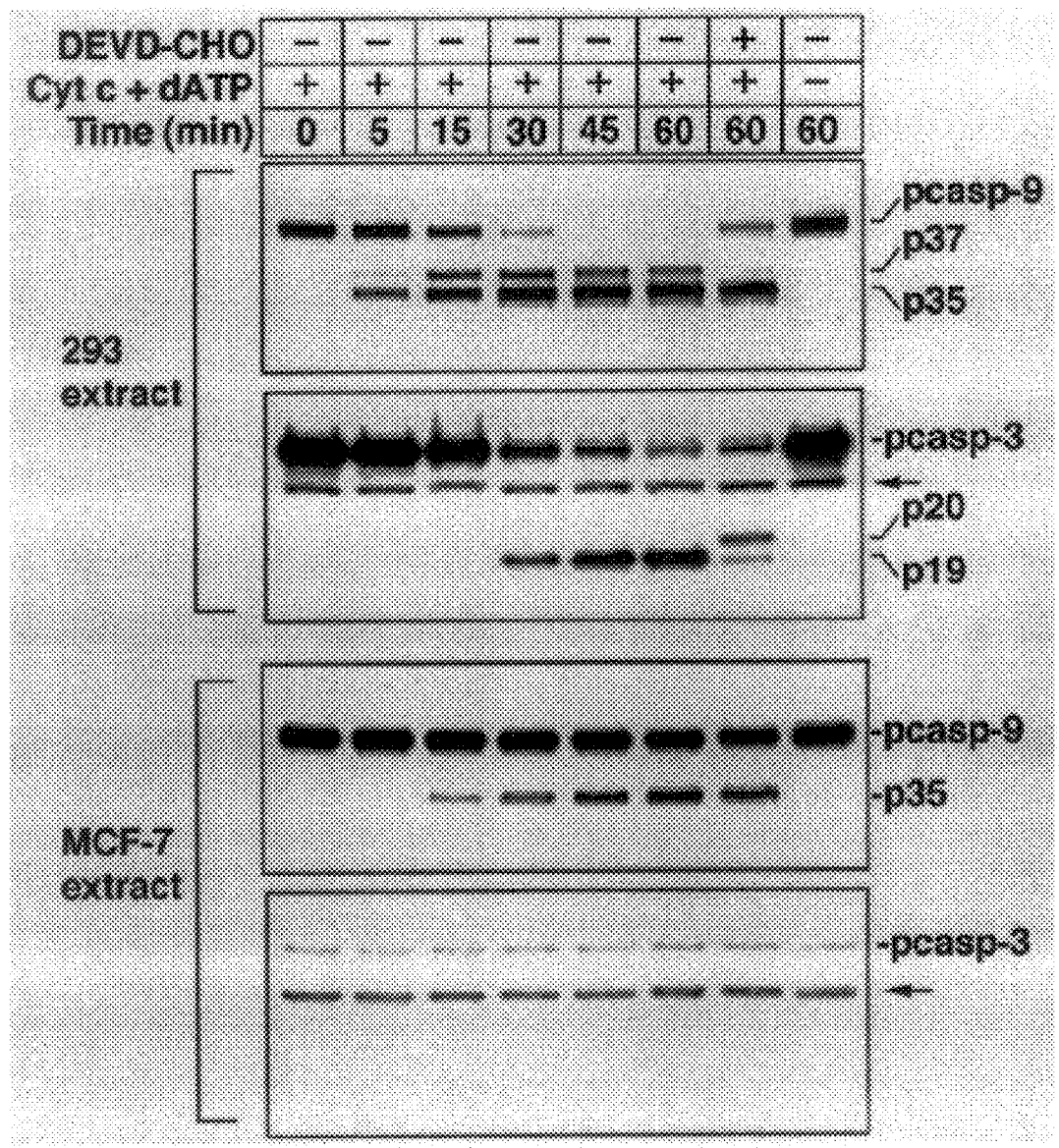
FIG. 5 is a scanned image of an autoradiogram representing SDS-PAGE analysis cytochrome c/dATP-dependent processing of procaspase-9 and procaspase-3 in 293 and MCF-7 cellular extracts as a function of incubation time.

To confirm this, a time course analysis of procaspase-9 and procaspase-3 processing was performed in cellular S100 extracts from 293 and MCF-7 cells. Extracts from these two cell lines were used because the 293 cells express procaspase-3 whereas the MCF-7 do not (Li et al., J. Biol. Chem. 272:30299–30305, 1997). As illustrated in FIG. 5, $^{35}$S-labeled WT procaspase-9 was incubated with S100 extracts from 293 or MCF-7 cells in the presence or absence of cytochrome c/dATP or DEVD-CHO, or both. At the indicated times the reactions were stopped and then analyzed by SDS-PAGE and autoradiography (procaspase-9 panels) or Western blot analysis using anti-caspase-3 p20 polyclonal antibody (procaspase-3 panels). Small arrows indicate a non-specific band detected by the anti-caspase-3 antibody.

As shown in FIG. 5, in the 293 S100 extract, processing at Asp315 and Asp330 did not occur simultaneously. The autocatalytically generated p35 fragment was detected within the first 5 min (FIG. 5, lane 2, 293-upper panel). Ten minutes later the p37 fragment was detectable and its appearance coincided with the activation of caspase-3 (FIG. 5, lanes 3–6, 293-lower panel). In the presence of DEVD-CHO, both the generation of caspase-9-p37 fragment and the autoconversion of caspase-3-p20 to p19 were blocked (lane 7), indicating that active caspase-3 is responsible for generation of the p37 fragment. Nevertheless, DEVD-CHO did not block the autocatalytic generation of the p35 fragment, but it slightly attenuated processing of procaspase-3 (lane 7). These data are consistent with our previous observation that caspase-9 is upstream of caspase-3 and is responsible for its activation in the cytochrome c-dependent pathway (Li et al., 1997b). However, once procaspase-3 is activated by caspase-9 it feeds back on the remaining procaspase-9 and cleaves it at Asp330 to generate more active caspase-9 thus amplifying the caspase cascade.

Figure 6:
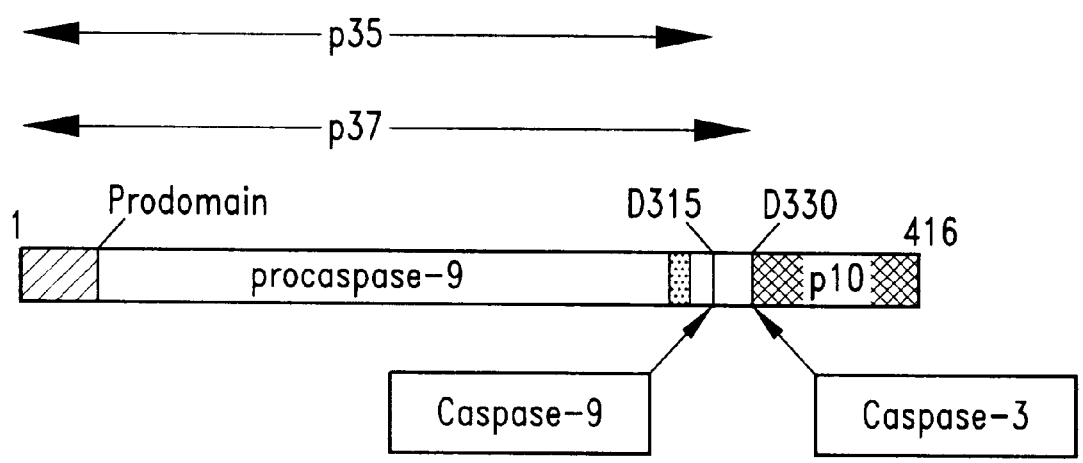
FIG. 6 is a schematic representation of full length procaspase-9, illustrating the sites of processing by caspase-9 and -3 and the resulting fragments.

In the MCF-7 extract, activation by cytochrome c and dATP generated only the p35 fragment and no p37 fragment was seen (FIG. 5, MCF-7-upper panel). Also Western blot analysis revealed a very faint caspase-3 reactive species in these extracts (FIG. 5, MCF-7-lower panel). This is consistent with previous observations that MCF-7 cells lack or contain negligible amount of procaspase-3 (Li et al., *J. Biol. Chem.*, 272:30299–30305, 1997). This confirms that processing of procaspase-9 at Asp330 is an activity of the executioner caspase-3 (FIG. 6).

Example 7

CASPASE-9 CAN ALSO PROCESS PROCASPASE-7 BUT NOT PROCASPASE-6

To test the activity of caspase-9 towards precursors of the other executioner caspases, namely procaspase-6 and -7, purified recombinant mature caspase-9 was incubated with $^{35}$S-labeled procaspase-3 (FIG. 7, lane 2), procaspase-6 (FIG. 7, lane 4) or procaspase-7 (FIG. 7, lane 6) for 1h at 37° C. and analyzed by SDS-PAGE and autoradiography.

Figure 7:
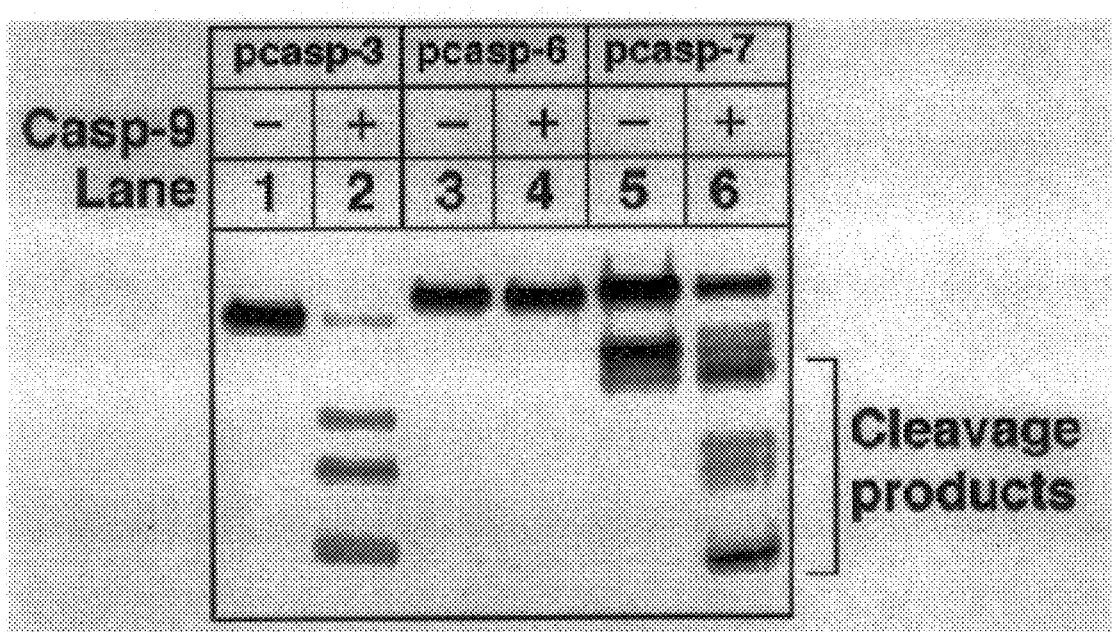
FIG. 7 is a scanned image of an autoradiogram representing SDS-PAGE analysis of caspase-9 processing of procaspase-3, procaspase-6, and procaspase-7.
Figure 8:
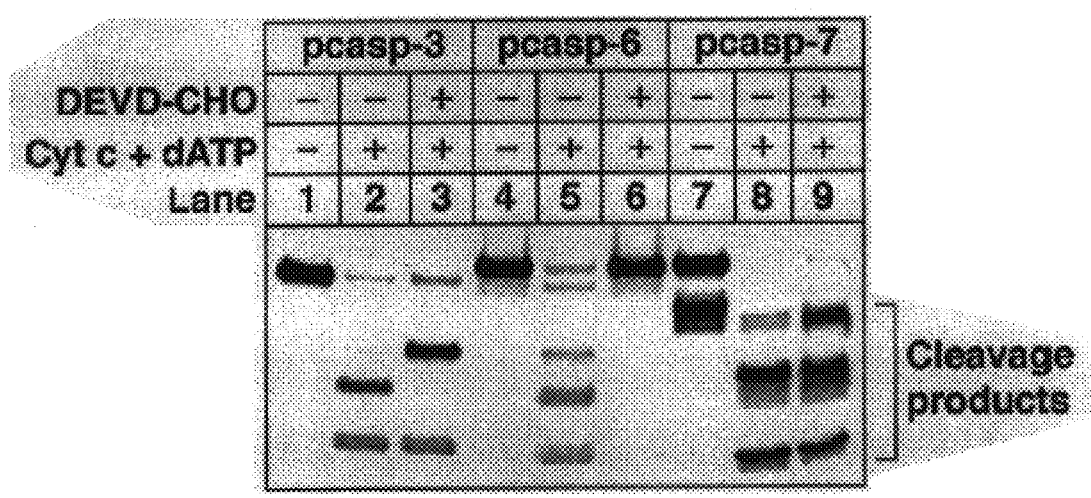
FIG. 8 is a scanned image of an autoradiogram representing SDS-PAGE analysis of processing of procaspase-3, procaspase-6, and procaspase-7 in the cell extracts.

As shown in FIG. 7, caspase-9 was able to process procaspase-3 (lane 2) and procaspase-7 (lane 6), but not procaspase-6 (lane 4), to the corresponding large and small subunit fragments. Interestingly, all three caspases underwent processing in the 293 S100 extracts, when these extracts were stimulated with cytochrome c and dATP (FIG. 8). In FIG. 8, $^{35}$S-labeled procaspase-3, -6 or -7 were incubated with S100 extracts from 293 cells in the presence or absence of cytochrome c/dATP or DEVD-CHO, or both and analyzed by SDS-PAGE followed by autoradiography. However, when DEVD-CHO was included, processing of procaspase-6 (lane 6), but not procaspase-3 (lane 3) or -7 (lane 9) was inhibited. Since the activity of both caspase-3 and -7, but not caspase-9, are potently inhibited by DEVD-CHO, it follows that either caspase-3 or -7 are responsible for processing of procaspase-6. Also, since caspase-7 cannot process procaspase-6 (Srinivasula et al., *J. Biol. Chem.* 271:27099–27106, 1996), caspase-3 is the one responsible for processing of procaspase-6 in the cytochrome c plus dATP-dependent pathway.

Example 8

ACTIVATION OF PROCASPASE-9 BY HETEROLOGOUS OLIGOMERIZATION

Figure 9:
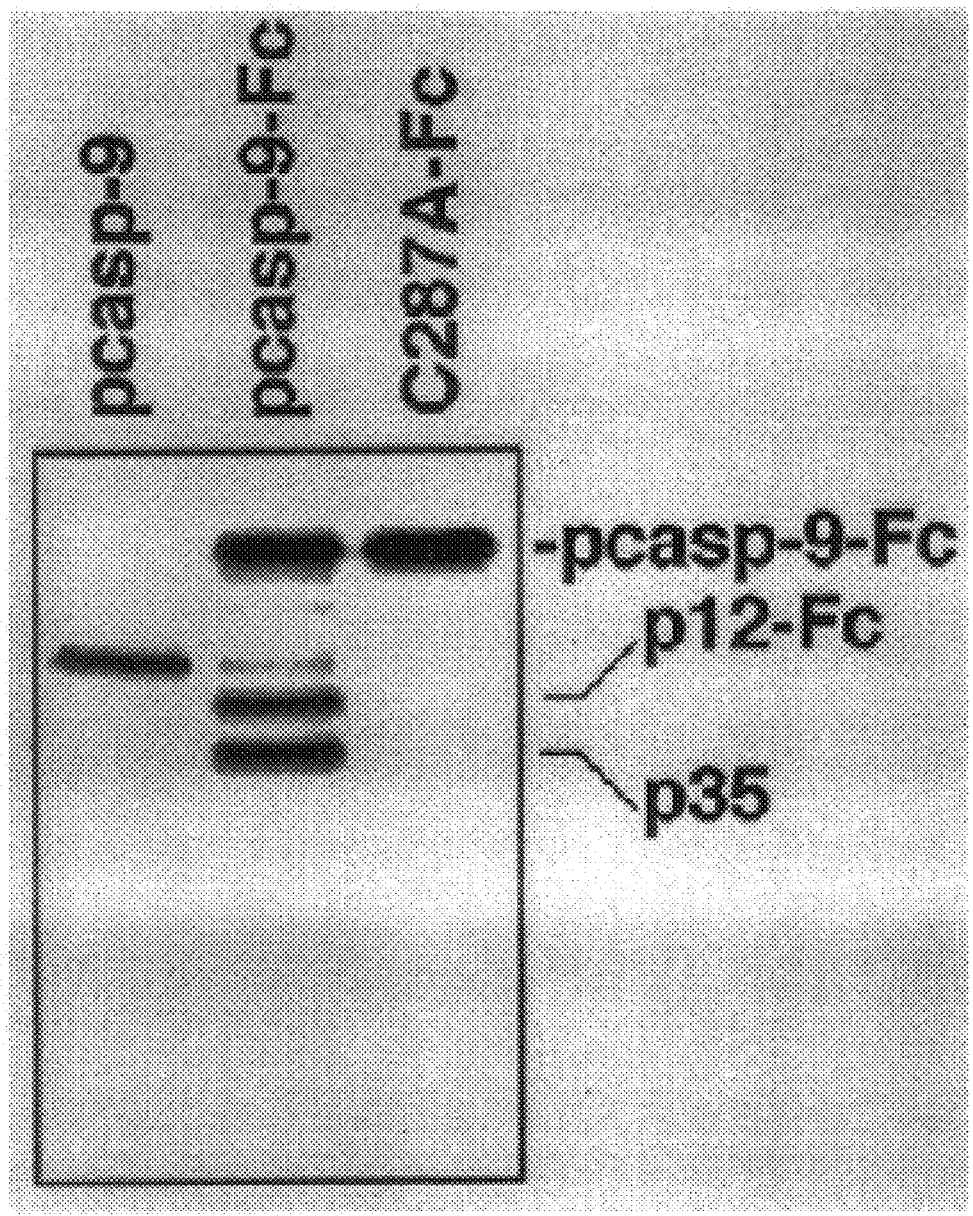
FIG. 9 is a scanned image of an autoradiogram representing SDS-PAGE analysis of in vitro translated WT procaspase-9 and Fc-fusion procaspase-9 variants.

Artificially-induced oligomerization of procaspase-1 or procaspase-8 by overexpression or by heterologous-inducible oligomerization systems causes their autocatalytic processing/activation (Gu et al., *EMBO* 14:1923–1931, 1995; Muzio et al., *J. Biol. Chem.* 273:2926–2930, 1998; Yang et al., *Mol. Cell* 1:319–325, 1998). To test if procaspase-9 can also be activated by heterologous oligomerization, WT and the C287A mutant procaspase-9 was fused to the mouse IgG-Fc portion which can form spontaneous dimers by intermolecular disulfide linkages. FIG. 9 depicts processing of non-fusion WT procaspase-9 (pcasp-9, lane 1) or C-terminal Fc-fusion WT (pcasp-9-Fc, lane 2) or C287A (active site) mutant (pcasp-9-C287A-Fc, lane 3) procaspase-9 which were in vitro translated in the presence of $^{35}$S-methionine and then analyzed by SDS-PAGE and autoradiography.

In vitro translated $^{35}$S-labeled procaspase-9-Fc fusion protein was capable of processing itself to the large subunit (p35 fragment) and a peptide corresponding to the small subunit (p12-Fc) (FIG. 9, lane 2). The C287A-Fc mutant (lane 3) and the WT procaspase-9 (lane 1) were incapable of processing and migrated as peptides corresponding to unprocessed procaspase-9.

Figure 10:
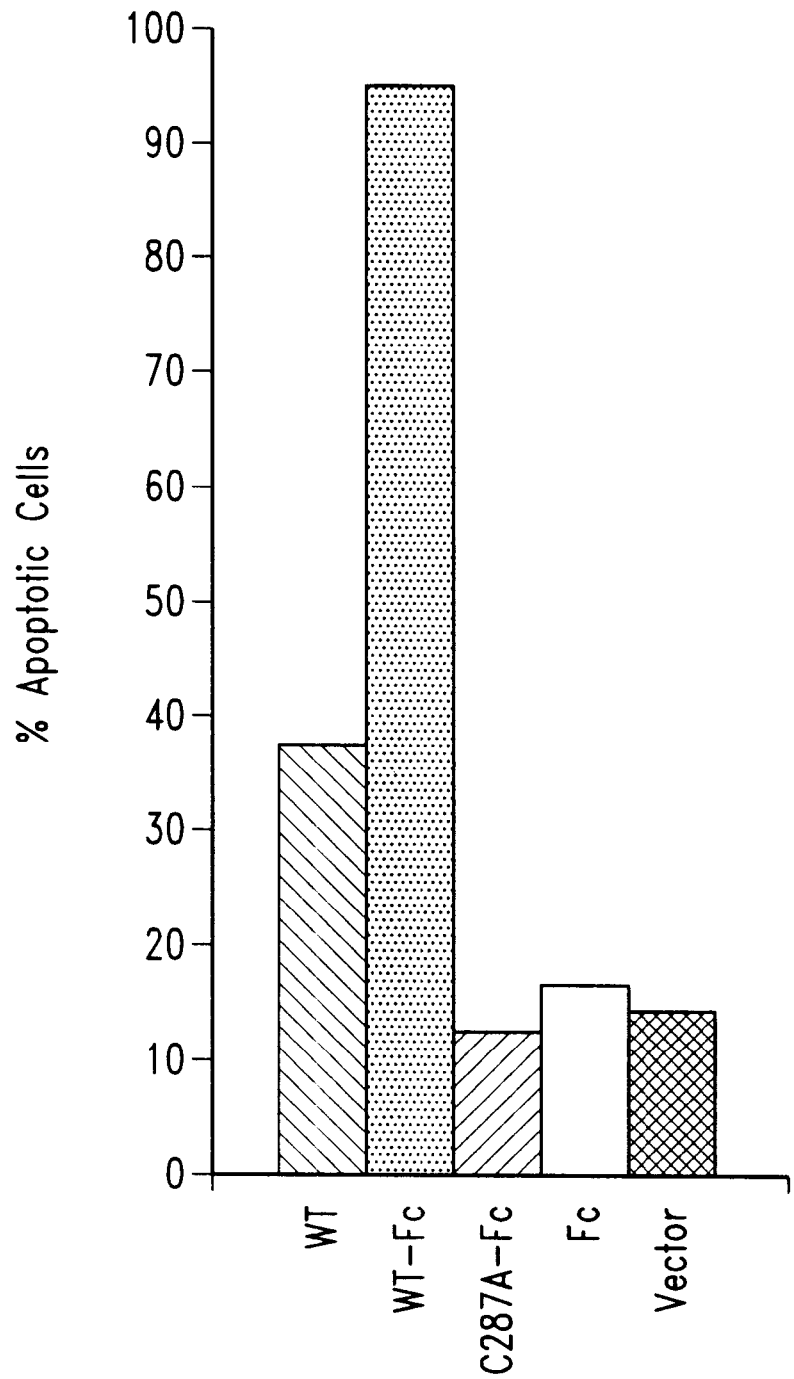
FIG. 10 is a bar diagram representing the ability of procaspase-Fc fusion constructs to oligomerize and induce apoptosis in MCF-7 cells. The bar diagram illustrates the percentage of round blue apoptotic cells (mean±S.D.) as a function of total blue cells under each condition (n≧3).

In vivo overexpression of the WT procaspase-9 in MCF-7 cells induced little apoptosis (FIG. 10). In FIG. 10, mammalian expression constructs encoding Fc or the procaspase-9 variants described in FIG. 9 were transfected into MCF-7 cells together with a reporter β-gal expression construct at a ratio of 3:1. 30 hours after transfection cells were stained with β-gal and examined for morphological signs of apoptosis. However, as illustrated, overexpression of the procaspase-9-Fc fusion protein potently induced apoptosis in 90% of transfected cells. The C287A-Fc mutant or Fc itself was unable to induce apoptosis. Taken together these data confirm that oligomerization can induce autocatalytic processing and activation of procaspase-9.

Example 9

APAF-530 FORMS OLIGOMERS

Figure 11:
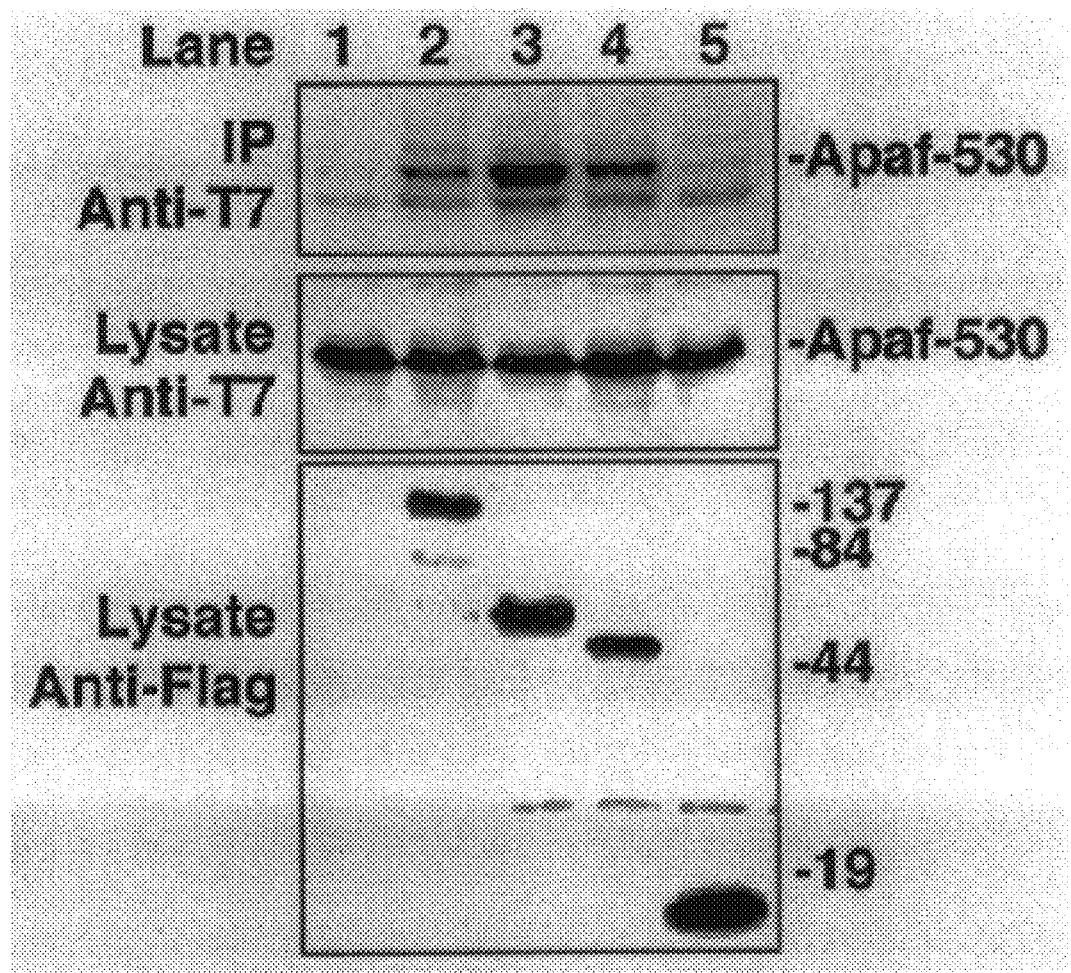
FIG. 11 is a scanned immunoblot representing SDS-PAGE analysis of the ability of N-terminal tagged Apaf-1 variants to form oligomers. The molecular mass markers are indicated to the right of the lower panel.

The ability of APAF-530 to oligomerize pro-caspase-9 was tested. Co-transfection experiments in 293 cells were performed with T7-tagged Apaf-530 and different Flag-tagged Apaf-1 variants, and cell lysates were prepared and immunoprecipitated with an anti-Flag antibody. The immunoprecipitates were analyzed by Western blotting with an anti-T7 antibody. As shown in FIG. 11, the T7-Apaf-530 co-immunoprecipitated with full length Flag-Apaf-1, Flag-Apaf-530 and Flag-Apaf-530ΔCARD, but not with Flag-Apaf-97, indicating that Apaf-530 forms oligomers through self association of its CED-4 homology domain.

In FIG. 11, 293 cells were co-transfected with constructs encoding T7-tagged Apaf-530 and an empty vector (lane 1) or constructs encoding Flag-tagged Apaf-1 (lane 2), Flag-tagged Apaf-530 (lane 3), Flag-tagged Apaf-530ΔCARD (lane 4) or Flag-tagged Apaf-97 (lane 5). After 36 hours, extracts were prepared and immunoprecipitated with a monoclonal antibody to the Flag epitope. The immunoprecipitates (upper panel) were analyzed by SDS-PAGE and immunoblotted with a horseradish peroxides-conjugated T7 antibody. The corresponding cellular extracts were also analyzed by SDS-PAGE and immunoblotted with a horseradish peroxides-conjugated T7 antibody (middle panel) or an anti-Flag antibody (lower panel).

Example 10

APAF-530 ACTIVATES PROCASPASE-9 BY OLIGOMERIZATION

Since Apaf-1 can form oligomers, it could bring two procaspase-9 into close proximity, allowing their subunits to complement each other. This process could then lead to the formation of a catalytically active intermediary complex capable of processing itself (FIG. 12). The complementation mechanism assumes that the two subunits of the mature heterodimer arise from two proximal precursor molecules. The mature caspase-9-like intermediary complex mechanism assumes that the two subunits of the mature heterodimer are derived from the same precursor molecule.

In this case, one subunit of the mature heterodimer is derived from the first precursor molecule and the other subunit from the second proximal precursor molecule. Alternatively, since the mature active form of caspases is a heterotetramer, Apaf-1 mediated oligomerization could result in the formation of a mature caspase-9-like intermediary complex capable of processing itself or adjacent molecules (FIG. 12). In this case the two subunits of the mature heterodimer are derived from the same precursor molecule.

To test the first possibility, procaspase-9 intragenic complementation experiments were performed with the Apaf-530 reconstitution system. Two procaspase-9 active site mutants one with a C287A mutation in the large subunit and the other with an R355E mutation in the small subunit were incubated with APAF-530. If Apaf-530 induces activation of procaspase-9 by complementation, then the C287A mutant and the R355E mutant should associate to form an active caspase capable of autoprocessing. On the other hand, if Apaf-530 induces procaspase-9 activation by formation of a mature caspase-9-like intermediary complex, these mutants would not be able to complement each other. In FIG. 13, $^{35}$S-labeled C287A or R355E mutant procaspase-9 were incubated with Apaf-530 separately (lanes 3 and 4, respectively) or together (lane 5) for 1 hour at 30° C. and analyzed by SDS-PAGE followed by autoradiography. WT procaspase-9 incubated with buffer (lane 1) or Apaf-530 (lane 2) were used as controls. As evidenced by FIG. 13, none of the mutants were able to autoprocess when incubated with Apaf-530 separately or together, indicating that Apaf-530 does not allow complementation-induced activation.

To test the second possibility, Apaf-530 was incubated with $^{35}$S-labeled full length C287A mutant (FIG. 14, lanes 1–4) or prodomainless procaspase-9 (FIG. 14, lanes 5–8) in the presence or absence of a non-radiolabeled WT procaspase-9. Samples were then analyzed by SDS-PAGE and autoradiography. If Apaf-530 induces activation of procaspase-9 by formation of a mature caspase-9-like intermediary complex capable of processing itself or adjacent molecules, then the WT procaspase-9 should associate with and process the C287A mutant, but not the prodomainless mutant. In another words, Apaf-530 will be able to bring the C287A mutant and the WT procaspase-9 into close proximity, but will not be able to do the same with the prodomainless mutant. The Apaf-530-procaspase-9 complex was able to induce processing of the C287A mutant, but not the prodomainless mutant (FIG. 14). This indicates that Apaf-530 oligomer was able to bring the two precursor molecules (WT and C287A) into close proximity forcing the WT molecule to process the C287A mutant. Because Apaf-530 cannot recruit the prodomainless mutant to the complex, the activated Apaf-530-bound caspase-9 was unable to process it.

Example 11

ACTIVATED APAF-530-BOUND CASPASE-9 CANNOT PROCESS PROCASPASE-3

It has recently been demonstrated that recombinant soluble caspase-9 or Apaf-1-activated caspase-9 can process procaspase-3 (Li et al., Cell 91:479–489, 1997). Interestingly, while analyzing the activity of the activated Apaf-530-bound caspase-9 towards procaspase-3, no processing of procaspase-3 was observed. This suggested that Apaf-530 is not able to release the activated caspase-9 from the complex. Therefore, if procaspase-3 could be brought into the complex, then the mature Apaf-530-bound caspase-9 should be able to process it. To achieve this, a chimeric procaspase-3 with an N-terminal caspase-9 prodomain was constructed. Caspase-9 prodomain in the chimera may allow recruitment of the chimeric procaspase-3 to the Apaf-530-caspase-9 complex. As evidenced by FIG. 15, when the chimeric procaspase-3 was incubated with Apaf-530 in the presence of nonradiolabeled procaspase-9, the chimeric procaspase-3 was processed to fragments corresponding to the large and small subunits. In FIG. 15, $^{35}$S-labeled chimeric procaspase-3 with an N-terminal procaspase-9 prodomain (lanes 1–4) or WT procaspase-3 (lanes 5–8) were incubated with buffer or Apaf-530 in the presence or absence of a non-radiolabeled WT procaspase-9 and analyzed by SDS-PAGE followed by autoradiography.

As shown in FIG. 15, no processing was observed with the non-chimeric WT procaspase-3 under the same conditions. Also, no processing was observed with the chimeric procaspase-3 in the absence of procaspase-9, suggesting that this process is specific for activation of procaspase-9. This provides further demonstration that Apaf-530 forms multimeric complexes. The difference between the activity of the full length Apaf-1 and the Apaf-530 complexes towards procaspase-3 suggest two possibilities either the full length Apaf-1 can release the activated caspase-9 from the complex where it can then activate procaspase-3 in the cytosol, or it could bring procaspase-3 into the complex where it gets activated by the bound caspase-9 and then released into the cytosol. Since the Apaf-530 lacks the WD-40 repeats, this may explain its inability to promote processing of procaspase-3.

Example 12

BCL-$x_L$ INTERACTS WITH APAF-1

In vivo interaction experiments between Apaf-1 variants and Bcl-$x_L$ were performed. To analyze the ability of Apaf-1 to interact with Bcl-$x_L$, 293 cells were co-transfected with constructs encoding T7-tagged Bcl-$x_L$ and constructs encoding Flag-tagged Apaf-97 (FIG. 16, lane 1), Apaf-1 (FIG. 16, lane 2), Apaf-530 (FIG. 16, lane 3) Apaf-530ΔCARD (FIG. 16, lane 4), or procaspase-9 C287A (FIG. 16, lane 5). After 36 hours, extracts were prepared and immunoprecipitated with a monoclonal antibody to the Flag epitope. The immunoprecipitates (FIG. 16, upper panel) were analyzed by SDS-PAGE and immunoblotted with a horseradish peroxidase-conjugated T7 antibody. The corresponding cellular extracts were also analyzed by SDS-PAGE and immunoblotted with a horseradish peroxides-conjugated T7 antibody (FIG. 16, middle panel) or an anti-Flag antibody (FIG. 16, lower panel).

As demonstrated by FIG. 16, full length Apaf-1, Apaf-530, and Apaf-530ΔCARD, but not Apaf-97 were all capable of immunoprecipitating Bcl-$x_L$. The ability of Bcl-$x_L$ to immunoprecipitate Apaf-530ΔCARD, but not Apaf-97, suggests that the interaction motif is present in the CED-4 homology region.

Bcl-$x_L$ was also capable of immunoprecipitating procaspase-9, suggesting that Bcl-$x_L$ could form a ternary complex with Apaf-1 and procaspase-9. A similar ternary complex composed of CED-9, CED-4, and CED-3 was described previously (Chinnaiyan et al., *Science* 275:1122–1126, 1997). Therefore, our data indicate that a Bcl-$x_L$-Apaf-1-procaspase-9 ternary complex may exist in mammalian cells.

Example 13

DOMINANT NEGATIVE CASPASE-9 INHIBITS MULTIPLE PATHWAYS OF APOPTOSIS

Recently it has been demonstrated that a dominant negative caspase-9 mutant (caspase-9-DN) can inhibit apoptosis induced by the proapoptotic members of the Bcl-2 family (Hegde et al., *J. Biol. Chem.* 273:7783–7786, 1998; Li et al., *Cell* 91:479–489, 1997). Caspase-9-DN can also inhibit apoptosis induced by UV, Fas agonist antibody, TRAIL, and overexpression of the TRAIL receptors, DR4 and DR5 (FIGS. 17 and 18). The ability of dominant negative procaspase-9 to inhibit apoptosis in vivo is presented in FIG. 17 wherein MCF-7 cells were transiently transfected with constructs expressing dominant negative procaspase-9-C287A mutant, Bcl-$x_L$ or X-IAP and a β-gal reporter plasmid and then treated 30 hours after transfection with the ligand TRAIL, agonist Fas-antibody, or UV. MCF-7 cells were also transiently transfected with pRSC-lacZ plasmids encoding DR4 or DR5 in combination with 4-fold excess of procaspase-9-C287A, Bcl-$x_L$ or X-IAP (X-linked Inhibitor of Apoptosis Protein), or empty vector.

The inhibition by the dominant negative caspase-9 mutant was as efficient as that observed with Bcl-$x_L$ or X-IAP. The caspase-9-DN was also able to attenuate cytochrome c/dATP-induced activation of procaspase-9 and procaspase-3 in the 293 S100 extract in a dose-dependent manner (FIG. 18). In FIG. 18, 293 cellular S100 extracts supplemented with $^{35}$S-labeled procaspase-9 (upper panel) or procaspase-3 (lower panel) were incubated with (lanes 3–7) or without (lane 2) cytochrome c plus dATP in the presence of increasing amounts of purified recombinant procaspase-9-C287A mutant for 1 hour at 30° C. and then analyzed by SDS-PAGE and autoradiography. A similar result was also obtained with the Apaf-530-induced activation of procaspase-9 in the in vitro reconstituted system (data not shown). This indicates that the Apaf-1/cytochrome c complex is the target of inhibition by caspase-9-DN in vivo. Consequently, the Apaf-1/caspase-9 pathway appears to be a central apoptotic pathway, on which most apoptotic signals converge.

What is claimed is:

1. An isolated truncated Apaf-1 polypeptide comprising a fragment of native human Apaf-1 (SEQ ID NO: 2), that induces proteolytic cleavage of procaspase-9 at Asp315 in the absence of cytochrome c or dATP.

2. The isolated truncated Apaf-1 polypeptide of claim 1, wherein said polypeptide comprises less than 60% of SEQ ID NO:2.

* * * * *

UNITED STATES PATENT AND TRADEMARK OFFICE
CERTIFICATE OF CORRECTION

PATENT NO. : 6,403,765 B1  Page 1 of 1
DATED : June 11, 2002
INVENTOR(S) : Emad S. Alnemri It is certified that error appears in the above-identified patent and that said Letters Patent is hereby corrected as shown below:

<u>Title page,</u>
Item [75], Inventors, "Emad S. Alnemri, Township Upper Dublin, County Montgomery, PA (US)" should read -- Emad S. Alnemri, Ambler, PA (US) --.

Signed and Sealed this

Twenty-eighth Day of January, 2003

JAMES E. ROGAN
*Director of the United States Patent and Trademark Office*